United States Patent
Meltzer et al.

(10) Patent No.: US 7,199,132 B2
(45) Date of Patent: Apr. 3, 2007

(54) TROPANE ANALOGS AND METHODS FOR INHIBITION OF MONOAMINE TRANSPORT

(75) Inventors: Peter C. Meltzer, Lexington, MA (US); Bertha K. Madras, Newton, MA (US); Paul Blundell, Winchester, MA (US)

(73) Assignees: Organix, Inc., Woburn, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/033,621

(22) Filed: Dec. 27, 2001

(65) Prior Publication Data

US 2003/0105125 A1 Jun. 5, 2003

Related U.S. Application Data

(60) Provisional application No. 60/327,963, filed on Oct. 9, 2001.

(51) Int. Cl.
*A61K 31/46* (2006.01)
*C07D 451/02* (2006.01)

(52) U.S. Cl. ................. 514/304; 546/127; 546/124
(58) Field of Classification Search ............ 514/304; 546/124, 127
See application file for complete search history.

(56) References Cited

U.S. PATENT DOCUMENTS

| | | | |
|---|---|---|---|
| 3,813,404 A | 5/1974 | Clarke et al. | 260/292 |
| 4,434,151 A | 2/1984 | Byrne et al. | |
| 4,499,099 A | 2/1985 | Watts | |
| 4,673,562 A | 6/1987 | Davison et al. | |
| 4,746,505 A | 5/1988 | Jones et al. | |
| 5,122,361 A | 6/1992 | Kung et al. | |
| 5,128,118 A | 7/1992 | Carroll et al. | |
| 5,310,912 A | 5/1994 | Neumeyer et al. | |
| 5,334,728 A | 8/1994 | Kung et al. | |
| 5,380,848 A | 1/1995 | Kuhar et al. | |
| 5,413,779 A | 5/1995 | Kuhar et al. | |
| 5,426,189 A | 6/1995 | Kung et al. | |
| 5,439,666 A | 8/1995 | Neumeyer et al. | |
| 5,493,026 A | 2/1996 | Elmaleh et al. | |
| 5,496,953 A | 3/1996 | Kuhar et al. | 546/125 |
| 5,760,055 A | 6/1998 | Davies | 514/304 |
| 5,980,860 A | 11/1999 | Kung et al. | |
| 6,008,227 A | 12/1999 | Davies et al. | 514/304 |
| 6,350,758 B1 | 2/2002 | Kozikowski et al. | 514/304 |
| 6,353,105 B1 * | 3/2002 | Meltzer et al. | 546/125 |
| 6,358,492 B1 | 3/2002 | Kuhar et al. | 424/1.85 |
| 6,670,375 B2 * | 12/2003 | Meltzer et al. | 514/304 |

FOREIGN PATENT DOCUMENTS

| | | |
|---|---|---|
| EP | 0 135 160 A2 | 3/1985 |
| WO | WO 93/09814 | 5/1993 |
| WO | WO 95/11901 | 5/1995 |
| WO | WO 97/14445 | 4/1997 |
| WO | WO 97/16210 | 5/1997 |
| WO | WO 97/47328 | 12/1997 |
| WO | WO 98/24788 | 6/1998 |
| WO | WO 99/02526 A1 | 1/1999 |
| WO | GB 2349882 A | 11/2000 |

OTHER PUBLICATIONS

Chen, Tetrahedron Letters 1997, vol. 38, No. 7, pp. 1121-1124, 1997.
Meltzer, Journal of Medicinal Chemistry 2001, vol. 44, No. 17, pp. 2619-2635, 2001.
Zhao, Journal of Medicinal Chemistry 2000, Vo. 43, No. 17, pp. 3283-3294, 2000.
Zhao, Tetrahedron Letters 1999, vol. 40, No. 27, pp. 4961-4964, 1994.
Brandau, et al., *Nucl. Med. Biol.* (1994) vol. 21, No. 8, pp. 1073-1081.
Bryson, et al., *Inorg. Chem.* (1988), 27, pp. 2154-2161.
Davison, et al., *Inorg. Chem.* (1981) vol. 20, No. 6, pp. 1629-1632.
DiZio, et al., *Bioconjugate Chemistry*, (1991) vol. 2, No. 5, pp. 353-366.
DiZio, et al., *Journal of Nuclear Medicine* (1992) vol. 33, No. 4, pp. 558-569.
Fritzberg, et al., *J. Nucl. Med.* (1981) vol. 22, No. 3, pp. 258-263.
Fritzberg, et al., *J. Nucl. Med.* (1982)vol. 23, No. 7, pp. 592-598.
Gustavson, et al., NeoRx Corp. Seattle, WA 98119, pp. 5485-5488.
Hansen, et al., *J. Nuc. Med.* (1994) vol. 35, No. 7, pp. 1198-1205.
Jones, et al., *J. Nucl. Med*, (1982)vol. 23, No. 9, pp. 801-809.
Steigman, et al., *National Academy Press* NAS-NS-3204 Prepared for the Committee on Nuclear and Radiochemistry, National Research Council (1992) pp. 117-127.
Archer, et al., University of Essex, Colchester, England, pp. 177-179.
Baldwin, et al., Yale Univ. School of Med., Westhaven, CT, pp. 329-332.
Kelly, et al., Amersham Int., Amersham, Bucks, UK, pp. 259-263.
Kung, et al., Univ. of PA, Philadelphia, PA, pp. 293-298.

(Continued)

*Primary Examiner*—Charanjit S. Aulakh
(74) *Attorney, Agent, or Firm*—George W. Neuner; Mark D. Russett; Edwards Angell Palmer & Dodge LLP

(57) ABSTRACT

New tropane analogs that bind to monoamine transporters are described, particularly, 8-aza, 8carbo and 8-oxo tropanes having 6- or 7-hydroxyl or ketone substituents. The compounds of the present invention can be racemic, pure R-enantiomers, or pure S-enantiomers. Certain preferred compounds of the present invention have a high selectivity for the DAT versus the SERT. Also described are pharmaceutical therapeutic compositions comprising the compounds formulated in a pharmaceutically acceptable carrier and a method for inhibiting 5-hydroxy-tryptamine reuptake of a monoamine transporter by contacting the monoamine transporter with a 5-hydroxytryptamine reuptake inhibiting amount of a compound of the present invention. Preferred monoamine transporters for the practice of the present invention include the dopamine transporter, the serotonin transporter and the norepinephrine transporter.

29 Claims, 8 Drawing Sheets

OTHER PUBLICATIONS

Liu et al., *The* Dupont Merck Pharm. *Co.* N. Billerica, MA, pp. 383-393.
Mahmood, et al., Harvard Medical School, Boston, MA, pp. 211-215.
Volkert, Univ. of Missouri Columbia, MO, pp. 17-26.
Davies, et al, *J. Med. Chem*, (1994) vol. 37, No. 9, pp. 1262-1268.
Bennett, et al., *J. of Pharmacology* (1995) vol. 272, No. 3, pp. 1176-1186.
Rao, et al, Eighth International Symposium on Radiopharmaceutical Chemistry, Princeton Univ. (1990) pp. 39-40.
Johannsen, et al., *Eleventh Intern. Symposium Radiopharmaceutical Chem. Abstracts* (1995), pp. 319-320.
Agoston, et al., *Amer. Chem. Society*, (1997) vol. 40, No. 26, pp. 4329-4339.
Carroll, et al., *J. Med. Chem*. (1993) vol. 36, No. 20, pp. 2886-2890.
Casy, et al., *J. Pharm. Pharmacol*. (1992) vol. 44, pp. 787-790.
Daum, et al., *J. Med. Chem* (1975), vol. 18, No. 5, pp. 496-501.
Holmquist, et al., *J. Med. Chem* (1996), vol. 39, No. 21, pp. 4139-4141.
Meegalla, et al., *J. Am. Chem. Soc*. (1995) vol. 117, No. 44, pp. 11037-11038.
Meegalla, et al., *J. Am. Chem. Soc*. (1996) vol. 7, No. 4, pp. 421-429.
Clarke, et al., *J. Med. Chem*. (1973) vol. 16, No. 11, pp. 1260-1267.
Ohmomo, et al., *J. Med. Chem*. (1992) vol. 35, No. 1, pp. 157-162.
Carroll, et al., *J. Med. Chem*. (1995) vol. 38, No. 2, pp. 379-388.
Kline, et al., *J. Med. Chem*. (1997) vol. 40, No. 6, pp. 851-857.
Meltzer, et al., *J. Med. Chem*. (1996) vol. 39, No. 2, pp. 371-379.
Meltzer, et al., *J. Med. Chem*. (1997) vol. 40, No. 17, pp. 2661-2673.
Meltzer, et al., *J. Med. Chem* (1994) vol. 37, No. 13, pp. 2001-2010.
Newman, et al., *J. Med. Chem*. (1999) vol. 42, No. 18, pp. 3502-3509.
Newman, et al., *J. Med. Chem*. (1995) vol. 38, No. 20, pp. 3933-3940.
Newman, et al., *Current Medicinal Chem*. (1998) vol. 5, No. 4, pp. 305-319.
Newman, et al., *J. Med. Chem*. (1994) vol. 37, No. 15, pp. 2258-2261.
Riley et al., *J. Med. Chem*. (1979) pp. 1167-1171.
Van Eeken, et al., *Arch. Int. Pharmacodyn* (Netherlands) (1966) vol. 22, No. 10, vol. 159, No. 1, pp. 240-249.
Cesati, et al., *J. Labelled Cpd. Radiopharm*, (1999) vol. 42, Suppl. j, pp. S150-S152.
Fang, et al., *J. Labelled Cpd. Radiopharm*. (1999) vol. 42, Suppl. i, pp. S336-S338.
Hoepping, et al., Universitat Marburg, Pachbereich Kemchemie, (1997) pp. 33-36.
Hoepping, et al., *Bioorganic & Medicinal Chem*. (1998) vol. 6, pp. 1663-1672.
Hoepping, et al., *Bioorganic & Medicinal Chem*. (1996) vol. 6, No. 23, pp. 2871-2874.
Hoepping, et al., *J. Med. Chem*. (1998) vol. 41, No. 23, pp. 4429-4432.
Madras, et al., *Synapse* (1996) vol. 22, pp. 239-246.
Meegalla, et al., *J. Med. Chem*. (1997) vol. 40, No. 1, pp. 9-17.
Meltzer, et al., *J. Med. Chem*. (1997) vol. 40, No. 12, pp. 1835-1844.
Meltzer, et al., *J. Med. Chem*. (1993) vol. 36, No. 7 pp. 855-862.
Meltzer, et al., *Med. Chem. Research* (1998) pp. 12-34.
Meegalla, et al., *Bioconjugate Chem*. (1996) vol. 7, No. 4, pp. 421-429.
Fischman, et al., *J. Nuclear Med*. (1999) vol. 40, No. 5 Supplement, p. 262P.
Mozley, et al., *J. Nuclear Med*. (1995) vol. 36, No. 5, p. 32P.
Myers, et al., *J. Nuclear Med*. (1995) vol. 36, No. 5, p. 124P.

* cited by examiner

Figure 1. Structures of Lead Bicyclo[3.2.1]octanes

Figure 2. Absolute Configurations of (1R)-8a, (1R)-18a, (1S)-18a

Scheme 1. Synthetic Route to 2,3-Unsaturated Tropanes[a]

Ar: a = 3,4-Cl₂ phenyl   b = 2-Naphthyl   c = 4-F-phenyl   d = Phenyl

[a] Reagents: (i) H₂NCH₃; (ii) CH₂(OCH₃)₂, pTSA; (iii) NaN(TMS)₂, PhNTf₂; (iv) Pd₂(dba)₃, ArB(OH)₂; (v) TMSBr.

Scheme 2. Synthetic Route to Bridge Oxygenated Tropanes[a]

[a] Reagents: (i) SmI₂; (ii) TMSBr, CH₂Cl₂; (iii) N-CH₃-morpholine-N-oxide, tetra-n-propylammoniumperruthenate.

Scheme 3. Synthetic Route to Bridge Oxygenated 2-Keto Tropanes[a]

[a] Reagents: (i) HN(CH$_3$)OCH$_3$, Al(CH$_3$)$_3$; (ii) ETMgBR; (iii) TMSBR, CH$_2$Cl$_2$.

Scheme 4. Resolution of 8A, 15A, and 18A[a]

Scheme 5. Inversion at C6 and C7[a]

[a] Reagents: (i) C6H5COOH, Ph3P, DEAD; (ii) LiOH, THF.

Scheme 6. Synthesis of Diarylmethoxy Tropanes[a]

[a] Reagents: (i) NaBH₄; (ii) 4,4'-difluorobenzhydrol, pTSA.

TROPANE ANALOGS AND METHODS FOR INHIBITION OF MONOAMINE TRANSPORT

This application claims benefit of provisional application 60/327,963 filed Oct. 09, 2001.

FIELD OF THE INVENTION

This invention relates to tropane analogs of cocaine and their use as inhibitors of monoamine reuptake.

BACKGROUND OF THE INVENTION

Cocaine dependence is a problem of national significance. To date no cocaine pharmacotherapy has been reported. Cocaine is a potent stimulant of the mammalian central nervous system. Its reinforcing properties and stimulant effects are associated with its propensity to bind to monoamine transporters, particularly the dopamine transporter (DAT). (Kennedy, L. T. and I. Hanbauer (1983), *J. Neurochem.* 34: 1137–1144; Kuhar, M. J., M. C. Ritz and J. W. Boja (1991), *Trends Neurosci.* 14: 299–302; Madras, B. K., M. A. Fahey, J. Bergman, D. R. Canfield and R. D. Spealman (1989), *J. Pharmacol. Exp. Ther.* 251: 131–141; Madras, B. K., J. B. Kamien, M. Fahey, D. Canfield, et al. (1990), *Pharmacol Biochem. Behav.* 35: 949–953; Reith, M. E. A., B. E. Meisler, H. Sershen and A. Lajtha (1986), *Biochem. Pharmacol.* 35: 1123–1129; Ritz, M. C., R. J. Lamb, S. R. Goldberg and M. J. Kuhar (1987), *Science* 237: 1219–1223; Schoemaker, H., C. Pimoule, S. Arbilla, B. Scatton, F. Javoy-Agid and S. Z. Langer (1985), *Naunyn-Schmiedeberg's Arch. Pharmacol.* 329: 227–235.) It also binds with substantial potency to serotonin transporters (SERT) and norepinephrine transporters.

Structure activity relationship (SAR) studies have largely focused on a series of cocaine analogs. Among the more potent of these congeners at $^3$H-cocaine binding sites in striatum (Madras, B. K., M. A. Fahey, J. Bergman, D. R. Canfield and R. D. Spealman (1989), *J. Pharmacol. Exp. Ther.* 251: 131–141; Reith, M. E. A., B. E. Meisler, H. Sershen and A. Lajtha (1986), *Biochem. Pharmacol.* 35: 1123–1129) is (1R)-3β-(4-fluorophenyl)tropane-2β-carboxylic acid methyl ester, (WIN35,428 or CFT) (Kaufman, M. J. and B. K. Madras (1992), *Synapse* 12: 99–111; Madras, B. K., M. A. Fahey, J. Bergman, D. R. Canfield and R. D. Spealman (1989), *J. Pharmacol. Exp. Ther.* 251: 131–141) reported in 1973 (Clarke, R. L, S. J. Daum, A. J. Gambino, M. D. Aceto, et al. (1973), *J. Med. Chem.* 16: 1260–1267). This compound was subsequently radiolabeled to provide a selective probe for the DAT in primate brain. (Canfield, D. R., R. D. Spealman, M. J. Kaufman and B. K. Madras (1990), Synapse 6: 189–195; Kaufman, M. J. and B. K. Madras (1991), *Synapse* 9: 43–49; Kaufman, M. J., R. D. Spealman and B. K. Madras (1991), *Synapse* 9: 177–187.)

Among the most potent tropane inhibitors of monoamine binding sites in striatum are 3β-{4-(1-methylethenyl)-phenyl})2β-propanoyl-8-azabicyclo(3.2.1)octane and 3β-(2-naphthyl)-2β-propanoyl-8-azabicyclo(3.2.1)octane, (Bennett, B. A., C. H. Wichems, C. K. Hollingsworth, H. M. L. Davies, C. Thornley, T. Sexton and S. R. Childers (1995), *J. Pharm. Exp. Ther.* 272: 1176–1186; Davies, H. M. L., L. A. Kuhn, C. Thornley, J. J. Matasi, T. Sexton and S. R. Childers (1996), *J. Med. Chem.* 39: 2554–2558) (1R)-RTI155 (βCIT), (Boja 1991; Boja, J. W., A. Patel, F. I. Carroll, M. A. Rahman, et al. (1991), *Eur. J. Pharmacol.* 194: 133–134; Neumeyer, J. L., S. Wang, R. A. Milius, R. M. Baldwin, et al. (1991), *J. Med. Chem.* 34: 3144–3146) (1R)-RTI121, (Carroll, F. I., A. H. Lewin, J. W. Boja and M. J. Kuhar (1992), *J. Med. Chem.* 35: 969–981.) and (1R)-3β-(3,4-dichlorophenyl)-tropane-2β-carboxylic acid methyl ester (O-401), (Carroll, F. I., M. A. Kuzemko and Y. Gao (1992), *Med. Chem Res.* 1: 382–387; Meltzer, P. C., A. Y. Liang, A.-L. Brownell, D. R. Elmaleh and B. K. Madras (1993), *J. Med. Chem.* 36: 855–862).

SAR studies of the binding of these agents and their effects on monoamine transporter function have been reported. (Blough, B. E., P. Abraham, A. H. Lewin, M. J. Kuhar, J. W. Boja and F. I. Carroll (1996), *J. Med. Chem.* 39: 4027–4035; Carroll, F. I., P. Kotian, A. Dehghani, J. L. Gray, et al. (1995), *J. Med. Chem.* 38: 379–388; Carroll, F. I., A. H. Lewin, J. W. Boja and M. J. Kuhar (1992),y *J. Med. Chem.* 35: 969–981; Carroll, F. I., S. W. Mascarella, M. A. Kuzemko, Y. Gao, et al. (1994), *J. Med. Chem.* 37: 2865–2873; Chen, Z., S. Izenwasser, J. L. Katz, N. Zhu, C. L. Klein and M. L. Trudell (1996), *J. Med. Chem.* 39: 4744–4749; Davies, H. M. L., L. A. Kuhn, C. Thornley, J. J. Matasi, T. Sexton and S. R. Childers (1996), *J. Med. Chem.* 39: 2554–2558; Davies, H. M. L., Z. -Q. Peng and J. H. Houser (1994), *Tetrahedron Lett.* 48: 8939–8942; Davies, H. M. L., E. Saikali, T. Sexton and S. R. Childers (1993), *Eur. J. Pharmacol. Mol. Pharm.* 244: 93–97; Holmquist, C. R., K. I. Keverline-Frantz, P. Abraham, J. W. Boja, M. J. Kuhar and F. I. Carroll (1996), *J. Med. Chem* 39: 4139–4141; Kozikowski, A. P., G. L. Araldi and R. G. Ball (1997), *J. Org. Chem.* 62: 503–509; Kozikowski, A. P., M. Roberti, L. Xiang, J. S. Bergmann, P. M. Callahan, K. A. Cunningham and K. M. Johnson (1992), *J. Med. Chem.* 35: 4764–4766; Kozikowski, A. P., D. Simoni, S. Manfredini, M. Roberti and J. Stoelwinder (1996), *Tetrahedron Lett.* 37: 5333–5336; Meltzer, P. C., A. Y. Liang, A.-L. Brownell, D. R. Elmaleh and B. K. Madras (1993), *J. Med. Chem.* 36: 855–862; Meltzer, P. C., A. Y. Liang and B. K. Madras (1994), *J. Med. Chem.* 37: 2001–2010; Meltzer, P. C., A. Y. Liang and B. K. Madras (1996), *J. Med. Chem.* 39: 371–379; Newman, A. H., A. C. Allen, S. Izenwasser and J. L. Katz (1994), *J. Med Chem.* 37: 2258–2261; Newman, A. H., R. H. Kline, A. C. Allen, S. Izenwasser, C. George and J. L. Katz (1995), *J. Med. Chem.* 38: 3933–3940; Shreekrishna, V. K., S. Izenwasser, J. L. Katz, C. L. Klein, N. Zhu and M. L. Trudell (1994), *J. Med. Chem.* 37: 3875–3877; Simoni, D., J. Stoelwinder, A. P. Kozikowski, K. M. Johnson, J. S. Bergmann and R. G. Ball (1993), *J. Med. Chem.* 36: 3975–3977.)

Binding of cocaine and its tropane analogs to monoamine transporters is stereoselective. As example (1R)-(−)-cocaine binds at the dopamine transporter about 200-fold more potently than the unnatural isomer, (1S)-(+)-cocaine. (Kaufman, M. J. and B. K. Madras (1992), *Synapse* 12: 99–111; Madras, B. K., M. A. Fahey, J. Bergman, D. R. Canfield and R. D. Spealman (1989), *J. Pharmacol. Exp. Ther.* 251: 131–141; Madras, B. K., R. D. Spealman, M. A. Fahey, J. L. Neumeyer, J. K. Saha and R. A. Milius (1989), *Mol. Pharmacol.* 36: 518–524; Reith, M. E. A., B. E. Meisler, H. Sershen and A. Lajtha (1986), *Biochem. Pharmacol.* 35: 1123–1129; Ritz, M. C., R. J. Lamb, S. R. Goldberg and M. J. Kuhar (1987), *Science* 237: 1219–1223.)

Also, only the R-enantiomers of cocaine have been found active in a variety of biological and neurochemical measures. (Clarke, R. L., S. J. Daum, A. J. Gambino, M. D. Aceto, et al. (1973), *J. Med. Chem.* 16: 1260–1267; Kaufman, M. J. and B. K. Madras (1992), *Synapse* 12: 99–111; Madras, B. K., M. A. Fahey, J. Bergman, D. R. Canfield and R. D. Spealman (1989), *J. Pharmacol. Exp. Ther.* 251: 131–141; Madras, B. K., R. D. Spealman, M. A. Fahey, J. L. Neumeyer, J. K. Saha and R. A. Milius (1989), *Mol. Phar-* macol. 36: 518–524; Reith, M. E. A., B. E. Meisler, H. Sershen and A. Lajtha (1986), *Biochem. Pharmacol.* 35: 1123–1129; Ritz, M. C., R. J. Lamb, S. R. Goldberg and M. J. Kuhar (1987), *Science* 237: 1219–1223; Sershen, H., M. E. A. Reith and A. Lajtha (1980), *Neuropharmacology* 19: 1145–1148; Sershen, H., M. E. A. Reith and A. Lajtha (1982), *Neuropharmacology* 21: 469–474; Spealman, R. D., R. T. Kelleher and S. R. Goldberg (1983), *J. Pharmacol. Exp. Ther.* 225: 509–513.) Parallel stereoselective behavioral effects have also been observed. (Bergman, J., B. K. Madras, S. E. Johnson and R. D. Spealman (1989), *J. Pharmacol. Exp. Ther.* 251: 150–155; Heikkila, R. E., L. Manzino and F. S. Cabbat (1981), *Subst. Alcohol Actions/Misuse* 2: 115–121; Reith, M. E. A., B. E. Meisler, H. Sershen and A. Lajtha (1986), *Biochem. Pharmacol.* 35: 1123–1129; Spealman, R. D., R. T. Kelleher and S. R. Goldberg (1983), *J. Pharmacol. Exp. Ther.* 225: 509–513; Wang, S., Y. Gai, M. Laruelle, R. M. Baldwin, B. E. Scanlet, R. B. Innis and J. L. Neumeyer (1993), *J. Med. Chem.* 36:1914–1917.) For example, in primates and rodents the stimulating and reinforcing properties of the (−)-enantiomer of cocaine or its 3-aryltropane analogs were considerably greater than for the (+)-enantiomers.

Although SAR studies of cocaine and its 3-aryltropane analogs have offered insight into their mode of binding to monoamine transporters, a comprehensive picture of the binding interaction at the molecular level has not emerged. SAR studies on the classical tropane analogs (Carroll, F. I., Y. Gao, M. A. Rahman, P. Abraham, et al. (1991), *J. Med. Chem.* 34: 2719–2725; Carroll, F. I., S. W. Mascarella, M. A. Kuzemko, Y. Gao, et al. (1994), *J. Med. Chem.* 37: 2865–2873; Madras, B. K., M. A. Fahey, J. Bergman, D. R. Canfield and R. D. Spealman (1989), *J. Pharmacol. Exp. Ther.* 251: 131–141; Madras, B. K., R. D. Spealman, M. A. Fahey, J. L. Neumeyer, J. K. Saha and R. A. Milius (1989), *Mol. Pharmacol.* 36: 518–524; Meltzer, P. C., A. Y. Liang, A.-L. Brownell, D. R. Elmaleh and B. K. Madras (1993), *J. Med. Chem.* 36: 855–862; Reith, M. E. A., B. E. Meisler, H. Sershen and A. Lajtha (1986), *Biochem. Pharmacol.* 35: 1123–1129) appeared to provide a consistent model for this interaction with the DAT, however, subsequent studies revealed inconsistencies. (Carroll, F. I., P. Kotian, A. Dehghani, J. L. Gray, et al. (1995), *J. Med. Chem.* 38: 379–388; Chen, Z., S. Izenwasser, J. L. Katz, N. Zhu, C. L. Klein and M. L. Trudell (1996), *J. Med. Chem.* 39: 4744–4749; Davies, H. M. L., L. A. Kuhn, C. Thomley, J. J. Matasi, T. Sexton and S. R. Childers (1996), *J. Med. Chem.* 39: 2554–2558; Kozikowski, A. P., G. L. Araldi and R. G. Ball (1997), *J. Org. Chem.* 62: 503–509; Meltzer, P. C., A. Y. Liang and B. K. Madras (1994), *J. Med. Chem.* 37: 2001–2010; Meltzer, P. C., A. Y. Liang and B. K. Madras (1996), *J. Med. Chem.* 39: 371–379.)

Carroll had proposed (Boja, J. W., R. M. McNeill, A. Lewin, P. Abraham, F. I. Carroll and M. J. Kuhar (1992), *Mol. Neurosci.* 3: 984–986; Carroll, F. I., P. Abraham, A. Lewin, K. A. Parham, J. W. Boja and M. J. Kuhar (1992), *J. Med. Chem.* 35: 2497–2500; Carroll, F. I., Y. Gao, M. A. Rahman, P. Abraham, et al. (1991), *J. Med. Chem.* 34: 2719–2725; Carroll, F. I., M. A. Kuzemko and Y. Gao (1992), *Med. Chem Res.* 1: 382–387) four molecular requirements for binding of cocaine and its tropane analogs at the DAT: a 2β-carboxy ester, a basic nitrogen capable of protonation at physiological pH, the R-configuration of the tropane and a 3β-aromatic ring at $C_3$. However, Davies (Davies, H. M. L., E. Saikali, T. Sexton and S. R. Childers (1993), *Eur. J. Pharmacol. Mol. Pharm.* 244: 93–97) later reported that introduction of 2β-ketones did not reduce potency. Kozikowski questioned the role of hydrogen bonding at the $C_2$ site because introduction of unsaturated and saturated alkyl groups (Kozikowski, A. P., M. Roberti, K. M. Johnson, J. S. Bergmann and R. G. Ball (1993), *Bioorg. Med. Chem. Lett.* 3: 1327–1332; Kozikowski, A. P., M. Roberti, L. Xiang, J. S. Bergmann, P. M. Callahan, K. A. Cunningham and K. M. Johnson (1992), *J. Med. Chem.* 35: 4764–4766) did not diminish binding. Further, the ionic bond between a protonated amine (at physiologically pH) and the presumed (Kitayama, S., S. Shimada, H. Xu, L. Markham, D. H. Donovan and G. R. Uhl (1993), *Proc. Natl. Acad. Sci. U.S.A.* 89: 7782–7785) aspartate residue on the DAT was questioned because reduction of nitrogen nucleophilicity (Kozikowski, A. P., M. K. E. Saiah, J. S. Bergmann and K. M. Johnson (1994), *J. Med. Chem.* 37(37): 3440–3442) by introduction of N-sulfones did not reduce binding potency.

It also has been reported (Madras, B. K., J. B. Kamien, M. Fahey, D. Canfield, et al. (1990), *Pharmacol Biochem. Behav.* 35: 949–953) that introduction of an alkyl or allyl group did not eliminate binding potency. An N-iodoallyl group on the tropane has provided potent and selective ligands for the DAT, and altropane is currently being developed as a SPECT imaging agent (Elmaleh, D. R., B. K. Madras, T. M. Shoup, C. Byon, et al. (1995), *J. Nucl. Chem.,* 371197–1202 (1966); Fischman, A. J., A. A. Bonab, J. W. Babich, N. M. Alpert, et al. (1996), *Neuroscience-Net* 1, 00010, (1997). A $^{99m}$technetium labeled compound, technepine, which binds potently and selectively to the DAT and provides excellent in vivo SPECT images has been reported. (Madras, B. K., A. G. Jones, A. Mahmood, R. E. Zimmerman, et al. (1996), *Synapse* 22: 239–246.) (Meltzer, P. C., Blundell, P., Jones, A. G., Mahmood, A., Garada, B. et al., *J. Med. Chem.,* 40, 1835–1844, (1997). 2-Carbomethoxy-3-(bis(4-fluorophenyl)methoxy)tropanes have been reported (Meltzer, P. C., A. Y. Liang and B. K. Madras (1994), *J. Med. Chem.* 37: 2001–2010). The S -enantiomer, (S)-(+)-2β-carbomethoxy-3α-(bis(4-fluorophenyl)methoxy)tropane (Difluoropine) was considerably more potent ($IC_{50}$: 10.9 nM) and selective (DAT v. SERT: 324) than any of the other seven isomers, including the R-enantiomers.

Drug therapies for cocaine abuse are needed. Also, there is a need for protective agents for neurodegenerative diseases such as Parkinson's disease and Alzheimer's disease as well as therapeutic agents for dopamine related dysfunction such as Attention Deficit Disorder. Compounds that inhibit monoamine reuptake in the mammalian system are sought to provide such therapies.

Inhibition of 5-hydroxytryptamine reuptake has an effect on diseases mediated by 5HT receptors. Compounds that provide such inhibition can be useful, for example, as therapeutic anti-depressants.

Cocaine recognition sites are localized on monoamine transporters such as, for example, the dopamine transporter (DAT) and serotonin transporter (SERT). These transporters are localized, in turn, on monoamine nerve terminals. Compounds that bind to these sites can be useful as (i) probes for neuro-degenerative diseases (e.g., Parkinson's disease), (ii) therapeutic drugs for neurodegenerative diseases (e.g., Parkinson's and Alzheimer's disease), (iii) therapeutic drugs for dopamine dysfunction (e.g., Attention Deficit Disorder), (iv) treatment of psychiatric dysfunction (e.g., depression) and (v) treatment of clinical dysfunction (e.g., migraine).

SUMMARY OF THE INVENTION

The compounds of this invention are new tropane analogs that bind to monoamine transporters. Thus, the present invention provides tropane analogs having one of the following formula:

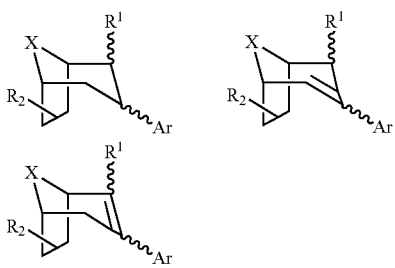

wherein:

$R_1$=COOR$_7$, COR$_3$, lower alkyl, lower alkenyl, lower alkynyl, CONHR$_4$, or COR$_6$ and is α or β;

$R_2$=OH or O, is a 6- or 7-substituent, and if $R_2$ is OH, it is α or β;

X=NR$_3$, CH$_2$, CHY, CYY$_1$, CO, O, S; SO, SO$_2$, NSO$_2$R$_3$, or C=CX$_1$Y with the N, C, O or S atom being a member of the ring;

X$_1$=NR$_3$, CH$_2$, CHY, CYY$_1$ CO, O, S; SO, SO$_2$, or NSO$_2$R$_3$;

R$_3$=H, (CH$_2$)$_n$C$_6$H$_4$Y, C$_6$H$_4$Y, CHCH$_2$, lower alkyl, lower alkenyl or lower alkynyl;

Y and Y$_1$=H, Br, Cl, I, F, OH, OCH$_3$, CF$_3$, NO$_2$, NH$_2$, CN, NHCOCH$_3$, N(CH$_3$)$_2$, (CH$_2$)nCH$_3$, COCH$_3$, or C(CH$_3$)$_3$;

R$_4$=CH$_3$, CH$_2$CH$_3$, or CH$_3$SO$_2$;

R$_6$=morpholinyl or piperidinyl;

Ar=phenyl-R$_5$, naphthyl-R$_5$, anthracenyl-R$_5$, phenanthrenyl-R$_5$, or diphenylmethoxy-R$_5$;

R$_5$=H, Br, Cl, I, F, OH, OCH$_3$, CF$_3$, NO$_2$, NH$_2$, CN, NHCOCH$_3$, N(CH$_3$)$_2$, (CH$_2$)nCH$_3$, COCH$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);

n=0, 1, 2, 3, 4 or 5;

R$_7$=lower alkyl; and when X=N, R$_1$ is not COR$_6$.

The substituents at the 2 and 3 position of the ring can be α- or β. Although R$_1$ is illustrated in the 2-position, it should be recognized that substitution at the 4-position is also included and the position is dependent on the numbering of the tropane ring. The compounds of the present invention can be racemic, pure R-enantiomers, or pure S-enantiomers. Thus, the structural formulas illustrated herein are intended to represent each enantiomer and diastereomer of the illustrated compound. In certain preferred compounds of the present invention, R$_1$ is COOCH$_3$. In yet other preferred compounds, R$_1$ is COR$_3$, where R$_3$ is CHCH$_2$ Other preferred compounds are 6 or 7-bridge hydroxylated or keto compounds The compounds of the present invention can be radiolabelled, for example, to assay cocaine receptors. Certain preferred compounds of the present invention have a high selectivity for the DAT versus the SERT. Preferred compounds have an IC$_{50}$ SERT/DAT ratio of greater than about 10, preferably greater than about 30 and more preferably 50 or more. In addition, preferably the compounds have an IC$_{50}$ at the DAT of less than about 500 nM, preferably less than 60 nM, more preferably less than about 20, and most preferably less than about 10.

The present invention also provides pharmaceutical therapeutic compositions comprising the compounds formulated in a pharmaceutically acceptable carrier.

Further, the invention provides a method for inhibiting 5-hydroxytryptamine reuptake of a monoamine transporter by contacting the monoamine transporter with a 5-hydroxytryptamine reuptake inhibiting (5-HT inhibiting) amount of a compound of the present invention. Inhibition of 5-hydroxy-tryptamine reuptake of a monoamine transporter in a mammal is provided in accord with the present invention by administering to the mammal a 5-HT inhibiting amount of a compound of the present invention in a pharmaceutically acceptable carrier. Preferred monoamine transporters for the practice of the present invention include the dopamine transporter, the serotonin transporter and the norepinephrine transporter.

In a preferred embodiment, the invention also provides a method for inhibiting dopamine reuptake of a dopamine transporter by contacting the dopamine transporter with a dopamine reuptake inhibiting amount of a compound of the present invention. Inhibition of dopamine reuptake of a dopamine transporter in a mammal is provided in accord with the present invention by administering to the mammal a dopamine inhibiting amount of a compound of the present invention in a pharmaceutically acceptable carrier.

The invention also relates to a method for treating a mammal having a disorder selected from neurodegenerative disease, psychiatric dysfunction, dopamine dysfunction, cocaine abuse and clinical dysfunction comprising administering to the mammal an effective amount of a compound of the present invention. In preferred methods, the compound has a 3α-group. In certain methods, the neurodegenerative disease is selected from Parkinson's disease and Alzheimer's disease. An example of a psychiatric disorder which can be treated by the present methods is depression.

The invention also relates to methods for treating dopamine related dysfunction in a mammal comprising administering to the mammal a dopamine reuptake inhibiting amount of a compound as described herein. In preferred methods, the compound is a boat tropane. An example of a dopamine related dysfunction is Attention deficit disorder.

The term "lower alkyl" when used herein designates aliphatic saturated branched or straight chain hydrocarbon monovalent substituents containing from 1 to about 8 carbon atoms such as methyl, ethyl, isopropyl, n-propyl, n-butyl, (CH$_2$)$_n$CH$_3$, C(CH$_3$)$_3$; etc., more preferably 1 to 4 carbons. The term "lower alkoxy" designates lower alkoxy substituents containing from 1 to about 8 carbon atoms such as methoxy, ethoxy, isopropoxy, etc., more preferably 1 to 4 carbon atoms.

The term "lower alkenyl" when used herein designates aliphatic unsaturated branched or straight chain vinyl hydrocarbon substituents containing from 2 to about 8 carbon atoms such as allyl, etc., more preferably 2 to 4 carbons. The term "lower alkynyl" designates lower alkynyl substituents containing from 2 to about 8 carbon atoms, more preferably 2 to 4 carbon atoms such as, for example, propyne, butyne, etc.

The terms substituted lower alkyl, substituted lower alkoxy, substituted lower alkenyl and substituted lower alkynyl, when used herein, include corresponding alkyl, alkoxy, alkenyl or alkynyl groups substituted with halide, hydroxy, carboxylic acid, or carboxamide groups, etc. such as, for example, —CH$_2$OH, —CH$_2$CH$_2$COOH, —CH$_2$CONH$_2$, —OCH$_2$CH$_2$OH, —OCH$_2$COOH, —OCH$_2$CH$_2$CONH$_2$, etc. As used herein, the terms lower alkyl, lower alkoxy, lower alkenyl and lower alkynyl are meant to include where practical substituted such groups as described above.

When X contains a carbon atom as the ring member, reference to X is sometimes made herein as a carbon group. Thus, when X is a carbon group, as that phrase is used herein, it means that a carbon atom is a ring member at the X position (i.e., the 8-position).

BRIEF DESCRIPTION OF THE DRAWINGS

FIG. 2 illustrates the absolute Configurations of (1R)-8a, (1R)-18a, (1S)-18a.

FIG. 6 illustrates a reaction scheme (Scheme 4) for the resolution of 8a, 15a and 18a.

DETAILED DESCRIPTION OF THE INVENTION

Figure 1:
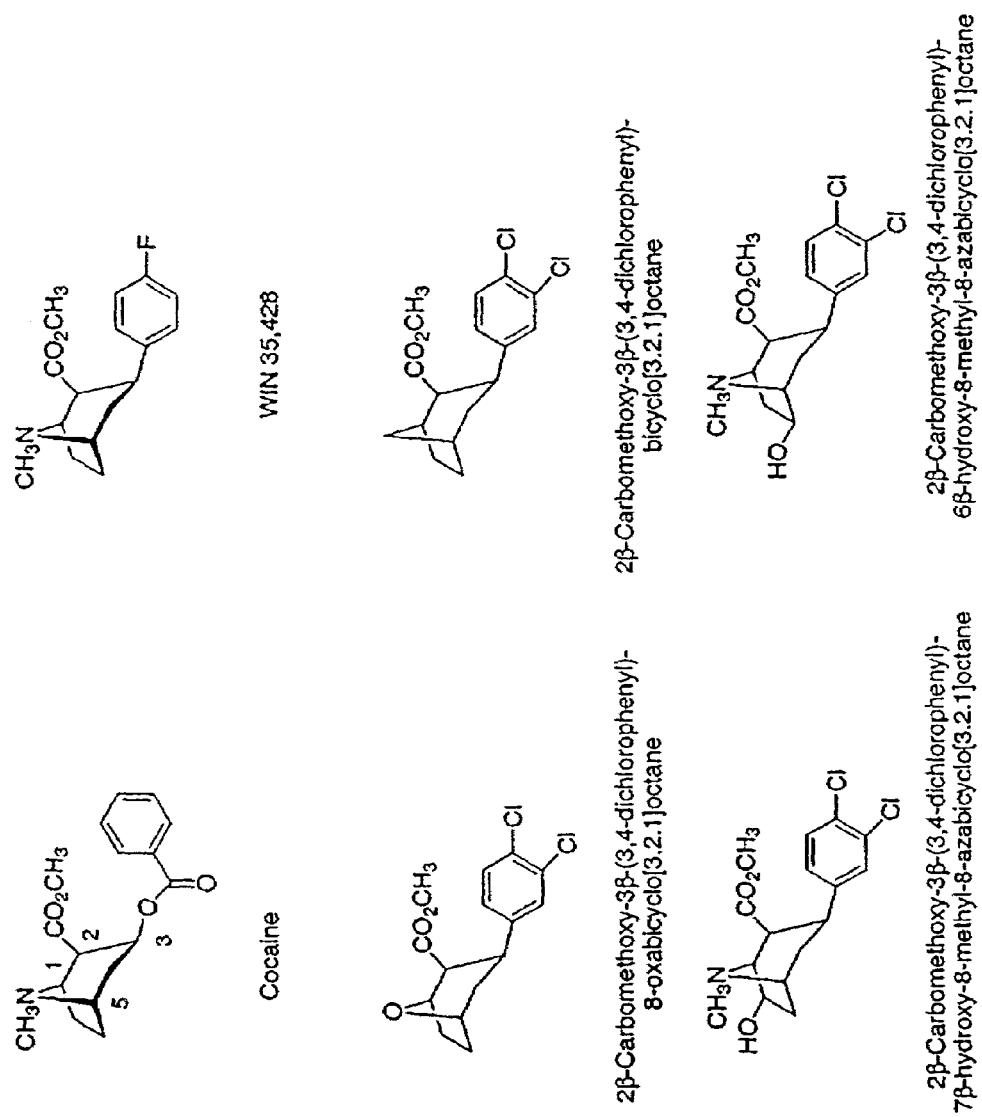
FIG. 1 illustrates the structures of Lead Bicyclo{3.2.1}octanes.

In accord with the present invention, novel tropane compounds are provided that bind to monoamine transporters, preferably the DAT. Certain preferred compounds also have a high selectivity for the DAT versus the SERT. The tropane analogs of the present invention have hydroxyl or ketone substituents in the 6- or 7-position of the tropane structure. Preferred compounds of the invention include those having the formula:

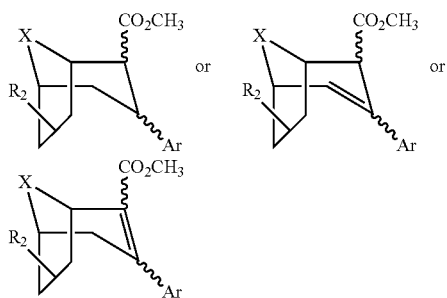

Other preferred compounds have the following formula:

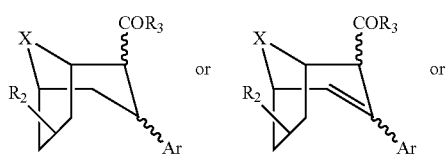

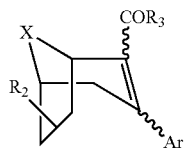

Particularly preferred compounds have X includes a nitrogen, carbon or oxygen atom as a ring member, R$_2$ is OH, and Ar is phenyl, substituted phenyl such as mono- or di-halogen substituted phenyl, or a diarylmethoxy including halogen substituted such groups.

The invention also relates to compounds having the structural formula:

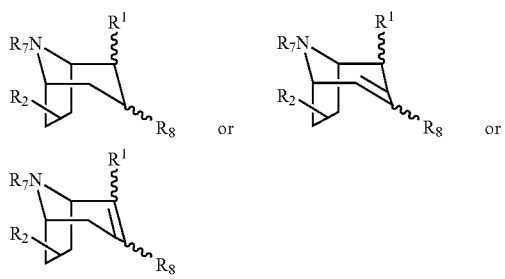

wherein:
R$_1$=COON$_7$, COR$_3$, lower alkyl, lower alkenyl, lower alkynyl, CONHR$_4$, CON(R$_7$)OR$_7$ or COR$_6$ and is α or β;
R$_2$=OR$_9$ and is a 6- or 7-substituent;
R$_3$=H, (CH$_2$)$_n$C$_6$H$_4$Y, C$_6$H$_4$Y, CHCH$_2$, lower alkyl, lower alkenyl or lower alkynyl;
R$_4$=CH$_3$, CH$_2$CH$_3$, or CH$_3$SO$_2$;
R$_6$=morpholinyl or piperidinyl;
R$_8$=camphanyl, phenyl-R$_5$, naphthyl-R$_5$, anthracenyl-R$_5$, phenanthrenyl-R$_5$, or diphenylmethoxy-R$_5$;
R$_5$=H, Br, Cl, I, F, OH, OCH$_3$, CF$_3$, NO$_2$, NH$_2$, CN, NHCOCH$_3$, N(CH$_3$)$_2$, (CH$_2$)nCH$_3$, COCK$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);
n=0, 1, 2, 3, 4 or 5;
R$_7$=lower alkyl; and R$_9$=a protecting group.

Examples of suitable groups for use as R$_2$ in these embodiments which comprise a protecting group include substituted methyl ethers where R$_9$=—CH$_3$; —CH$_2$OCH$_3$; —CH$_2$OCH$_2$C$_6$H$_5$; —CH$_2$OCH$_2$C$_6$H$_4$-4-OCH$_3$; —CH$_2$OC$_6$H$_4$-4-OCH$_3$; —CH$_2$OC(CH$_3$)$_3$; —CH$_2$OSi (C$_6$H$_5$)$_2$C(CH$_3$)$_3$; —CH$_2$OSi(CH$_3$)$_2$C(CH$_3$)$_3$; —CH$_2$OCH$_2$CH$_2$OCH$_3$; —CH—CH$_2$CH$_2$CH$_2$CH$_2$O-(tetrahydropyranylether). Other examples of suitable groups for use as R$_2$ include substituted ethyl ethers where R$_9$=—CH (OC$_2$H$_5$)CH$_3$; —C(OCH$_2$C$_6$H$_5$)(CH$_3$)$_2$; —CH$_2$CCl$_3$; —CH$_2$CH$_2$Si(CH$_3$)$_3$; —C(CH$_3$)$_3$; —CH$_2$CH=CH$_2$; —C$_6$H$_4$-4-Cl; —C$_6$H$_4$-4-OCH$_3$; —C$_6$H$_3$-2,4-(NO$_2$)$_2$; —CH$_2$C$_6$H$_5$. It can also include substituted benzyl ethers, where such as R$_9$=—CH$_2$C$_6$H$_4$-4-OCH$_3$; —CH$_2$C$_6$H$_3$-3,4-(OCH$_3$)$_2$; —C(C$_6$H$_5$)$_3$; —C(C$_6$H$_5$)$_2$C$_6$H$_4$-4-OCH$_3$ or silyl ethers, where R$_9$=—Si(CH$_3$)$_3$; —Si(CH$_2$CH$_3$)$_3$; —Si(CH (CH$_3$)$_2$)$_3$; —Si(CH$_3$)$_2$(CH(CH$_3$)$_2$); —Si(CH$_3$)$_2$(C(CH$_3$)$_3$);

—Si($C_6H_5$)$_2$(C($CH_3$)$_3$)). $R_2$ can include esters, where $R_9$=—CHO; —COCOC$_6$H$_5$; —COCH$_3$; -camphanoyl; —COC$_6$H$_5$ or also carbonates where $R_9$=—COOCH$_3$; —COOCH$_2$CH$_3$; —COOCH$_2$CCl$_3$; —COOCH=CH$_2$; —COOCH$_2$CH=CH$_2$; —COOCHY$_2$C$_6$H$_5$; —COOCH$_2$C$_6$H$_4$-4-C. One of ordinary skill in the art can readily select an appropriate protecting group. These compounds in this group are useful as intermediates in obtaining the 6- and 7-hydroxylated tropanes of the present invention. In certain preferred embodiments, $R_1$ is selected from COOR$_7$, COR$_3$, or CON(R$_7$)OR$_7$; R$_3$ is lower alkyl; R$_8$ is camphanyl or phenyl-R$_5$; R$_7$ is CH$_3$ and R$_9$ is MOM or DAD.

The 6- and 7-hydroxylated tropanes of the present invention have similar potency to their unsubstituted counterparts but unexpectedly manifest greater selectivity for the DAT. SAR in this series mimics that found in other tropanes in which 3,4-dichloro substitution generally confers greatest potency at the DAT and the unsubstituted phenyl ring at C3 is least potent. The 7-Hydroxylated compounds of the present invention are more potent at the DAT than the 6-hydoxylated counterparts. In accord with known SAR, the 3α-aryl compounds of the present invention manifest a marked selectivity for DAT inhibition. As for other tropanes, the DAT has been found to be enantioselective and the 1S-isomers of the compounds of the present invention are considerably more potent inhibitors than the 1R enantiomers. Finally, introduction of a C2-ethylketone in the present compounds, e.g. Compound 26, provides extremely potent and selective DAT inhibitors.

The route of synthesis is shown in Schemes 1, 2 and 3. The 6- and 7-hydroxy target compounds were obtained individually, however, for ease of presentation, the position of bridge substitution is not specified in the schemes. The 6- and 7-hydroxy β-keto esters 1a and 1b were prepared as described previously (Chen, Z.; Meltzer, P. C., *Tetrahedron Lett.* 1997, 38, 1121–1124; Robinson, R., *J. Chem. Soc.* 1917, 111, 762; Nedenskov, P.; Clauson-Kaas, N., *Acta Chem. Scand.* 1957, 22, 1385; Sheehan, J. C.; Bloom, B. M., *J. Am. Chem. Soc.* 1952, 74, 3825). The stereochemistry of the β-hydroxyl group at C6 (1a) or C7 (1b) was confirmed by NMR studies. Most important, a coupling constant of J=0 Hz between H-5 and H-6 (δ=4.05 ppm) in the case of 1a, and between H-1 and H-7 (δ=4.1 ppm) in the case of 1b, confirmed a dihedral angle of 90° for both compounds. This dihedral angle can only be obtained between a 6α- or 7α-oriented proton and the relevant bridgehead proton at C1 or C5 respectively. This therefore confirms the β-orientation of the hydroxy moieties in 1a and 1b. No α-hydroxy isomers were isolated.

A mixture of 6- and 7-hydroxy-β-keto esters 1a and 1b was methoxymethylated with dimethoxymethane in dichloromethane with p-toluenesulfonic acid as catalyst. Column chromatography provided regioisomers 2a and 2b which were individually utilized, as described below. The $^1$H NMR spectra of 2a and 2b, as well as pure 1a and 1b, proved quite interesting. Both compounds 1a and 2a clearly exhibit the expected (Meltzer, P. C. et al., *J. Med. Chem.* 2000, 43, 2982–2991) equilibrium distribution between the 2α-carboxy ester, enol-2-carboxy ester, and 2β-carboxy ester with the result that their $^1$H NMR spectra are quite complex. Compounds 1b and 2b surprisingly do not. In fact, in CDCl$_3$ solution, compounds 1b and 2b exist exclusively as the enol. Unequivocal evidence for this lies (as exemplified for 1b) in the complete absence of a C2 proton and the presence of a doublet at δ 1.73 (H$_{4β}$: J=18.6 Hz) and a double doublet at δ 2.76 (H$_{4α}$: J=18.6 and 4.7 Hz) integrating for fully one proton each. The enolic proton at δ 11.8 also fully integrates for one proton. The reason for this preference for the enol in the 7-substituted compounds is unclear.

Conversion of 2 to the vinyl enoltriflates 3 was achieved with sodium bis(trimethylsilyl)amide and N-phenyltrifluoromethanesulfonimide at low temperature (Keverline, K. I. et al., *Tetrahedron Lett.* 1995, 36, 3099–3102). The alkenes 4 and 5 were then obtained in good yield by Suzuki coupling (Oh-e, T. et al., *J. Org. Chem.* 1993, 58, 2201–2208) of the triflates 3 with the corresponding boronic acids. Reduction of 4 and 5 (Scheme 2) with samarium iodide at −78° C. then afforded the saturated tropane analogs 9–12 (Keverline, K. I. et al., *Tetrahedron Lett.* 1995, 36, 3099–3102). Compounds 9 and 11 were shown by $^1$H NMR to exist in a chair conformation, and 10 and 12 assumed a boat conformation. Finally, the MOM groups of each of 4, 5 and 9–12 were removed in high yield with trimethylsilyl bromide in methylene chloride at 0° C. to give the corresponding hydroxy tropanes 7 and 8 (Scheme 1), 14 and 15, and 17 and 18 (Scheme 2) respectively.

The 7-ketoesters 19 and 20 were obtained in good yield upon oxidation of 15 and 18 respectively with tetra-n-propylammonium perruthenate (Griffith, W. P. et al., *J. Chem. Soc. Chem. Commun.* 1987, 21, 1625–1627) and N-methylmorpholine-N-oxide in methylene chloride.

The 2-ethylketone analogs 23 and 26 were prepared (Scheme 3) via an intermediate Weinreb amide (Basha et al., *Tet. Lett.* 1977, 48, 4171–4174). Thus 11a was reacted with N,O-dimethylhydroxylamine and trimethyl aluminum in methylene chloride to provide the Weinreb amide 21 in high yield. Treatment with ethyl magnesium bromide in THF (Evans, D. A. et al., *J. Amer. Chem. Soc.* 1998, 120, 5921–5942) then provided the ethyl ketone 22 quantitatively. Deprotection with TMSBr yielded the target compound 23. The 3α-aryl analog 26 was obtained similarly from 12a via 24 and 25.

In order to determine the biological enantioselectivity of these hydroxytropanes, six enantiopure 7β-hydroxy-3-(3,4-dichlorophenyl) analogs were prepared. While we and others (Findlay, S. P., *J. Org. Chem.* 1957, 22, 1385–1393; Carroll, F. I. et al., *J. Med. Chem.* 1991, 34, 883–886; Meltzer, P. C. et al., *J. Med. Chem.* 1994, 37, 2001–2010) have had substantial success in recrystallization of diastereomeric tartrate salts of keto esters such as 1b, we were unable to obtain material of satisfactory enantiomeric excess (ee) with the bridge hydroxyl group present. We therefore elaborated two resolution routes, both of which relied upon the establishment of diastereomeric camphanate esters (Scheme 4). The routes had the added advantage of allowing quantification of ee by $^1$H NMR analysis (vide infra). Thus, the MOM protected keto ester 2b was reacted with (1'S)-(−)-camphanic chloride to obtain a mixture of diastereomers that could not be separated by column chromatography. Multiple recrystallizations yielded a sufficient amount of the (1R, 1'S) diastereomer 27 only. Pure (1S,1'S) diastereomer could not be obtained by these means. Hydrolysis of (1R)-27 with lithium hydroxide then provided enantiopure keto ester (1R)-2. This keto ester was then taken through the same synthetic pathway as shown for racialmates 1b (Schemes 1 and 2) to obtain the enantiopure (1R)-8a, (1R)-15a, and (1R)-18a.

This approach provided only the 1R-tropanes. Therefore an alternate approach was also developed. (Scheme 4). The racemic 2,3-ene 8a was esterified with (1'S)-(−)-camphanic chloride to obtain a diastereomeric mixture 28 which was purified by column chromatography to obtain (1S,1'S)-28. Hydrolysis with LiOH then provided the enantiopure target compound (1S)-8a which was reduced with SmI$_2$ to obtain the 3β (1S)-15a and 3α (1S)-18a target compounds. Physical data relating to these six compounds are presented in Table 1.

TABLE 1

Physical Data for Six Enantiopure Analogs

| Compound | Mp ° C. | X-ray[a] | $\{\alpha\}^{21}{}_D$ |
|---|---|---|---|
| (1R)-8a | 129.0–131.0 | (1R) | +57° |
| (1R)-15a | 186.0–187.0 | | −26° |
| (1R)-18a | 149.0–150.0 | (1R) | +47° |
| (1R)-8a | 130.4–132.4 | | −58° |
| (1R)-15a | 185.5–186.5 | | +25° |
| (1R)-18a | 148.5–150.0 | (1S) | −48° |

[a]X-ray crystallographic analysis confirmed stereochemical assignments

Each enantiomeric pair had equal and opposite optical rotations. Since this is an unreliable measure of enantiomeric excess, an NMR method was developed. Each of the six compounds was obtained in >98% ee as confirmed by $^1$H NMR. In this regard, NMR spectra of the camphanate esters are unequivocal since one of the camphanate methyl resonances for the (1R,1'S) and (1S,1'S) compounds is base-line separated and can therefore be quantified reliably. Thus the (1R)-27 manifests a methyl group at δ 0.99. The (1S)-27 shows the same methyl at δ 1.02. Absolute stereochemistry was assigned by X-ray crystallographic analysis for (1R)-8a, (1R)-18a, and (1S)-18a. This allowed confident stereochemical assignment of the remaining compounds.

It should be noted that the designation of chirality for these bridge-hydroxylated tropanes is reversed from that of the bridge unsubstituted parent compounds. This is a result of the rules for nomenclature and does not reflect a difference in absolute stereochemistry. Thus the more potent enantiomers here are the 1S designated compounds in contrast to the 1R active enantiomers of the parent compounds 6a, 13a, or 16a.

Inversion of the bridge hydroxyl group in 17a and 18a was effected (Scheme 5) in two steps by straightforward Mitsunobu chemistry (Mitsunobu, O., Synthesis 1981, 1–28). Thus the 6β-hydroxy 17a was reacted with benzoic acid and triphenylphosphine in the presence of diethylazodicarboxylate to give 29a. The benzoyl group was then removed with LiOH/THF to provide the 6α-hydroxy analog 30a The 7β-hydroxy analog 18a was treated similarly to obtain 30b.

The $^1$H NMR spectra of these inverted compounds are interesting in that the α-oriented hydroxyls have a surprisingly large through space compression effect on the axial protons at H2α in the case of the 7-OH compound 30b and at H4α in the case of the 6α-hydroxy compound 30a. Such effects have been observed previously in epibatidine analogs (Fletcher, S. R. et al., J. Org. Chem. 1994, 59, 1771–1778). Boat versus chair conformation of bicyclo{3.2.1}octanes has always been assigned on the basis of $^1$H NMR, and the signal corresponding to H4α in 2β-substituted-3α-arylbicyclo{3.2.1}octanes has been particularly diagnostic. It generally appears as a double double doublet at δ 1.3 showing large geminal coupling interactions with H4β (ca. 14 Hz) and H3 (trans-diaxial coupling ca. 11 Hz) and a small coupling constant with H5 (ca. 2 Hz). That is the case for the 2β-carbomethoxy-3α-(3,4-dichlorophenyl)hydroxylated derivatives when the hydroxyl group is in the 6β (17a), 7β (18a), or 7α (30b) orientation (in the latter case obscured by the presence of a signal corresponding to H6β). In the case of the 6α-hydroxy derivative 30a, the signal corresponding to H4α was observed at δ 2.15 (Δ=0.85 ppm) (with the appropriate multiplicity described above) due to the strong 1,4-diaxial interaction with the 6α-OH. A similar displacement (Δ=0.9 ppm) was observed in the signal corresponding to H2α in the 7α-hydroxy compound, 30b. Finally the $^1$H NMR spectrum of the 7-keto compound 20 showed a strong resemblance with the hydroxy analog's spectra, although the signal corresponding to H4α appeared at lower fields (δ 1.51) and the trans-diaxial coupling interactions H3-H2 and H3-H4α were slightly weaker than expected (J=8 Hz). These minor differences indicate a pseudo boat conformation.

The diarylmethoxy compounds (Scheme 6) 32a and 32b were obtained from the MOM protected keto esters 1a and 1b. Reduction with sodium borohydride gave the 3α-hydroxy compounds 31. Subsequent reaction with 4,4'-difluorobenzhydrol in methylene chloride with p-toluenesulfonic acid provided 32a or 32b directly.

Figure 2:
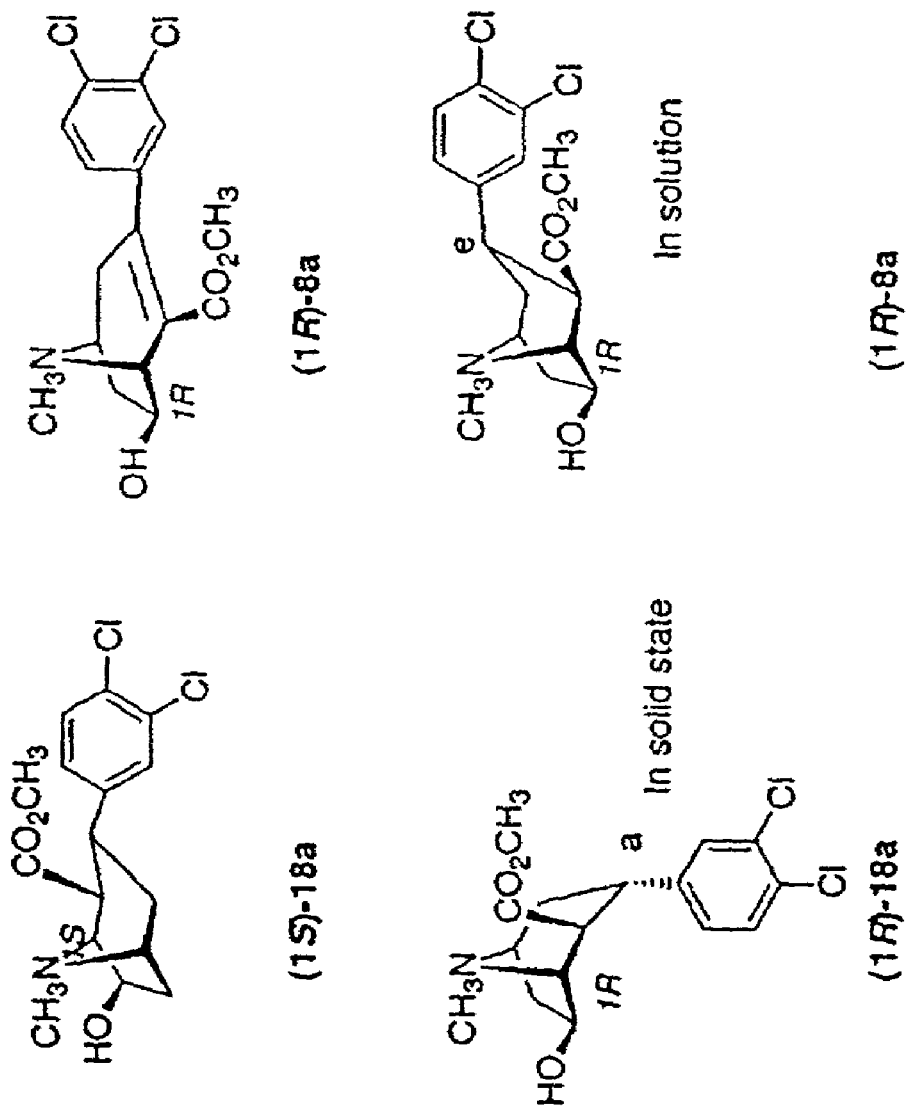
Figure 3:
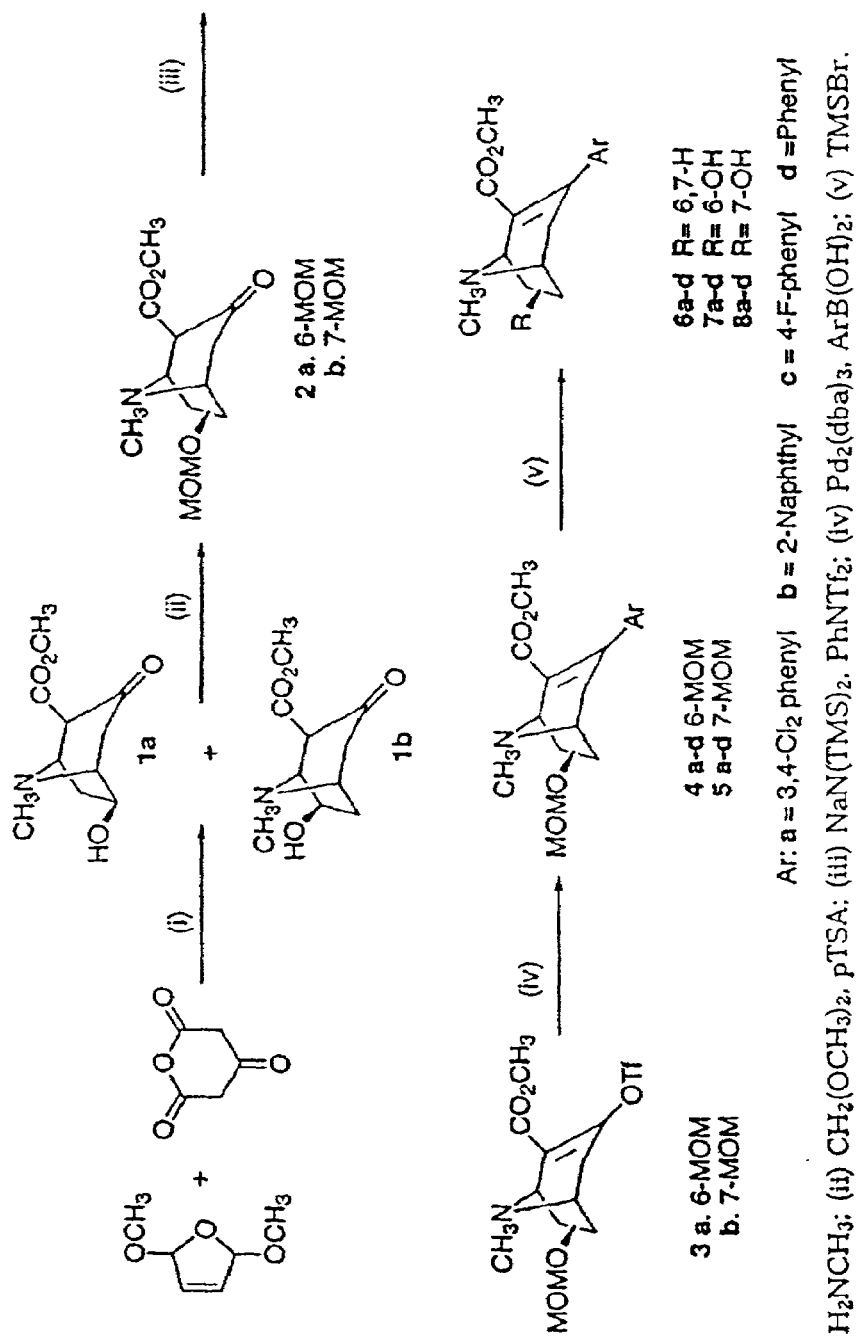
FIG. 3 illustrates a reaction scheme (Scheme 1) for the preparation of 2,3-Unsaturated Tropanes.
Figure 4:
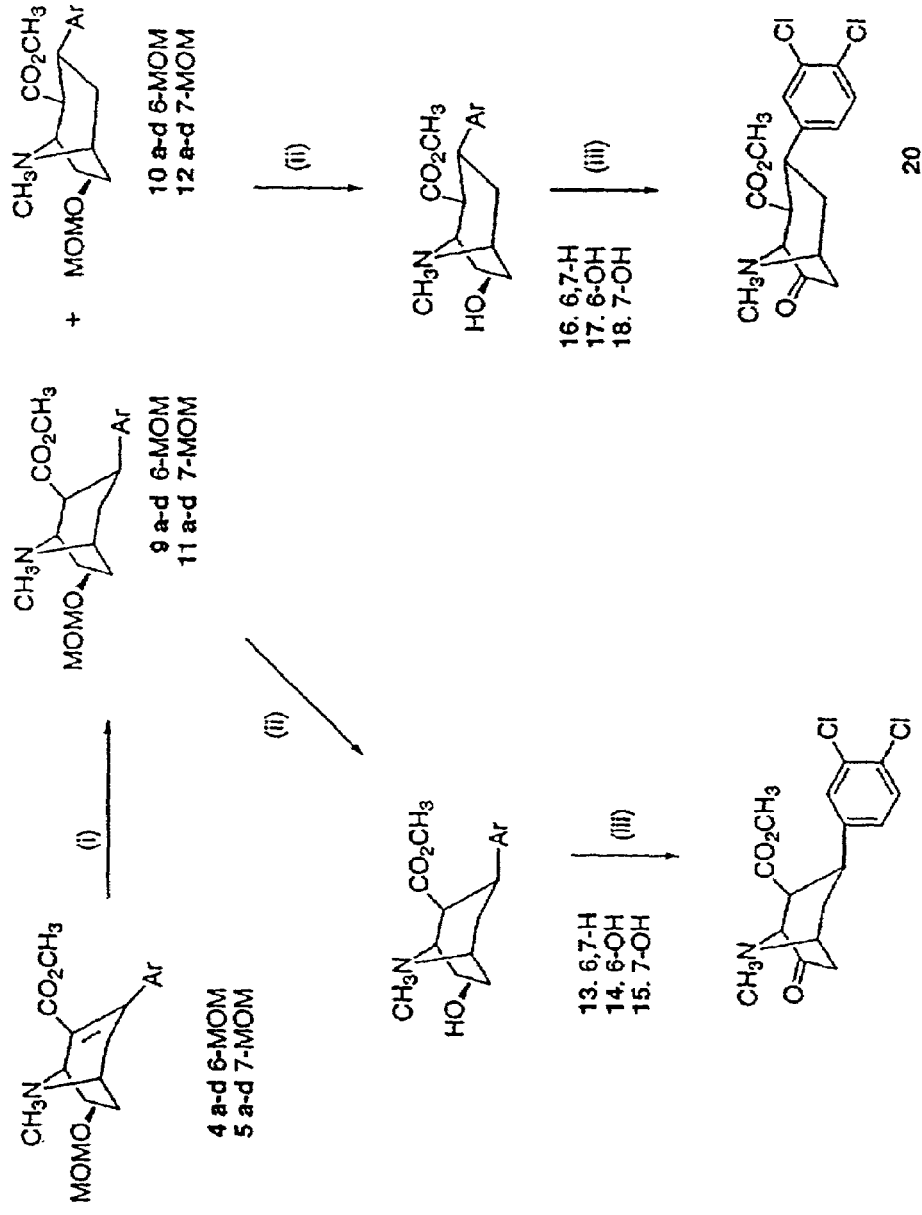
FIG. 4 illustrates a reaction scheme (Scheme 2) for the preparation of Bridge Oxygenated Tropanes.
Figure 5:
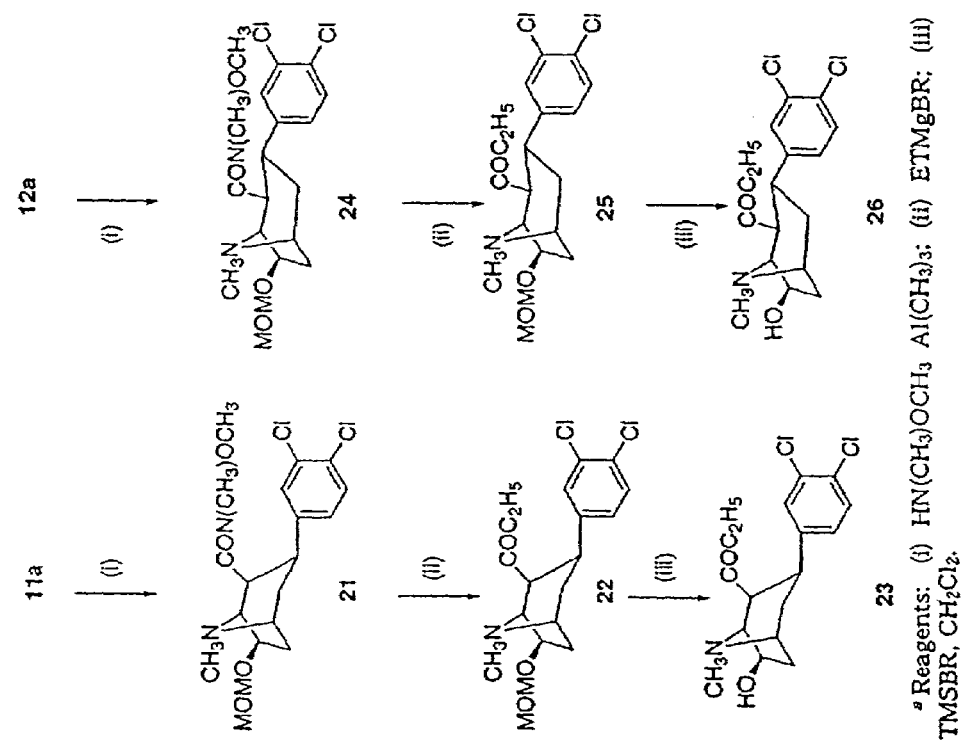
FIG. 5 illustrates a reaction scheme (Scheme 3) for the preparation of Bridge Oxygenated 2-Keto Tropanes.
Figure 6:
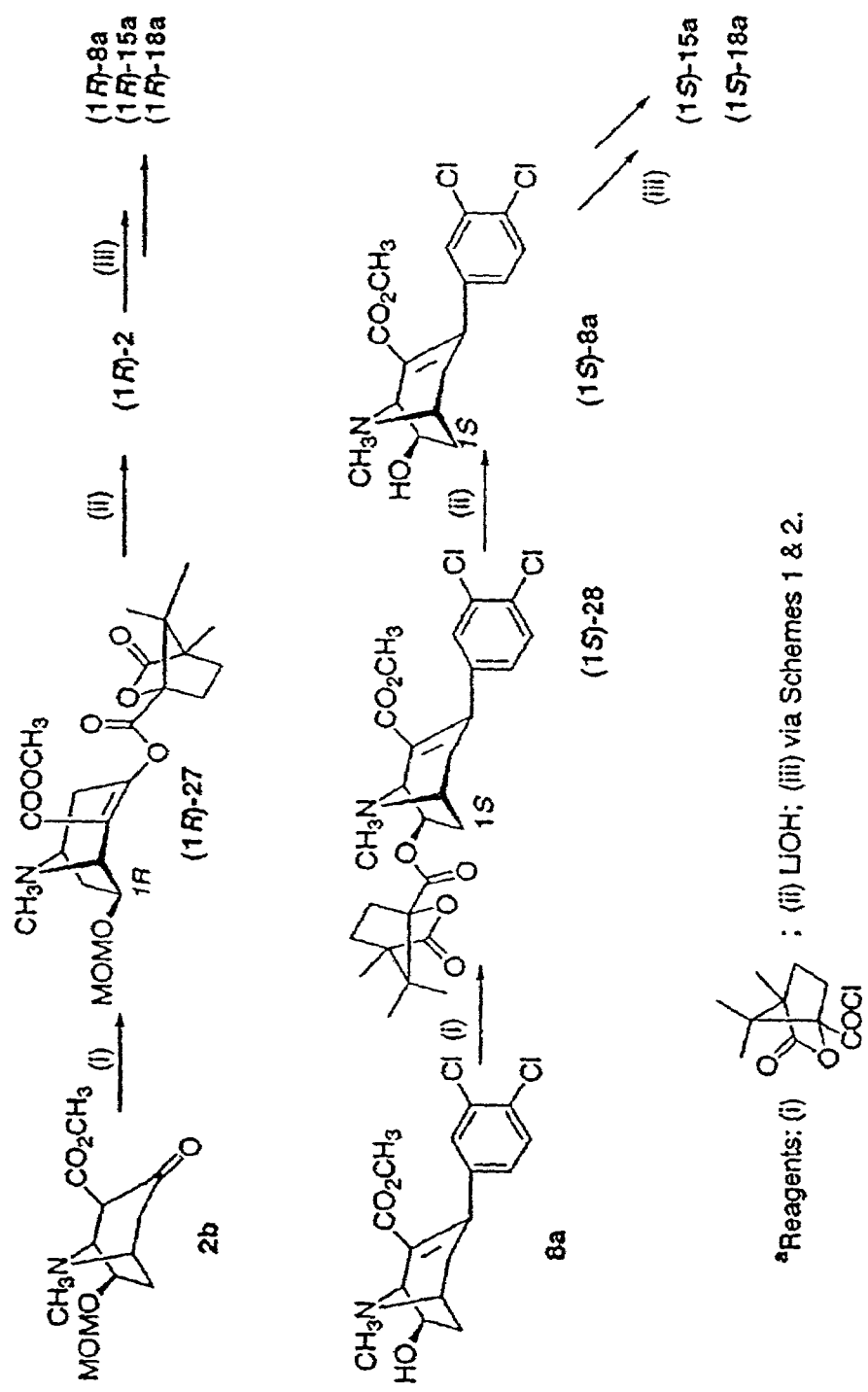
Figure 7:
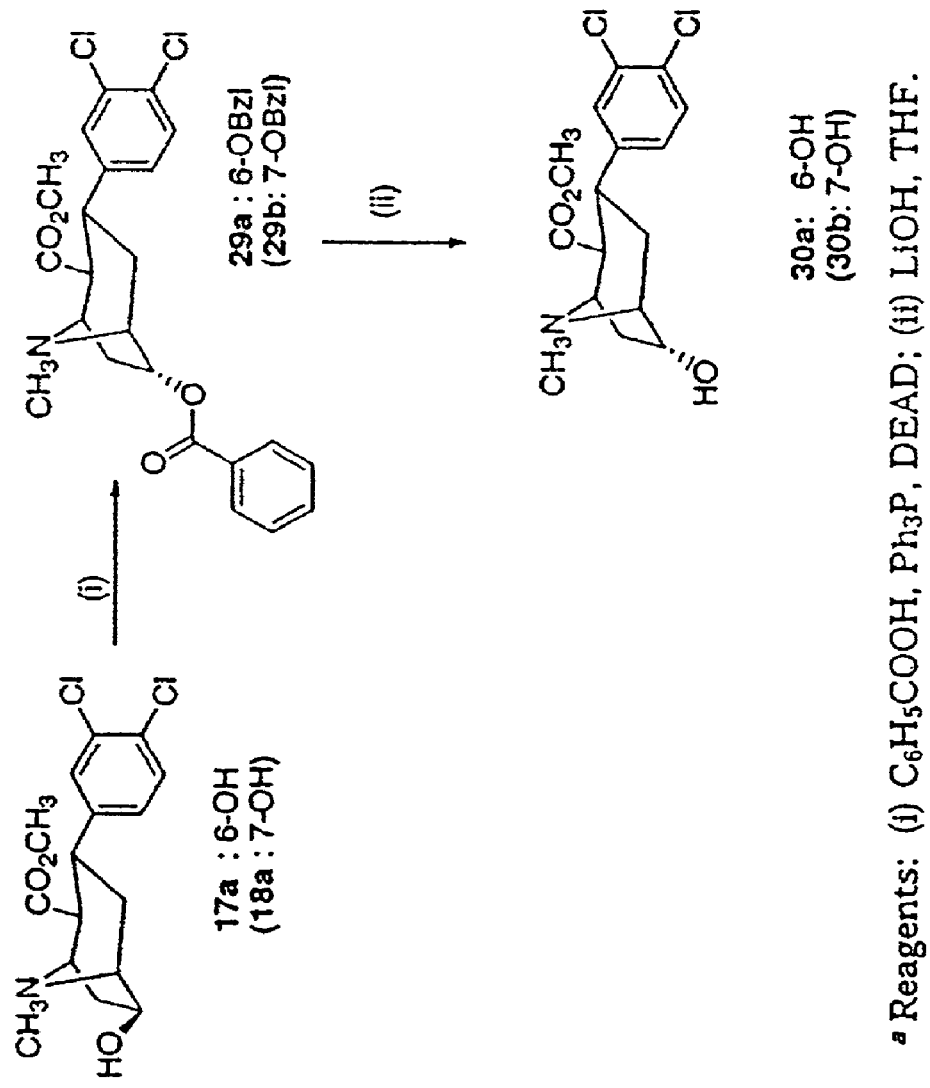
FIG. 7 illustrates a reaction scheme (Scheme 5) for the inversion at C6 and C7.
Figure 8:
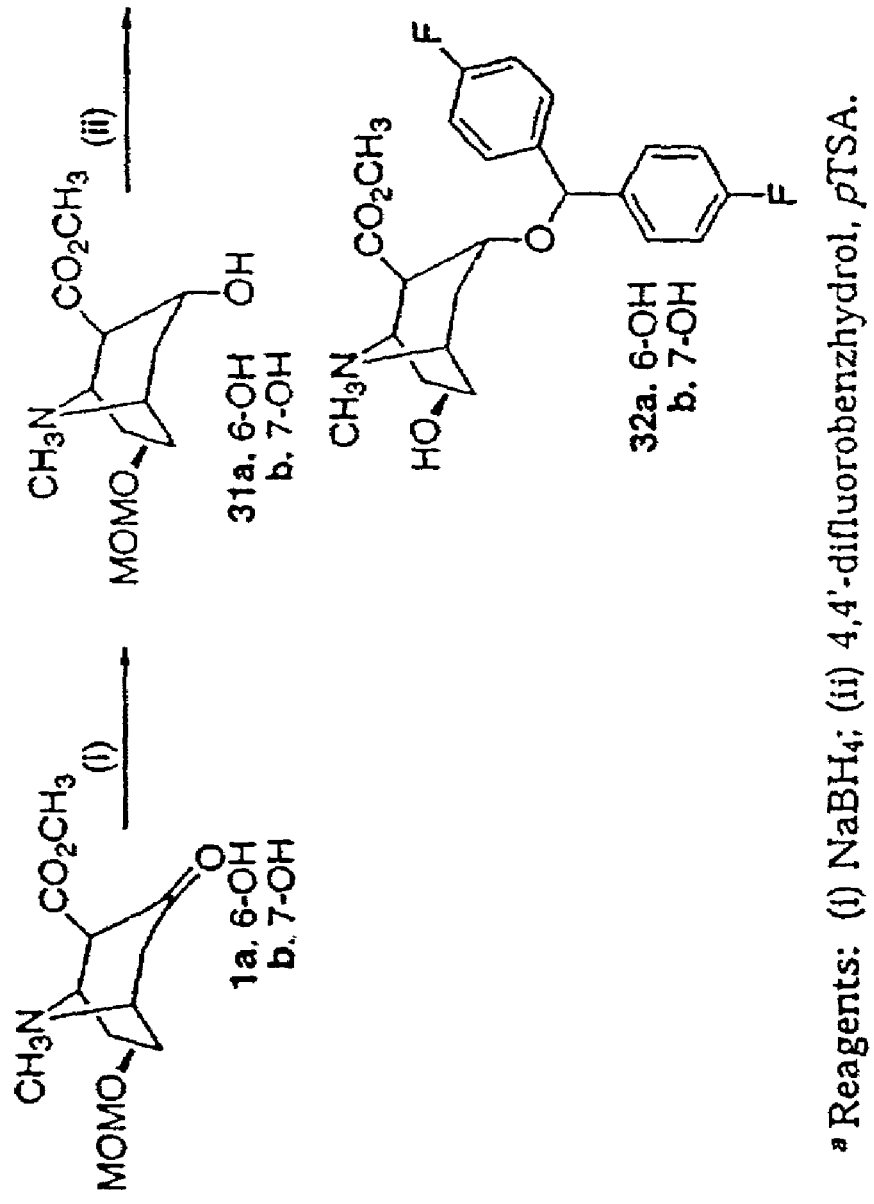
FIG. 8 illustrates a reaction scheme (Scheme 6) for the preparation of Diarylmethoxy Tropanes.

In order to assign absolute stereochemistry for those compounds that were prepared in enantiomerically pure form, X-ray structural analyses were conducted. Compounds (1R)-8a, (1R)-18a, and (1S)-18a were recrystallized from methylene chloride/pentane to obtain suitable crystals. Compound (1S)-18a was thus demonstrated to be the 1S-enantiomer. Compound (1R)-18a was proved to be 1R, and compound (1R)-8a, the precursor to (1R)-18a, was likewise confirmed as 1R (FIG. 2). A comparison of the conformation established by $^1$H NMR studies in solution (CDCl$_3$) with that evident in the solid state as evidenced by X-ray crystallography proved interesting. While both 3α-aryl enantiomers adopted a boat conformation in solution, the 1R enantiomer (1R)-18a presented in chair conformation in the solid state. Among the numerous X-ray crystallographic structural determinations that we have conducted on tropanes, (1R)-18a represents the first instance in which the conformation in the solid state is markedly different from that in solution. This is highly unlikely to be a consequence of enantiomeric differences ((1R)-18a vs. (1S)-18a). However, this difference is potentially important since a chair conformation would place the 3α-aryl substituent in an axial position. SAR studies have taken into consideration that a 3β-substituent, which favors the chair conformation of the bicyclo{3.2.1}octane system, places the 3-aryl group in an equatorial position. Further, the 3α-aryl compounds have, on the basis of NMR studies and all prior X-ray studies, been shown to adopt a boat conformation in which the C3-aryl group is again oriented equatorially. This contrast between the crystal conformation of (1S)-18a (boat) as compared with that of its enantiomer (1R)-18a (chair) is probably fortuitous. It was noted that the unit cell structures for (1R)-18a and (1S)-18a differed with respect to intermolecular hydrogen bonding. It appeared that (1S)-18a manifested H-bonding between the 7-OH and the 7-OH of an adjacent molecule, while (1R)-18a manifested H-bonding between a 7-OH and an 8-N of an adjacent molecule. $^1$H NMR experiments were conducted to examine the possible influence of such intermolecular hydrogen bonding upon conformation. The conformation of the 3α-molecule (1S)-18a in CDCl$_3$ solution is pseudo-boat (evidenced by the double double doublet resonances for H$_{4\alpha}$ at δ 1.24). It maintains this conformation in CD$_3$OD/D$_2$O (H$_{4\alpha}$ ddd at δ 1.3) or CD$_3$OD/H$_2$O (H$_{4\alpha}$ ddd at δ 1.3) under a water suppression protocol. Therefore intermolecular hydrogen bonding does not favor chair conformation over the boat for this compound. This result highlights the caution that should be exercised as one extrapolates from a three dimensional crystal structure to a putative three-dimensional structure within the biological system.

The affinities ($IC_{50}$) for the dopamine and serotonin transporters were determined in competition studies. The dopamine transporter was labeled with {$^3$H}3β-(4-fluorophenyl)tropane-2β-carboxylic acid methyl ester ({$^3$H}WIN 35,428 or {$^3$H}CFT (1 nM)) and non-specific binding was measured with (−)-cocaine (30 μM) (Madras, B. K. et al., *J. Pharmacol. Exp. Ther.* 1989, 251, 131–141). {$^3$H}Citalopram was used to label the serotonin transporter and non-specific binding was measured with fluoxetine(10 μM) (Madras, B. K. et al., *Synapse* 1996, 24, 340–348). Binding data for the 2-carbomethoxy-6- or 7-hydroxy compounds are presented in Table 2. Table 2 shows the inhibition of {$^3$H}WIN 35,428 binding to the dopamine transporter and {$^3$H}citalopram binding to the serotonin transporter in rhesus (mucaca mulata) or cynomolgus monkey (macaca fasicularis) caudate-putamen. Each value is the mean of 2 or more independent experiments each conducted in different brains and in triplicate. Errors generally do not exceed 15% between replicate experiments. Highest doses tested were generally 10–100 μM.

Table 3 presents binding data for the 7-keto, 6α- and 7α-hydroxy, and 3-diarylmethoxy compounds. Table 3 shows the inhibition of {$^3$H}WIN 35,428 binding to the dopamine transporter and {$^3$H}citalopram binding to the serotonin transporter in rhesus or cynomolgus monkey caudate-putamen. Studies were conducted in monkey striatum because this tissue (Meltzer, P. C. et al., *Med. Chem. Res.* 1998, 8, 12–34) is used in an ongoing investigation of structure activity relationships at the DAT, and meaningful comparisons with an extensive database can be made. Competition studies were conducted with a fixed concentration of radioligand and a range of concentrations of the test drug. All drugs inhibited {$^3$H}WIN 35,428 and {$^3$H}citalopram binding in a concentration-dependent manner. Each value is the mean of 2 or more independent experiments each conducted in different brains and triplicate. Errors generally do not exceed 15% between replicate experiments. Highest doses tested were generally 10–100 μM.

TABLE 2

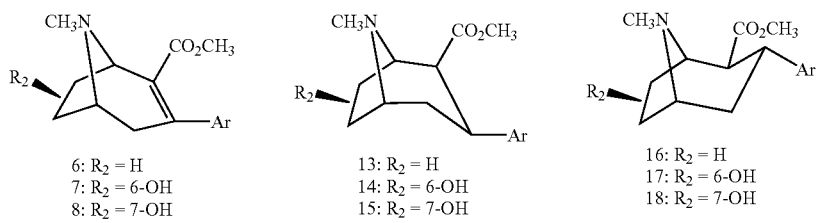

6: $R_2$ = H
7: $R_2$ = 6-OH
8: $R_2$ = 7-OH

13: $R_2$ = H
14: $R_2$ = 6-OH
15: $R_2$ = 7-OH

16: $R_2$ = H
17: $R_2$ = 6-OH
18: $R_2$ = 7-OH

Ar: a = 3,4-Cl$_2$ phenyl  b = 2-Naphthyl  c = 4-F-phenyl  d = Phenyl

| $R_2$ | Compound | $IC_{50}$ (nM) DAT | SERT | SERT/DAT | Compound | $IC_{50}$ (nM) DAT | SERT | SERT/DAT |
|---|---|---|---|---|---|---|---|---|
| H    | 6a, O-1109       | 1.16     | 867      | 747  | 13a, O-401 (R)   | 1.09  | 2.47    | 2    |
| 6-OH | 7a, O-1591       | 55.1     | 3,320    | 60   | 14a, O-1299      | 3.02  | 166     | 55   |
| 7-OH | 8a, O-1813       | 19.4     | >6,000   | >300 | 15a, O-1164      | 1.42  | 27.7    | 20   |
| 7-OH | (1R)-8a, O-1677  | 265      | 1,590    | 6    | (1R)-15a, O-1675 | 2,690 | 139     | 0.05 |
| 7-OH | (1S)-Sa, O-1923  | 7.37     | 5,370    | 730  | (1S)-15a, O-1945 | 0.3   | 15      | 50   |
| H    | 6b, O-1173       | 2.94     | 109      | 37   | 13b, O-1229 (R)  | 0.49  | 2.19    | 5    |
| 6-OH | 7b, O-1627       | 246      | 260      | 1    | 14b, O-1814      | 7.7   | 34.2    | 4    |
| 7-OH | 8b, O-1815       | 45       | 677      | 15   | 15b, O-1981      | 1.26  | 5.57    | 4    |
| H    | 6c, O-1104       | 408      | 7,990    | 20   | 13c, O-381 (WIN) | 11.0  | 160     | 15   |
| 6-OH | 7c, O-1588       | >20,000  | >20,000  | 1    | 14c, O-1817      | 477   | >20,000 | >42  |
| 7-OH | 8c, O-1927       | 7,730    | >10,000  | 1    | 15c, O-1983      | 123   | >10,000 | >80  |
| H    | 6d, O-1449       | 2,590    | 28,600   | 11   | 13d              | 65    | NA      | —    |
| 6-OH | 7d, O-1644       | >150,000 | >100,000 | 1    | 14d, O-1816      | 6,150 | 88,000  | 14   |
| 7-OH | 8d, O-1944       | >10,000  | >10,000  | 1    | 15d, O-1953      | 235   | >10,000 | >43  |

| $R_2$ | Compound | $IC_{50}$ (nM) DAT | SERT | SERT/DAT |
|---|---|---|---|---|
| H    | 16a, O-1157 (R)  | 0.38  | 27.7     | 73    |
| 6-OH | 17a, O-1926      | 6.09  | 1,450    | 238   |
| 7-OH | 18a, O-1163      | 1.19  | 1,390    | 1,170 |
| 7-OH | (1R)-18a, O-1676 | 482   | 5,300    | 11    |
| 7-OH | (1S)-18a, O-1924 | 0.76  | 1,220    | 1,610 |
| H    | 16b, O-1228      | 0.57  | 5.95     | 10    |
| 6-OH | 17b, O-1748      | 32    | 180      | 6     |
| 7-OH | 18b, O-1952      | 2.8   | 94       | 34    |
| H    | 16c, O-1204      | 17.9  | 1,130    | 63    |
| 6-OH | 17c, O-1755      | 739   | 5,820    | 8     |
| 7-OH | 18c, O-1951      | 110   | >20,000  | >120  |
| H    | 16d              | NA    | NA       | —     |
| 6-OH | 17d, O-1589      | 3,530 | >10,000  | >3    |
| 7-OH | 18d, O-1954      | 518   | >100,000 | >190  |

TABLE 3

| Compound | | IC$_{50}$ (nM) DAT | IC$_{50}$ (nM) SERT | Compound | | IC$_{50}$ (nM) DAT | IC$_{50}$ (nM) SERT |
|---|---|---|---|---|---|---|---|
| 19 | O-2097 | 14.1 | 290 | 30b | O-2032 | 3.04 | 991 |
| 20 | O-2096 | 14.2 | 7,038 | 32a | O-2070 | 448 | 4,850 |
| 23 | O-2074 | 0.81 | 97 | 32b | O-2031 | 6,300 | 9,560 |
| 26 | O-2099 | 1.1 | 2,520 | 33[a] | O-2016 | 48 | 533 |
| 30a | O-2015 | 33.2 | 10,700 | 34[b] | O-1754 | 32,600 | >20,000 | a.

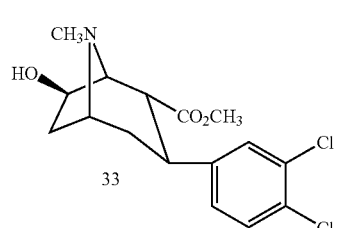

b.

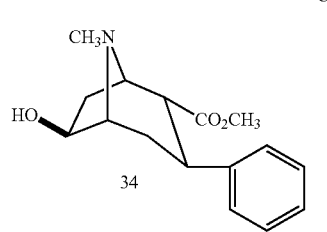

The bridge-hydroxylated compounds of the present invention provide a broad array of molecules including compounds that bind with very high affinity. Selectivity for inhibition of the DAT versus the serotonin transporter (SERT) is another property of tropanes of considerable relevance for development of medications and for probes useful to image the DAT in living brain. Preferred compounds for DAT imaging agents have high DAT:SERT selectivity.

The compounds of the present invention can exhibit extremely potent and selective binding for the DAT. Preferred compounds of the present invention exhibit the desired target:non-target (DAT:SET) specificity. Preferably, the selectivity ratio of binding of SERT to binding of DAT is greater than about 10, preferably greater than about 30 and more preferably 50 or more.

In addition, the compounds are potent, having an IC$_{50}$ less than about 500 nM, preferably less than 60 nM, more preferably less than about 20, and most preferably less than about 10.

Using the combination of selectivity (SERT/DAT ratio) and potency (IC$_{50}$) information for these compounds, one of ordinary skill in the art can readily select the appropriate compound for the desired application, e.g., imaging or treatment.

For example, for cocaine medications high DAT:SERT selectivity may not be necesary. Even though the parent compound cocaine is relatively non-selective for all three monoamine transporters, and an abundance of evidence suggests that DAT blockade is a significant contributor to the reinforcing effects of cocaine, self-administration is sustained in DAT knockout mice (Rocha, B. A. et al., *Nat. Neurosci.* 1998, 1 (2), 132–137). One possible interpretation of these findings is that cocaine blocks transport of dopamine via other transporters in brain regions critical to maintaining self-administration (Sora, I. et al., *Proc. Natl. Acad. Sci. USA* 1998, 95, 7699–7704). Thus, compounds both selective and non-selective for the DAT should be assessed in screening programs for cocaine medications. The methods of the present invention enable the design of bridge-substituted tropanes with either a high or low degree of DAT:SERT selectivity.

Introduction of functionality at the 6,7-bridge of 3-phenyltropanes has been studied (Chen, Z. et al., *J. Med. Chem.* 1996, 39, 4744–4749; Lomenzo, S. A. et al., *J. Med. Chem.* 1997, 40, 4406–4414; Simoni, D. et al., *J. Med. Chem.* 1993, 36, 3975–3977; Chen, Z.; Meltzer, P. C., *Tetrahedron Lett.* 1997, 38, 1121–1124; Lomenzo, S. A. et al., *Med. Chem. Res.* 1998, 8, 35–42). In general, steric bulk at either position has reduced the affinity of these compounds for the dopamine transporter. Simple introduction of an hydroxyl group on a 3-aryl tropane is also not sufficient to provide potent DAT inhibitors (Zhao, L.; Kozikowski, A. P., *Tet. Lett.* 1999, 40, 7439). Based upon the SAR that we have uncovered in other bicyclo{3.2.1}octane series (Meltzer, P. C. et al., *J. Med. Chem.* 1997, 40, 2661–2673; Meltzer, P. C. et al., *Med. Chem. Res.* 1998, 8, 12–34), in order to achieve high potency and selectivity, the methods of the present invention use derivatives of the 3,4-dichlorophenyl substituted template as the starting point, since this substitution, and to a similar extent the 2-naphthyl substitution (Davies, H. M. L. et al., *J. Med. Chem.* 1994, 37, 1262–1268), have provided among the most potent DAT inhibitors. Furthermore, SAR studies have demonstrated that selectivity of binding to the DAT versus binding to the SERT can be obtained in the 3α-aryl as well as the 2,3-unsaturated series of compounds (Meltzer, P. C. et al., *Med. Chem. Res.* 1998, 8, 12–34).

Table 2 presents the 6- and 7-hydroxylated compounds as well as the bridge unsubstituted ($R_2$=H) parent compounds for comparison. In general, the 7-hydroxy compounds (8, 15, 18) are more potent than the 6-hydroxy compounds (7, 14, 17). Comparison of the 2,3-unsaturated racemates, 6a with 7a and 8a show that the unsubstituted compound 6a is significantly more potent than either 7a or 8a. When only active enantiomers are compared, it is apparent that the hydroxylated analogs are of comparable potencies to the bridge unsubstituted compounds. Compound (1R)-13a exhibits DAT IC$_{50}$=1.09 nM while the active (1S) -15a is about three times more potent (0.3 nM) and 25-fold more selective than 13a (Table 3).

When the aromatic ring is oriented in the 3α-configuration, the parent-unsubstituted compound (1R)-16a has DAT IC$_{50}$=0.38 nM and the hydroxylated enantiopure compound (1S)-18a shows a similar value of 0.76 nM. In this case, the hydroxylated compound shows a selectivity ratio of 1610 and is therefore 22-fold more selective than 16a. However, (1S)-18a is 32-fold more selective than (1S)-15a thus demonstrating the enhanced selectivity of 3α-configured compounds over their 3β-counterparts. Thus, introduction of an hydroxyl at C7 has, at least, maintained potency of DAT inhibition and retained or may have increased selectivity versus inhibition of the SERT.

This increase in selectivity is evident in the 6-hydroxy compounds 14a and 17a as well. The fact that the 1R configured compounds (1R) -8a, (1R)-15a and (1R)-18a are considerably less potent than the 1S enantiomers points, once again, to the biological enantioselectivity of the DAT and SERT.

The results show three properties of the compounds of the present invention. First, the bridge hydroxylated compounds confirm biological enantioselectivity. Second, the 7-hydroxylated compounds are more potent at the DAT than their 6-hydroxyl counterparts. Third, the bridge hydroxylated compounds are more selective DAT inhibitors than the unsubstituted analogs.

The effects of substitution on the C3-aryl ring of the bridge hydroxylated compounds in Table 2 mimic other tropane series (Meltzer, P. C. et al., *Med. Chem. Res.* 1998, 8, 12–34; Meltzer, P. C. et al., *J. Med. Chem.* 1993, 36, 855–862) including the 8-oxa (Meltzer, P. C. et al., *J. Med. Chem.* 1997, 40, 2661–2673) and 8-carba (Meltzer, P. C. et al., *J. Med. Chem* 2000, 43, 2982–2991) compounds. Thus, for substituents on the C3-position, 3,4-dichlorophenyl compounds are more potent inhibitors of the DAT than the 3-(2-naphthyl) compounds, which are more potent than the 3-fluorophenyl, which in turn are more potent than phenyl compounds.

Further, selectivity for inhibition of the DAT versus the SERT is greater for the compounds of the present invention bearing a 3α-aryl substituent as compared with a 3β-aryl substituent. Thus, certain preferred compounds have a 3α-aryl substituent, i.e., they are in the boat comformation.

The 2,3-unsaturated analogs generally display the same rank order of potency at the DAT. They manifest poop selectivity, particularly for those compounds that are potent inhibitors. Thus for both 6- and 7-hydroxylated compounds, 3,4-dichloro substitution provides similar or slightly higher potency at the DAT than for introduction of a C3-(2-naphthyl) group. Both are significantly superior to a 4-fluoro group which, in turn, is more potent than the unsubstituted phenyl ring compound. In the 7-hydroxy series, the racemic 3β-configured 3,4-dichloro compound 15a manifests a DAT $IC_{50}$ of 1.42 nM compared with 1.26 nM for the 2-naphthyl 15b, 123 nM for the 4-fluoro 15c, and 235 nM for the unsubstituted 15d. A similar relationship is seen in the 3α-configured series: 18a (3,4-dichloro)>18b (2-naphthyl) >18c (4-fluoro)>18d (H) and the 2,3-enes: 8a (3,4-dichloro) >8b (2-naphthyl)>8c (4-fluoro)>8d (H). Interestingly, either 6- or 7-hydroxy substituents reduce affinity of 4-fluoro substitution.

Selectivity for inhibition of the DAT versus the SERT is likewise similar to that evidenced in all other series (Meltzer, P. C. et al., *J. Med. Chem.* 1997, 40, 2661–2673; Meltzer, P. C. et al., *J. Med. Chem.* 2000, 43, 2982–2991; Meltzer, P. C. et al., *Med. Chem. Res.* 1998, 8, 12–34). The parent compounds in which no bridge hydroxylation is present (6, 13, 16) model the series (Table 2): 2,3-ene (6a)>3α (16a)>3β (13a). Thus, the 3β configured compounds are generally least selective and the 2,3-ene and 3α-compounds are more selective. This difference in selectivity diminishes where compounds are intrinsically less potent DAT inhibitors. An example of this is evident in the comparison between the potent 3,4-dichloro series and the weak ring-unsubstituted compounds. Thus 8a, 15a, and 18a have selectivities of SERT/DAT ranging from 20 to 1,170 while the unsubstituted 8d, 15d, and 18d have selectivities that range from 1–190. While the inventors do not wish to be bound by theory, it may be concluded that a tight fit between the ligand and the relevant transporter enhances selectivity.

As noted in earlier work (Meltzer, P. C. et al., *Med. Chem. Res.* 1998, 8, 12–34), the SERT appears to be more discriminating since DAT inhibition is often similar across the C3-altered compounds in contrast to SERT inhibition which differs markedly across the series. Similarly 20 and 26 (3α) are more selective than 19 and 23 (3β) (Table 3).

From these data it may be concluded that: First, the general SAR of the tropanes is maintained in that the rank order of substitution at the C3 position remains 3,4-dichlorophenyl>2-naphthyl>4-fluorophenyl>phenyl. Second, the general SAR of the bicyclo{3.2.1}octane series is maintained in that the 3α-aryl compounds are more selective than the 3β-aryl compounds.

The DAT is enantioselective (Reith, M. E. A. et al., *Biochem. Pharmacol.* 1986, 35, 1123–1129; Ritz, M. C. et al., *Science* 1987, 237, 1219–1223; Madras, B. K. et al., *J. Pharmacol. Exp. Ther.* 1989, 251, 131–141; Meltzer, P. C. et al., *J. Med. Chem.* 1994, 37, 2001–2010; Sershen, H. et al., *Neuropharmacology* 1980, 19, 1145–1148; Carroll, F. I. et al., *J. Med. Chem.* 1992, 35, 969–981; Carroll, F. I. et al., in *Drug Design for Neuroscience*; A. P. Kozikowski, Ed.; Raven Press, Ltd. New York, 1993; 149–166). Accordingly, the biological enantioselectivity of the most active parent bridge hydroxylated compounds, namely 8a, 15a, and 18a was studied. Table 2 shows that the 1S enantiomers are significantly more potent inhibitors than their 1R counterparts. Thus, (1S)-8a, (1S)-15a, and (1S)-18a all manifest DAT $IC_{50}$s of 0.3–7.4 nM while the 1R enantiomers (1R)-8a, (1R)-15a, and (1R)-18a manifest DAT $IC_{50}$'s in the range of 265–2,690 nM. Selectivities for DAT versus SERT inhibition follow similarly. Thus the less active 1R-enantiomer series of the 3,4-dichlorophenyl analog manifests selectivities that range from 0.05–11-fold ((1R)-8a, (1R)-15a and (1R)-18a). In contrast, the active 1S-enantiomers show clear differences in selectivity (50–1,610 for (1S)-15a, (1S)-8a and (1S)-18a). Biological enantioselectivity is conserved for bridge hydroxylated tropanes.

Although the 7β-hydroxy-C2α-methylester 33 is less potent (Table 3) at both the DAT ($IC_{50}$=48 nM) and the SERT ($IC_{50}$=533 nM) than the C2β analog 15a (DAT: 1.42 nM; SERT: 27.7 nM), it is still almost twice as potent as cocaine at the DAT. In the absence of ring substitution, as in 34, the 6-hydroxy-C2α-compound is inactive.

Replacement of the C2 ester with a C2 ethyl ketone leads to quite potent inhibitors (Table 3). Thus, 23 manifests a DAT $IC_{50}$=0.81 nM and a SERT $IC_{50}$=97 nM. As may be anticipated, when a C2 ethyl ketone is present in a 3α-3,4-dichlorophenyl analog, as in 26, one of the most selective and potent DAT inhibitors is discovered (DAT: 1.1 nM; SERT: 2,520 nM) (see Scheme 3).

The orientation of the oxygen at the 6 or 7-position is not absolutely crucial for biological activity since both α-, β- and even "planar" 7-ketones manifest nanomolar binding affinity at the DAT. Indeed, if this is so, then the hydrogen bonding between an hydroxyl at this position and the nitrogen may be of limited consequence. In this regard, the 7α-OH compound 30b (Scheme 5) is about half as potent ($IC_{50}$=3.04 nM) as the 7β-OH analog 18a at the DAT ($IC_{50}$=1.19 nM). The 7-keto analog 19 (Scheme 2) remains quite potent at 14.1 nM. In the 6-OH series, the same holds true; the 6β 17a binds with an affinity of 6.09 nM, and the 6α 30a manifests an $IC_{50}$=33.2 nM.

Three conclusions emerge: First, 2β-substitution provides greater potency than 2α-substitution. Second, replacement of the C2-ester with a C2-ketone retains potency at the DAT. Third, both 6α- and 7α-hydroxylated and 7-keto compounds prove potent DAT inhibitors.

The compounds of the invention can be prepared either as free bases or as a pharmacologically active salt thereof such as hydrochloride, tartrate, sulfate, naphthalene-1,5-disulfonate or the like.

The present invention also provides pharmaceutical compositions, preferably comprising the compounds of the present invention in a pharmaceutically acceptable carrier. Pharmaceutically acceptable carriers are well known to those skilled in the art. An exemplary pharmaceutical composition is a therapeutically effective amount of a compound of the invention optionally included in a pharmaceutically-acceptable and compatible carrier. The term "pharmaceutically-acceptable and compatible carrier" as used herein, and described more fully below, refers to e.g., one or more compatible solid or liquid filler diluents or encapsulating substances that are suitable for administration to a human or other animal. The route of administration can be varied but is principally selected from intravenous, nasal and oral routes. For parenteral administration, e.g., it will typically be injected in a sterile aqueous or non-aqueous solution, suspension or emulsion in association with a pharmaceutically-acceptable parenteral carrier such as physiological saline.

The term "therapeutically-effective amount" is that amount of the present pharmaceutical compositions which produces a desired result or exerts a desired influence on the particular condition being treated. Various concentrations may be used in preparing compositions incorporating the same ingredient to provide for variations in the age of the patient to be treated, the severity of the condition, the duration of the treatment and the mode of administration. An effective dose of the compound is administered to a patient based on $IC_{50}$ values determined in vitro.

The term "compatible", as used herein, means that the components of the pharmaceutical compositions are capable of being commingled with the compounds of the present invention, and with each other, in a manner such that there is no interaction that would substantially impair the desired pharmaceutical efficacy.

Dose of the pharmaceutical compositions of the invention will vary depending on the subject and upon particular route of administration used. Pharmaceutical compositions of the present invention can also be administered to a subject according to a variety well-characterized protocols.

In a preferred embodiment, the pharmaceutical composition is a liquid composition in pyrogen-free, sterilized container or vial. The container can be unit dose or multidose.

The compounds and pharmaceutical preparations of the present invention can be used to inhibit the %-hydroxytryptamine reuptake of a monoamine transporter, particularly reuptake by the dopamine transporter, serotonin transporter or norepinephrine transporter.

Dysfunction of dopamine neurons has been implicated in several neuropsychiatric diseases. Imaging of the dopamine neurons offers important clinical information relevant to diagnosis and therapeutic treatments. Dopamine neurons produce dopamine, release the neurotransmitter and remove the released dopamine with a dopamine transporter protein. Compounds that bind to the dopamine transporter are effective measures of dopamine neurons and can be transformed into imaging agents for PET and for SPECT imaging. In identifying a suitable compound for the dopamine transporter, an essential first step is to measure the affinity and selectivity of a candidate at the dopamine transporter. The affinity is measured by conducting radioreceptor assays. A radiolabeled marker for the transporter, e.g., ($^3$H)WIN 35,428, is incubated with the unlabeled candidate and a source of the transporter, usually brain striatum. The effect of various concentrations of the candidate on inhibiting (3H)WIN 35,428 binding is quantified. The concentration of the compound that inhibits 50% of ($^3$H)WIN 35,428 bound to the transporter ($IC_{50}$ value) is used as a measure of its affinity for the transporter. A suitable range of concentrations of the candidate typically is 1–10 nM.

It is also important to measure the selectivity of the candidate of the dopamine compared with the serotonin transporter. The serotonin transporter is also detectable in the striatum, the brain region with the highest density of dopamine neurons and in brain regions surrounding the striatum. It is necessary to determine whether the candidate compound is more potent at the dopamine than the serotonin transporter. If more selective (>10-fold), the probe will permit accurate measures of the dopamine transporter in this region of interest or will provide effective treatment modality for the dopamine transporter. Therefore, a measure of probe affinity of the serotonin transport is conducted by assays paralleling the dopamine transporter assays. ($^3$H) Citalopram is used to radiolabel binding sites on the serotonin transporter and competition studies are conducted with the candidate compound at various concentrations in order to generate an $IC_{50}$ value.

This invention will be illustrated further by the following examples. These examples are not intended to limit the scope of the claimed invention in any manner. The Examples provide suitable methods for preparing compounds of the present invention. However, those skilled in the art may make compounds of the present invention by any other suitable means. As is well known to those skilled in the art, other substituents can be provided for the illustrated compounds by suitable modification of the reactants.

All exemplified target compounds are fully analyzed (mp, TLC, CHN, GC and/or HPLC) and characterized ($^1$H NMR, $^{13}$C NMR, MS, IR) prior to submission for biological evaluation. The affinity of all the compounds for the DAT, SERT and NET are measured. NMR spectra are recorded on a Bruker 100, a Varian XL 400, or a Bruker 300 NMR spectrometer. Tetramethylsilane ("PMS") is used as internal standard. Melting points are uncorrected and are measured on a Gallenkamp melting point apparatus. Thin layer chromatography (TLC) is carried out on Baker Si 250F plates. Visualization is accomplished with iodine vapor, UV exposure or treatment with phosphomolybdic acid (PMA). Preparative TLC is carried out on Analtech uniplates Silica Gel GF 2000 microns. Flash chromatography is carried out on Baker Silica Gel 40 mM. Elemental Analyses are performed by Atlantic Microlab, Atlanta, Ga. and are within 0.4% of calculated values for each element. A Beckman 1801 Scintillation Counter is used for scintillation spectrometry. 0.1% Bovine Serum Albumin ("BSA") and (−)-cocaine is purchased from Sigma Chemicals. All reactions are conducted under an inert ($N_2$) atmosphere.

$^3$H-WIN 35,428 ($^3$H-CFT, 2β-carbomethoxy-3β-(4-fluorophenyl)-N-$^3$H-methyltropane, 79.4–87.0 Ci/mmol) and $^3$H-citalopram (86.8 Ci/mmol) is purchased from DuPont-New England Nuclear (Boston, Mass.). (R)-(−)-Cocaine hydrochloride for the pharmacological studies was donated by the National Institute on Drug Abuse (NIDA). Fluoxetine was donated by E. Lilly & Co. HPLC analyses are carried out on a Waters 510 system with detection at 254 nm on a Chiralcel OC column (flow rate: 1 mL/min).

EXAMPLES

NMR spectra were recorded in $CDCl_3$, unless otherwise mentioned, on a JEOL 300 NMR spectrometer operating at 300.53 MHz for $^1$H, and 75.58 MHz for $^{13}$C. TMS was used as internal standard. Melting points are uncorrected and were measured on a Gallenkamp melting point apparatus. Thin layer chromatography (TLC) was carried out on Baker Si250F plates. Visualization was accomplished with either UV exposure or treatment with phosphomolybdic acid (PMA). Flash chromatography was carried out on Baker Silica Gel 40 μM. Elemental analyses were performed by Atlantic Microlab, Atlanta, Ga. HRMS was performed at Harvard University, MA. Optical rotations were measured on a Perkin Elmer 241 Polarimeter. All reactions were conducted under an inert ($N_2$) atmosphere. {$^3$H}WIN 35,428 (2β-carbomethoxy-3β-(4-fluorophenyl)-N-{$^3$H}methyltropane, 79.4–87.0 Ci/mmol) and {$^3$H}citalopram (86.8 Cl/mmol) were purchased from DuPont-New England Nuclear (Boston, Mass.). (1S)-(–)-Camphanic chloride (98% ee) was purchased from Aldrich. A Beckman 1801 scintillation counter was used for scintillation spectrometry. Bovine semen albumin (0.1%) was purchased from Sigma Chemicals. (R)-(–)-Cocaine hydrochloride for the pharmacological studies was donated by the National Institute on Drug Abuse {NIDA}. Room temperature is ca. 22° C. TMSBr: trimethylsilyl bromide. Solution A: 2-hydroxy-2-methylpropanol/1,2-dichloroethane, 37:63. Yields have not been optimized.

Example 1

6-Hydroxy-2-methoxycarbonyl-8-methyl-3-oxo-8-azabicyclo{3.2.1}octane (1a) and 7-hydroxy-2-methoxycarbonyl-8-methyl-3-oxo-8-azabicyclo{3.2.1}octane (1b)

Acetonedicarboxylic acid (40 g, 0.27 mol) was added slowly to a solution of acetic acid (60 mL) and acetic anhydride (43 mL) at 0° C. The mixture was stirred below 10° C. The acid dissolved slowly and a pale yellow precipitate was formed over 3 h. The product was filtered, washed with glacial acetic acid (30 mL), followed by benzene (100 mL). The resultant white powder was dried at high vacuum to afford 30 g of the desired acetonedicarboxylic acid anhydride (86%): mp 137–138° C. (lit.[38] 137.5–138.5° C.). Cold dry methanol (160 mL) was added to acetonedicarboxylic acid anhydride (50 g, 0.39 mol). The solution was allowed to stand for 1 h and filtered. The filtrate, acetonedicarboxylic acid monomethylester,[38] was used directly in the following reaction. A mixture of 2,5-dimethoxydihydrofuran (53.6 g, 0.41 mol) and 3 M aqueous HCl (1 L) was allowed to stand for 12 h at 22° C. The brown solution was cooled to 0° C. and ice (500 g) added before being neutralized with aqueous 3 M NaOH (1 L). Methylamine hydrochloride (41 g, 0.62 mol) in $H_2O$ (300 mL) was added to this solution followed by the preformed methanol solution (160 mL above) of acetonedicarboxylic acid monomethylester and sodium acetate (50 g) in $H_2O$ (200 mL). The mixture (pH 4.5) was stirred for 2 days at 22° C. The resultant red solution was extracted with hexanes (500 mL×2) to remove non-polar by-products. The aqueous solution was neutralized and saturated by adding solid $K_2CO_3$ (960 g). The saturated solution was extracted with $CH_2Cl_2$ (300 mL×3) and the combined extracts were dried over anhydrous $K_2CO_3$, filtered and concentrated to provide the crude product (21.6 g). The aqueous solution was extracted with Solvent A and the combined extracts were dried over anhydrous $K_2CO_3$, filtered and concentrated to provide a pale yellow solid that was found to be a mixture of 6- and 7-hydroxy-2-methoxycarbonyl-8-methyl-3-oxo-8-azabicyclo{3.2.1}octanes of good purity (30.6 g) and were used without further purification. The crude product obtained from the $CH_2Cl_2$ extracts was purified by column chromatography {10% $NEt_3$, 60% EtOAc in hexanes (30–90%), followed by 10% $NEt_3$, 5% MeOH and 85% EtOAc} to afford 6.2 g of a mixture of 6β- and 7β-methoxy-2-methoxycarbonyl-8-methyl-3-oxo-8-azabicyclo{3.2.1}octane (Chen, Z.; Meltzer, P. C., *Tetrahedron Lett.* 1997, 38, 1121–1124) as an oil: $R_f$ 0.44 (10% $NEt_3$, 20% EtOAc in hexanes) and 12.8 g of 6β- and 7β-hydroxy-2-methoxycarbonyl-8-methyl-3-oxo-8-azabicyclo{3.2.1}octane as yellow solids (1a and 1b). The total yield of 6β- and 7β-hydroxy-2-methoxycarbonyl-8-methyl-3-oxo-8-azabicyclo{3.2.1}octane was 43.4 g (52%). $^1$H NMR of 1a (mixture of the keto-2α- and keto-2β-epimers and the intermediate enol compounds) δ 4.18–4.02 (m, 1H), 3.89–3.85 (m, 1H), 3.78, 3.76 (2s, 3H), 3.45–3.36 (m, 1H), 3.21 (d, J=6 Hz, 1H), 2.75–2.62 (m, 2H), 2.40, 2.38 (2s, 3H), 2.37–2.22 (m, 1H), 2.1–1.92 (m, 2H). $^1$H NMR of 1b (observed in the intermediate enol form only) δ 11.83 (s, 1H), 4.06 (dd, J=5.8, 2.0 Hz, 1H), 3.78 (s, 3H), 3.66 (s, 1H), 3.37 (t, J=4.7 Hz, 1H), 2.66 (dd, J=18.9, 4.6 Hz, 1H), 2.39 (s, 3H), 2.02–1.96 (m, 1H), 1.73 (d, J=18.6 Hz, 1H).

Example 2

6β-Methoxymethoxy-2-methoxycarbonyl-8-methyl-3-oxo-8-azabicyclo{3.2.1}octane (2a) and 7β-Methoxymethoxy-2-methoxycarbonyl-8-methyl-3-oxo-8-azabicyclo{3.2.1}octane (2b)

To a solution of a mixture of 6β- and 7β-methoxy-2-methoxycarbonyl-8-methyl-3-oxo-8-azabicyclo{3.2.1}octane (1a and 1b) (30.6 g, 140 mmol) in anhydrous $CH_2Cl_2$ (600 mL) and dimethoxymethane (170 mL), p-toluenesulfonic acid monohydrate (31 g, 160 mmol) was added in a 2 L flask fitted with a Soxhlet extractor containing 4 Å molecular sieves. The reaction mixture was heated to reflux until complete. The mixture was cooled and treated with saturated aqueous $Na_2CO_3$ (200 mL) and extracted with $CH_2Cl_2$ (300 mL×4). The combined organic extracts were dried over $K_2CO_3$, filtered and concentrated to obtain a mixture of MOM protected alcohols. The mixture was separated by column chromatography {(5–10% $NEt_3$, 65% EtOAc in hexanes (30–50%)} to obtain 6β-hydroxy-2-methoxycarbonyl-8-methyl-3-oxo-8-azabicyclo{3.2.1}octane 2a (11.0 g, 30%) and 7β-hydroxy-2-methoxycarbonyl-8-methyl-3-oxo-8-azabicyclo{3.2.1}octane 2b (10.6 g, 28%) along with a mixture of the MOM protected alcohols 2a and 2b (2.9 g, 8%).

2a: yellow oil: $R_f$ 0.55 (10% $Et_3N$ in EtOAc); $^1$H NMR (mixture of the keto-2α- and keto-2β-epimers and the intermediate enol compounds) δ 11.69 (s, enol H), 4.63, 4.62, 4.60 (3s, 2H), 4.10–3.96 (m, 2H), 3.88 (d, J=6.6 Hz, 1H), 3.76, 3.75, 3.74 (3s, 3H), 3.36, 3.34 (2s, 3H), 3.11–2.71 (m, 1H), 2.69, 2.62, 2.41 (3s, 3H) 2.34–1.91 (m, 2H). 2b: yellow solid: $R_f$ 0.38 (10% $Et_3N$, 30% EtOAc and 60% hexanes); $^1$H NMR (observed in the intermediate enol form only) δ 11.77 (s, 1H), 4.69 (d, J=6.6 Hz, 1H), 4.63 (d, J=6.6 Hz, 1H), 4.06 (dd, J=1.6, 7.2 Hz, 1H), 3.81 (s, 1H), 3.79 (s, 3H), 3.45 (dd, J=4.6, 6.6 Hz, 1H), 3.36 (s, 3H), 2.75–2.66 (m, 1H), 2.43 (s, 3H), 2.18 (dd, J=7.4, 14.3 Hz, 1H), 1.99 (dd, J=7.4, 14.3 Hz, 1H), 1.79 (d, J=18.7 Hz, 1H).

Example 3

2-Carbomethoxy-3-trifluoromethylsulfonyloxy-7β-methoxymethoxy-8-methyl-8-azabicyclo{3.2.1}oct-2-ene (3b)

To a solution of 2-carbomethoxy-7β-methoxymethoxy-8-methyl-3-oxo-8-azabicyclo{3.2.1}octane, 2b (4.25 g, 16.5 mmol) in THF (150 mL), sodium bistrimethylsilylamide (25 mL; 1.0 M solution in THF) was added dropwise at –70° C. under nitrogen. After stirring for 30 min, N-phenyltrifluoromethanesulfonimide (7.06 g, 19.8 mmol) was added in one portion at −70° C. The reaction was allowed to warm up to 22° C. and stirred overnight. The volatile solvents were removed on a rotary evaporator. The residue was dissolved in $CH_2Cl_2$ (200 mL), washed with $H_2O$ (100 mL) and brine (100 mL). The dried ($MgSO_4$) $CH_2Cl_2$ layer was concentrated to dryness and purified by flash chromatography (2–10% $Et_3N$, 15–30% EtOAc in hexanes) to afford 3.63 g (57%) of 3b as a pale yellow oil: $R_f$ 0.29 (10% $Et_3N$, 30% EtOAc, 60% hexanes); $^1H$ NMR of 3b δ 4.74 (d, J=6.8 Hz, 1H), 4.65 (d, J=6.8 Hz, 1H), 4.21 (dd, J=1.6, 7.3 Hz, 1H), 4.0 (s, 1H), 3.83 (s, 3H), 3.56–3.50 (m, 1H), 3.37 (s, 3H), 2.80 (dd, J=4.1, 18.4 Hz, 1H), 2.44 (s, 3H), 2.21 (dd, J=7.4, 14.0 Hz, 1H), 2.02 (dd, J=7.4, 14.1 Hz, 1H), 1.89 (d, J=18.7 Hz, 1H); HRMS Cal (M+1): 390.0856; Found 390.0811.

Example 4

2-Carbomethoxy-3-(trifluoromethyl)sulfonyloxy-6β-methoxymethoxy-8-methyl-8-azabicyclo{3.2.1}oct-2-ene (3a)

Prepared as described above for 3b (64%): $R_f$ 0.45 (10% $Et_3N$, 30% EtOAc, 60% hexanes); $^1H$ NMR (100 MHz): δ 4.64 (s, 2H), 4.07 (dd, 1H), 3.81 (s, 3H), 3.5–3.30 (m, 2H), 3.36 (s, 3H), 2.85 (dd, 1H), 2.44 (s, 3H), 2.4–1.8 (m, 3H).

Example 5

General Procedures for Suzuki Coupling Reactions to Obtain 4 and 5

To a solution of 2β-carbomethoxy-3-{(trifluoromethyl)sulfonyl}oxy-7β- (or 6β-) methoxymethoxy-8-methyl-8-azabicyclo{3.2.1}oct-2-ene, 3 (1 eq) in diethoxymethane was added LiCl (2 eq), $Na_2CO_3$ (2 M aqueous solution, 2 eq) and the aryl boronic acid (1.1 eq). The solution was stirred and deoxygenated by bubbling $N_2$ into the solution for 15 min before the addition, in one portion, of tris(dibenzylideneacetone)dipalladium(0) (0.1 eq) under a strong stream of $N_2$. After being further deoxygenated for another 0.5 h, the solution was heated to reflux under $N_2$ until no starting material remained (~3–6 h) (TLC). The mixture was cooled to 22° C. and filtered through Celite. The Celite was washed with EtOAc. The combined organic layers were separated and the aqueous layer was extracted with EtOAc. The organic layer was combined and dried over $K_2CO_3$. The solvent was removed and the residue was purified by flash column chromatography (10% $Et_3N$, 30% EtOAc, 60% hexanes) to afford the coupled compounds.

Example 6

2-Carbomethoxy-3-(3,4-dichlorophenyl)-6β-methoxymethoxy-8-methyl-8-azabicyclo{3.2.1}oct-2-ene (4a)

The general procedure described above was followed. The product was obtained as an oil (86%): $R_f$ 0.16 (10% $Et_3N$, 20% EtOAc, 70% hexanes); $^1H$ NMR δ 7.39 (d, 1H), 7.21 (d, 1H), 6.95 (dd, 1H), 4.66 (s, 2H), 4.11 (dd, 1H), 3.95 (d, 1H), 3.35 (s, 3H), 3.39–3.35 (m, 4H), 2.70 (dd, 1H), 2.54–2.43 (m, 4H), 2.19 (ddd, 1H), 2.02 (d, 1H).

Example 7

2-Carbomethoxy-3-(2-naphthyl)-6β-methoxymethoxy-8-methyl-8-azabicyclo{3.2.1}oct-2-ene (4b)

The general procedure described above was followed. The product was obtained as an oil (53%): $R_f$ 0.36 (10% $Et_3N$, 30% EtOAc, 60% hexane); $^1H$ NMR δ 7.84–7.77 (m, 3H), 7.59 (s, 1H), 7.50–7.44 (m, 2H), 7.24 (dd,1H), 4.69 (s, 2H), 4.20 (dd, 1H), 4.00 (d, 1H), 3.43 (s, 3H), 3.41–3.38 (m, 4H), 2.82 (dd, 1H), 2.59–2.50 (m, 4H), 2.26–2.17 (m, 2H).

Example 8

2-Carbomethoxy-3-(4-fluorophenyl)-6β-methoxymethoxy-8-methyl-8-azabicyclo{3.2.1}oct-2-ene (4c)

The general procedure described above was followed. The product was obtained as a yellow oil (93%): $R_f$ 0.12 (10% $Et_3N$, 20% EtOAc, 70% hexane); $^1H$ NMR δ 7.11–6.97 (m, 4H), 4.67 (s, 2H), 4.12 (dd, 1H), 3.94 (d, 1H), 3.49 (s, 3H), 3.38–3.33 (m, 4H), 2.71 (dd, 1H), 2.50–2.44 (m, 4H), 2.19 (ddd, 1H), 2.06 (d, 1H).

Example 9

2-Carbomethoxy-3-phenyl-6β-methoxymethoxy-8-methyl-8-azabicyclo{3.2.1}oct-2-ene (4d)

The general procedure described above was followed. The product was obtained as a light yellow oil (89%): $R_f$ 0.16 (10% $Et_3N$, 20% EtOAc, 70% hexane); $^1H$ NMR 7.36–7.23 (m, 3H), 7.14–7.11 (m, 2H), 4.67 (s, 2H), 4.16 (dd, 1H), 4.03 (d, 1H), 3.47 (s, 3H), 3.43 (m, 1H), 3.38 (s, 1H), 2.87 (dd, 1H), 2.58–2.51 (m, 4H), 2.23 (ddd, 1H), 2.15 (d, 1H).

Example 10

2-Carbomethoxy-3-(3,4-dichlorophenyl)-7β-methoxymethoxy-8-methyl-8-azabicyclo{3.2.1}oct-2-ene (5a)

The general procedure described above was followed. The product was obtained as an oil (80%): $R_f$ 0.33 (10% $Et_3N$, 20% EtOAc, 70% hexane); $^1H$ NMR (100 MHz) δ 7.40 (d, 1H), 7.19 (d, 1H), 6.93 (dd, 1H), 4.71 (m, 2H), 4.24 (dd, 1H), 3.91 (s, 1H), 3.56 (s, 3H), 3.48 (bs, 1H), 3.39 (s, 3H), 2.52 (s, 3H), 2.90–1.5 (m, 4H); $^{13}C$ NMR δ 168.3, 144.8, 142.0, 133.4, 132.8, 131.3, 129.9, 128.2, 127.4, 96.4, 83.2, 66.3, 57.5, 56.5, 52.7, 41.5, 36.0, 35.7.

Example 11

2-Carbomethoxy-3-(2-naphthyl)-7β-methoxymethoxy-8-methyl-8-azabicyclo{3.2.1}oct-2-ene (5b)

The general procedure described above was followed. The product was obtained as a yellow oil (100%): $R_f$ 0.52 (10% $Et_3N$, 20% EtOAc, 70% hexane); $^1H$ NMR δ 7.79 (m, 3H), 7.57 (s, 1H), 7.48 (m, 2H), 7.22 (d, 1H), 4.74 (dd, 2H), 4.35 (dd, 1H), 3.95 (s, 1H), 3.52–3.46 (m, 4H), 3.41 (s, 3H), 2.85 (dd, 1H), 2.58 (s, 3H), 2.27 (dd, 1H), 2.15 (dd, 1H), 1.98 (d, 1H).

Example 12

2-Carbomethoxy-3-(4-fluorophenyl)-7β-methoxymethoxy-8-methyl-8-azabicyclo{3.2.1}oct-2-ene (5c)

The general procedure described above was followed. The product was obtained as an oil (100%): $R_f$ 0.53 (10% Et$_3$N, 20% EtOAc, 70% hexane); $^1$H NMR δ 7.15–7.00 (m, 4H), 4.75 (dd, 2H), 4.29 (dd, 1H), 3.89 (s, 1H), 3.53 (s, 3H), 3.45 (m, 1H), 3.39 (s, 3H), 2.73 (dd, 1H), 2.51 (s, 3H), 2.25 (dd, 1H), 2.07 (dd, 1H), 1.85 (d, 1H).

Example 13

2-Carbomethoxy-3-phenyl-7β-methoxymethoxy-8-methyl-8-azabicyclo{3.2.1}oct-2-ene (5d)

The general procedure described above was followed. The product was obtained as an oil (29%): $R_f$ 0.56 (10% Et$_3$N, 30% EtOAc, 70% hexane); $^1$H NMR δ 7.32–7.27 (m, 3H), 7.12–7.07 (m, 2H), 4.73 (dd, 2H), 4.30 (dd, 1H), 3.89 (s, 1H), 3.50 (s, 3H), 2.47 (m, 1H), 3.38 (s, 3H), 2.76 (dd, 1H), 2.52 (s, 3H), 2.25 (dd, 1H), 2.09 (dd, 1H), 1.88 (d, 1H).

Example 14

General Procedure for SmI$_2$ Reduction Reactions to Obtain 9–12

Note that the 3α and 3β isomers are obtained and are separated by column chromatography. To a THF (anhydrous, 5–10 mL) solution of 2-carbomethoxy-3-aryl-7-(or 6-)methoxymethoxy-8-azabicyclo{3.2.1}oct-2-ene and anhydrous methanol (20 eq) at –78° C. under N$_2$ was added SmI$_2$ (0.1 M solution in THF, 8 eq) dropwise. The resulting solution was kept stirring at –78° C. for 4 h and was then quenched with H$_2$O (10 mL). After warming to 22° C., sat. NaHCO$_3$ was added and the precipitate was filtered through a Celite pad. The pad was washed with EtOAc and the aqueous layer was back extracted with EtOAc three times. The organic layers were combined, washed with brine and dried over K$_2$CO$_3$. The solvent was removed and the residue was purified by two consecutive flash columns (First: 10% Et$_3$N, 30% EtOAc, 60%, hexanes; Second: 5% MeOH, 95% CHCl$_3$) to obtain the 2β, 3β- (9 and 11) and 2β, 3α- (10 and 12) isomers.

Example 15

2β-Carbomethoxy-3β-(3,4-dichlorophenyl)-6β-methoxymethoxy-8-methyl-8-azabicyclo{3.2.1}octane (9a) and 2β-carbomethoxy-3α-(3,4-dichlorophenyl)-6β-methoxymethoxy-8-methyl-8-azabicyclo{3.2.1}octane (10a)

The title compounds were prepared as in the general procedure given above. Compound 9a (an oil: 16%) could not be readily purified and was therefore carried through to the next step as is (see 14a). $R_f$ 0.67 (Et$_3$N 10%, EtOAc 30%, hexanes 60%). Compound 10a was obtained as an oil (8%): $R_f$ 0.30 (3% MeOH, CHCl$_3$); $R_f$ 0.69 (Et$_3$N 10%, EtOAc 30%, hexanes 60%). $^1$H NMR δ 7.32 (d, 1H), 7.25 (d, 1H), 7.01 (d, 1H), 4.64 (dd, 2H), 4.12 (dd, 1H), 3.59–3.55 (m, 5H), 3.39–3.01 (m, 5H), 2.55 (s, 3H), 2.46–2.25 (m, 3H), 2.10 (dd, 1H), 1.29 (ddd, 1H).

Example 16

2β-Carbomethoxy-3β-(2-naphthyl)-6β-methoxymethoxy-8-methyl-8-azabicyclo{3.2.1}octane (9b) and 2β-carbomethoxy-3α-(2-naphthyl)-6β-methoxymethoxy-8-methyl-8-azabicyclo{3.2.1}octane (10b)

The title compounds were prepared as in the general procedure given above. Compound 9b was obtained as an oil (38%): $R_f$ 0.30 (3% MeOH/CHCl$_3$); $^1$H NMR δ 7.75 (t, 3H), 7.65 (s, 1H), 7.46–7.33 (m, 3H), 4.67 (s, 2H), 4.32 (dd, 1H), 3.80 (d, 1H), 3.47 (s, 1H), 3.44 (s, 3H), 3.39 (s, 3H), 2.97–2.91 (m, 2H), 2.68 (dt, 1H), 2.52 (s, 3H), 2.37 (ddd, 1H), 2.27 (dd, 1H), 1.92 (dt, 1H). Compound 10b was obtained as an oil (38%: $R_f$ 0.41 (5% MeOH/CHCl$_3$); $^1$H NMR δ 7.70 (t, 3H), 7.62 (s, 1H), 7.48–7.38 (m, 2H), 7.32 (d, 1H), 4.66 (dd, 2H), 4.19 (dd, 1H), 3.65 (s, 1H), 3.59 (s, 1H), 3.54 (s, 3H), 3.39–3.36 (m, 4H), 2.59 (s, 3H), 2.57–2.46 (m, 2H), 2.10 (ddd, 1H), 2.18 (dd, 1H), 1.53 (ddd, 1H).

Example 17

2β-Carbomethoxy-3β-(4-fluorophenyl)-6β-methoxymethoxy-8-methyl-8-azabicyclo{3.2.1}octane (9c) and 2β-carbomethoxy-3α-(4-fluorophenyl)-6β-methoxymethoxy-8-methyl-8-azabicyclo{3.2.1}octane (10c)

The title compounds were prepared as in the general procedure given above. Compound 9c was obtained as an oil (31%): $R_f$ 0.71 (10% Et$_3$N, 30% EtOAc, 60%/hexane); $^1$H NMR δ 7.20–7.15 (m, 2H), 6.98–6.92 (m, 2H), 4.65 (s, 2H), 4.26 (dd, J=7.4, 3.3 Hz, 1H) 3.76 (d, J=6.6 Hz, 1H), 3.50 (s, 3H), 3.42 (s, 1H), 3.38 (s, 3H), 2.82–2.71 (m, 2H), 2.57–2.48 (m, 4H), 2.35 (ddd, J=14.3, 7.4, 3.3 Hz, 1H), 2.19 (dd, J=14.3, 7.4 Hz, 1H), 1.78 (m, 1H). Compound 10c was obtained as an oil (23%): $R_f$ 0.71 (10% Et$_3$N, 30% EtOAc, 60% hexane); $^1$H NMR 7.15–7.11 (m, 2H), 6.98–6.91 (m, 2H), 4.64 (dd, 2H), 4.13 (dd, J=7.1, 3.3 Hz, 1H), 3.60–3.53 (m, 4H), 3.40–3.31 (m, 5H), 2.57 (s, 3H), 2.54–2.26 (m, 3H), 2.12 (dd, J=14.0, 7.1 Hz, 1H), 1.33 (ddd, J=14.0, 10.9, 1.6 Hz, 1H).

Example 17

2β-Carbomethoxy-3β-phenyl-6β-methoxymethoxy-8-methyl-8-azabicyclo(3.2.1}octane (9d) and 2β-carbomethoxy-3α-phenyl-6β-methoxymethoxy-8-methyl-8-azabicyclo{3.2.1}octane (10d)

The title compounds were prepared as in the general procedure given above. Compound 9d obtained as an oil (28%): $R_f$ 0.25 (5% MeOH/CHCl$_3$); $^1$H NMR δ 7.29–7.13 (m, 5H), 4.66 (s, 2H), 4.27 (dd, J=7.1, 3.3 Hz, 1H), 2.77 (m, 1H), 3.48 (s, 3H), 3.43 (s, 1H), 3.38 (s, 3H), 2.86 (t, J=4.1 Hz, 1H), 2.79 (dt, J=12.9, 4.9 Hz, 1H), 2.60–2.50 (m, 4H), 2.35 (ddd, J=14, 6.8, 3.3 Hz, 1H), 2.20 (dd, J=14.3, 7.4 Hz, 1H), 1.81 (dt, J=12.4, 3.9 Hz, 1H). Compound 10d obtained as an oil (25%): $R_f$ 0.50 (5% MeOH/CHCl$_3$); $^1$H NMR δ 7.29–7.14 (m, 5H), 4.64 (dd, 2H), 4.14 (dd, J=7.1, 3.0 Hz, 1H), 3.59–3.57 (m, 4H), 3.48–3.32 (m, 5H), 2.57 (s, 3H), 2.50–2.37 (m, 2H), 2.29 (ddd, J=14.6, 7.1, 3.0 Hz, 1H), 2.1 (dd, J=14.3, 7.4 Hz, 1H), 1.4 (ddd, 1H).

Example 18

2β-Carbomethoxy-3β-(3,4-dichlorophenyl)-7β-methoxymethoxy-8-methyl-8-azabicyclo{3.2.1}octane (11a) and 2β-carbomethoxy-3α-(3,4-dichlorophenyl)-7β-methoxymethoxy-8-methyl-8-azabicyclo{13.2.}octane (12a)

The title compounds were prepared as in the general procedure given above. Compound 11a obtained as a yellow oil (37%): $R_f$ 0.52 (5% MeOH/CHCl$_3$); $^1$H NMR δ 7.35 (d, 1H), 7.30 (d, 1H), 7.10 (dd, 1H), 4.70 (dd, 2H), 4.35 (dd, 1H), 3.62 (s, 1H), 3.54 (m, 4H), 3.42 (s, 3H), 3.00 (m, 1H), 2.72–2.62 (m, 1H), 2.51–2.41 (m, 4H), 2.25 (ddd, 1H), 2.07 (dd, 1H), 1.59 (dt, 1H). Compound 12a was obtained as a white solid (36%): $R_f$ 0.67 (5% MeOH/CHCl$_3$); $^1$H NMR δ 7.32 (d, 1H), 7.25 (d, 1H), 7.02 (dd, 1H), 4.66 (dd, 2H), 4.25 (dd, 1H), 3.62 (s, 3H), 3.48–3.32 (m, 6H), 2.54–2.47 (m, 4H), 2.43–2.33 (m, 1H), 2.20 (ddd, 1H), 2.00 (dd, 1H), 1.21 (dt, 1H).

Example 19

2β-Carbomethoxy-3β-(2-naphthyl)-7β-methoxymethoxy-8-methyl-8-azabicyclo{3.2.1}octane (11b) and 2β-carbomethoxy-3α-(2-naphthyl)-7β-methoxymethoxy-8-methyl-8-azabicyclo{3.2.1}octane (12b)

The title compounds were prepared as in the general procedure given above. Compound 11b was obtained as an oil (29%): $R_f$ 0.41 (5% MeOH/CHCl$_3$); $^1$H NMR δ 7.80–7.75 (m, 3H), 7.68 (s, 1H), 7.48–7.35 (m, 3H), 4.74 (dd, 2H), 4.44 (dd, 1H), 3.67–3.59 (m, 2H), 3.44 (s, 6H), 3.17 (t, 1H), 2.89 (dt, 1H), 2.69 (dt, 1H), 2.52 (s, 3H), 2.27 (ddd, 1H), 2.15 (dd, 1H), 1.72 (dt, 1H). Compound 12b was obtained as an oil (26%): $R_f$ 0.31 (5% MeOH/CHCl$_3$); $^1$H NMR δ 7.78–7.72 (m, 3H), 7.67 (s, 1H), 6.95–6.88 (m, 3H), 4.67 (dd, 2H), 4.28 (dd, 1H), 3.58 (s, 3H), 3.53 (s, 1H), 3.45–3.37 (m, 5H), 2.50 (t, 1H), 2.47 (s, 3H), 2.42 (dt, 1H), 2.15 (ddd, 1H), 2.00 (dd, 1H), 1.23 (dt, 1H).

Example 20

2β-Carbomethoxy-3β-(4-fluorophenyl)-7β-methoxymethoxy-8-methyl-8-azabicyclo{3.2.1}octane (11c) and 2β-carbomethoxy-3α-(4-fluorophenyl)-7β-methoxymethoxy-8-methyl-8-azabicyclo{3.2.1}octane (12c)

The title compounds were prepared as in the general procedure given above. Compound 11c was obtained as an oil (35%): $R_f$ 0.63 (EtOAc); $^1$H NMR δ 7.22–7.18 (m, 2H), 6.98–6.91 (m, 2H), 4.71 (dd, 2H), 4.38 (dd, 1H), 3.62–3.57 (m, 2H), 3.50 (s, 3H), 3.42 (s, 3H), 2.99 (t, 1H), 2.87–2.78 (m, 1H), 2.57–2.48 (m, 4H), 2.22 (ddd, 1H), 2.06 (dd, 1H), 1.61 (dt, 1H). Compound 12c was obtained as a solid (40%): $R_f$ 0.36 (10% Et$_3$N, 30% EtOAc, 60% hexanes); $^1$H NMR δ 7.16–7.10 (m, 2H), 6.97–6.91 (m, 2H), 4.66 (dd, 2H), 4.24 (dd, 1H), 3.59 (s, 3H), 3.46 (m, 1H), 3.39–3.33 (m, 5H), 2.51 (t, 1H), 2.48 (s, 3H), 2.38 (dt, 1H), 2.19 (ddd, 1H), 2.01 (dd, 1H), 1.24 (dt, 1H).

Example 21

2β-Carbomethoxy-3β-phenyl-7β-methoxymethoxy-8-methyl-8-azabicyclo{3.2.1}octane (11d) and 2β-carbomethoxy-3α-phenyl-7β-methoxymethoxy-8-methyl-8-azabicyclo{3.2.1}octane (12d)

The title compounds were prepared as in the general procedure given above. Compound 11d was obtained as an oil (25%): $R_f$ 0.15 (EtOAc); $^1$H NMR δ 7.29–7.22 (m, 4H), 7.18–7.12 (m, 1H), 4.71 (dd, 2H), 4.37 (dd, 1H), 3.61–3.57 (m, 2H), 3.48 (s, 3H), 3.43 (s, 3H), 3.03 (t, 1H), 2.80–2.69 (dt, 1H), 2.60–2.48 (m, 4H), 2.25 (ddd, 1H), 2.07 (dd, 1H), 1.62 (dt, 1H). Compound 12d was obtained as an oil (31%): $R_f$ 0.50 (EtOAc); $^1$H NMR δ 7.30–7.12 (m, 5H), 4.65 (dd, 2H), 4.24 (dd, 1H), 3.60 (s, 3H), 3.51–3.37 (m, 6H), 2.62–2.58 (m, 4H), 2.40 (dt, 1H), 2.20 (ddd, 1H), 2.03 (dd, 1H), 1.25 (dt, 1H).

Example 22

General Procedures for Cleavage of MOM Protecting Group

To a solution of MOM protected alcohol in anhydrous CH$_2$Cl$_2$ containing 4 Å molecular sieves, at 0° C., was added TMSBr (10 eq). The solution was slowly allowed to warm up to 22° C. and stirred overnight. The reaction was quenched by slow addition of aq NaHCO$_3$ and the aqueous layer was exhaustively extracted with CH$_2$Cl$_2$. The extracts were combined and dried over K$_2$CO$_3$. The solvent was removed and residue was purified by flash column chromatography (10% Et$_3$N, 30–90% EtOAc, 60–0% hexanes) to give the product.

Example 23

2-Carbomethoxy-3-(3,4-dichlorophenyl)-6β-hydroxy-8-methyl-8-azabicyclo{3.2.1}oct-2-ene (7a)

The procedure described above was followed. A white crystalline solid was obtained (71%): mp 94.0–96.0° C.; $R_f$ 0.13 (10% Et$_3$N/EtOAc); $^1$H NMR δ 7.39 (d, 1H), 7.21 (d, 1H), 6.95 (dd, 1H), 4.19 (m, 1H), 3.94 (d, J=6.6 Hz, 1H), 3.53 (s, 3H), 3.23 (d, J=5.8 Hz, 1H), 2.65 (dd, J=19.5, 5.8 Hz, 1H), 2.54–2.48 (m, 4H), 2.25 (bs, 1H), 2.09–1.97 (m, 2H). Anal. (C$_{16}$H$_{17}$Cl$_2$NO$_3$) C, H, N.

Example 24

2-Carbomethoxy-3-(2-naphthyl)-6β-hydroxy-8-methyl-8-azabicyclo{3.2.1}oct-2-ene (7b)

The procedure described above was followed to obtain a white powder (29%); mp 165.0–167.0° C.; $R_f$ 0.15 (10% Et$_3$N/EtOAc); $^1$H NMR δ 7.84–7.78 (m, 3H), 7.59 (s, 1H), 7.49–7.46 (m, 2H), 7.25–7.22 (m, 1H), 4.26 (dd, J=7.4, 3.0 Hz, 1H), 4.00 (d, J=6.3 Hz, 1H), 3.45 (s, 3H), 3.27 (d, J=5.5 Hz, 1H), 2.77 (dd, J=19.5, 5.8 Hz, 1H), 2.62–2.55 (m, 4H), 2.19 (d, J=19.5 Hz, 1H), 2.08 (ddd, J=13.5, 6.6, 2.7 Hz, 1H). Anal. (C$_{20}$H$_{21}$NO$_3$) C, H, N.

Example 25

2-Carbomethoxy-3-(4-fluorophenyl)-6β-hydroxy-8-methyl-8-azabicyclo{3.2.1}oct-2-ene (7c)

The procedure described above was followed to obtain a white crystalline solid (22%); mp 124.0–126.0° C.; $R_f$ 0.31 (10% Et$_3$N/EtOAc); $^1$H NMR δ 7.39–6.98 (m, 4H), 4.19 (dd, J=7.1, 2.7 Hz, 1H), 3.94 (d, J=6.6 Hz, 1H), 3.50 (s, 3H), 3.23 (d, J=5.5 Hz, 1H), 2.66 (dd, J=19.5, 5 Hz, 1H), 2.55–2.49 (m, 4H), 2.08–2.01 (m, 2H). Anal. ($C_{16}H_{18}FNO_3$) C, H, N.

Example 26

2-Carbomethoxy-3-phenyl-6β-hydroxy-8-methyl-8-azabicyclo{3.2.1}oct-2-ene (7d)

The procedure described above was followed to obtain a white crystalline solid (13%); mp 165.0–167.0° C.; $R_f$ 0.22 (10% Et$_3$N/EtOAc); $^1$H NMR δ 7.39–7.28 (m, 3H), 7.13–7.10 (m, 2H), 4.21 (dd, J=7.4, 3.0 Hz, 1H), 3.94 (d, J=6.6 Hz, 1H), 3.48 (s, 3H), 3.23 (d, J=5.5 Hz, 1H), 2.70 (dd, J=19.5, 5.5 Hz, 1H), 2.57–2.50 (m, 4H), 2.09 (d, J=19.8 Hz, 1H), 2.07–2.01 (m, 1H). Anal. ($C_{16}H_{19}NO_3$) C, H, N.

Example 27

2-Carbomethoxy-3-(3,4-dichlorophenyl)-7β-hydroxy-8-methyl-8-azabicyclo{3.2.1}oct-2-ene (8a)

The procedure described above was followed. The product was obtained as a white solid (34%): mp 130.4–132.4° C.; $R_f$ 0.1 (EtOAc); $^1$H NMR δ 7.37 (d, 1H), 7.19 (d, 1H), 6.95 (dd, 1H), 4.29 (m, 1H), 3.65 (s, 1H), 3.56 (s, 3H), 3.40 (m, 1H), 2.62 (dd, 1H), 2.48 (s, 3H), 2.08 (m, 2H), 1.80 (d, 1H). Anal. ($C_{16}H_{17}Cl_2NO_3$) C, H, N.

Example 28

(1S)-2-Carbomethoxy-3-(3,4-dichlorophenyl)-7β-hydroxy-8-methyl-8-azabicyclo{3.2.1}oct-2-ene ((1S)-8a)

This compound was obtained from (1S)-28 (vide infra) via the procedure described above: $\{\alpha\}^{21}_D$=−58° (c=1.0, CHCl$_3$), $\{\alpha\}^{21}_D$=−49° (c=0.40, MeOH) (>98% ee from $^1$H NMR of (1S)-28) mp 130.4–131.8° C.

Example 29

(1R)-2-Carbomethoxy-3-(3,4-dichlorophenyl)-7β-hydroxy-8-methyl-8-azabicyclo{3.2.1}oct-2-ene ((1R)-8a)

This compound was obtained from (1R)-2(vide infra) via the procedure described above: $\{\alpha\}^{21}_D$+57° (c=1.0, CHCl$_3$) (>98% ee from $^1$H NMR of (1R)-27) mp 129–131° C.

Example 30

2-Carbomethoxy-3-(2-naphthyl)-7β-hydroxy-8-methyl-8-azabicyclo{3.2.1}oct-2-ene (8b)

The procedure described above was followed. The product was obtained as a white solid (57%): mp 164.2–165.2° C.; $R_f$ 0.4 (5% Et$_3$N/EtOAc); $^1$H NMR δ 7.80 (m, 3H), 7.58 (s, 1H), 7.48 (m, 2H), 7.26 (m, 1H), 4.35 (m, 1H), 3.79 (s, 1H), 3.44 (m, 4H), 2.74 (dd, 1H), 2.54 (s, 3H), 2.14 (m, 2H), 2.01 (d, 1H). Anal. ($C_{20}H_{21}NO_3$) C, H, N.

Example 31

2-Carbomethoxy-3-(4-fluorophenyl)-7β-hydroxy-8-methyl-8-azabicyclo{3.2.1}oct-2-ene (8c)

The procedure described above was followed. The product was obtained as a yellow gum (58%): $R_f$ 0.23 (10% Et$_3$N/EtOAc); $^1$H NMR δ 7.15–6.96 (m, 4H), 4.30 (m, 1H), 3.75 (s, 1H), 3.50 (s, 3H), 3.41 (m, 1H), 2.85 (bs, 1H), 2.64 (dd, 1H), 2.48 (s, 3H), 2.08 (m, 2H), 1.85 (d, 1H). Anal. ($C_{16}H_{18}FNO_3$) C, H, N.

Example 32

2-Carbomethoxy-3-phenyl-7β-hydroxy-8-methyl-8-azabicyclo{3.2.1}oct-2-ene (8d)

The procedure described above was followed to provide a white solid (62%): mp 113–114° C.; $R_f$ 0.23 (10% Et$_3$N/EtOAc); $^1$H NMR δ 7.36–7.30 (m, 3H), 7.15–7.08 (m, 2H), 4.31 (m, 1H), 3.73 (s, 1H), 3.51 (s, 3H), 3.41 (m, 1H), 2.66 (dd, 1H), 2.50 (s, 3H), 2.09 (m, 2H), 1.88 (d, 1H). Anal. ($C_{16}H_{19}NO_3$) C, H, N.

Example 33

2β-Carbomethoxy-3β-(3,4-dichlorophenyl)-6β-hydroxy-8-methyl-8-azabicyclo{3.2.1}octane (14a)

The procedure described above was followed to provide a white solid (88%): mp 93.5–95.5° C.; $R_f$ 0.18 (5% MeOH/CH$_2$Cl$_2$); $^1$H NMR δ 7.33 (d, 1H), 7.28 (d, 1H), 7.06 (dd, 1H), 4.44 (m, 1H), 3.84 (m, 1H), 3.51 (s, 3H), 3.30 (m, 1H), 2.79 (m, 1H), 2.68 (m, 1H), 2.56 (s, 3H), 2.45 (dt, 1H), 2.32–2.18 (m, 2H), 1.76 (m, 1H). Anal. ($C_{16}H_{19}Cl_2NO_3$) C, H, N.

Example 34

2β-Carbomethoxy-3β-(2-naphthyl)-6β-hydroxy-8-methyl-8-azabicyclo{3.2.1}octane (14b)

The procedure described above was followed to provide a white solid (89%): mp 84.0–86.0° C.; $R_f$ 0.23 (10% MeOH/CH$_2$Cl$_2$); $^1$H NMR δ 7.76 (t, 3H), 7.65 (s, 1H), 7.48–7.35 (m, 3H), 4.53 (m, 1H), 3.87 (m, 1H), 3.44 (s, 3H), 3.37 (m, 1H), 2.97–2.90 (m, 2H), 2.68 (dd, 1H), 2.60 (s, 3H), 2.32 (m, 2H), 1.93 (m, 1H), 1.78 (m, 1H). Anal. ($C_{20}H_{23}NO_3$) C, H, N.

Example 35

2β-Carbomethoxy-3β-(4-fluorophenyl)-6β-hydroxy-8-methyl-8-azabicyclo{3.2.1}octane (14c)

The procedure described above was followed to provide a white solid (30%): mp 162.0–164.0° C.; $R_f$ 0.21 (10% MeOH/CH$_2$Cl$_2$); $^1$H NMR δ 7.71 (m, 2H), 6.95 (m, 2H), 4.48 (m, 1H), 3.83 (m, 1H), 3.50 (s, 3H), 3.31 (s, 1H), 2.82–2.71 (m, 2H), 2.57 (s, 3H), 2.52 (dt, 1H), 2.35–2.21 (m, 2H), 1.79–1.75 (m, 2H). Anal. ($C_{16}H_{20}FNO_3$) C, H, N.

Example 36

2β-Carbomethoxy-3β-phenyl-6β-hydroxy-8-methyl-8-azabicyclo{3.2.1}octane (14d)

The procedure described above was followed to provide a white solid (33%): mp 150.0–152.0° C.; $R_f$ 0.13 (10% MeOH/CH$_2$Cl$_2$); $^1$H NMR δ 7.2–7.14 (m, 5H), 4.50 (m, 1H), 3.85 (m, 1H), 3.48 (s, 3H), 3.36 (m, 1H), 2.88–2.75 (m, 2H), 2.60 (s, 3H), 2.55 (dd, 1H), 2.29 (m, 2H), 1.81 (m, 1H). Anal. (C$_{16}$H$_{21}$NO$_3$) C, H, N.

Example 37

2β-Carbomethoxy-3β-(3,4-dichlorophenyl)-7β-hydroxy-8-methyl-8-azabicyclo{3.2.1}octane (15a)

The procedure described above was followed to provide a colorless crystalline solid (68%): mp 185.5–186.5° C.; $R_f$ 0.47 (10% Et$_3$N/EtOAc); $^1$H NMR δ 7.32 (d, 1H), 7.29 (d, 1H), 7.07 (dd, 1H), 4.53 (m, 1H), 3.60 (m, 1H), 3.53 (s, 3H), 3.00 (t, J=3.8 Hz, 1H), 2.68–2.64 (m, 1H), 2.55 (s, 3H), 2.50–2.44 (m, 1H), 2.23–2.08 (m, 2H), 1.78 (d, J=3.8 Hz, 1H), 1.59 (m, 1H). Anal. (C$_{16}$H$_{19}$Cl$_2$NO$_3$) C, H, N.

Example 38

(1S)-2β-Carbomethoxy-3β-(3,4-dichlorophenyl)-7β-hydroxy-8-methyl-8-azabicyclo{3.2.1}octane ((1S)-15a)

Obtained from (1S)-8a (vide infra) $\{\alpha\}^{21}_D$=+25° (c=1.3, CHCl$_3$) (>98% ee from $^1$H NMR of (1S)-28) mp 185.5–186.5° C.

Example 39

(1R)-2β-Carbomethoxy-3β-(3,4-dichlorophenyl)-7β-hydroxy-8-methyl-8-azabicyclo{3.2.1}octane ((1R)-15a)

Obtained from (1R)-2 (vide infra) $\{\alpha\}^{21}_D$=−26° (c=1.3, CHCl$_3$) (>98% ee from $^1$H NMR of (1R)-27) mp 186–187° C.

Example 40

2β-Carbomethoxy-3β-(2-naphthyl)-7β-hydroxy-8-methyl-8-azabicyclo{3.2.1}octane (15b)

The procedure described above was followed to provide a white crystalline solid: (78%); mp 207.5–208.5° C.; $R_f$ 0.15 (10% MeOH/CHCl$_3$); $^1$H NMR δ 7.76 (t, 3H), 7.65 (s, 1H), 7.47–7.35 (m, 3H), 4.63 (t, 1H), 3.66 (m, 1H), 3.58 (s, 1H), 3.45 (s, 3H), 3.17 (m, 1H), 2.97–2.87 (m, 1H), 2.67 (dt, 1H), 2.60 (s, 3H), 2.28–2.19 (m, 2H), 1.85 (bs, 1H), 1.76–1.70 (m, 1H). Anal. (C$_{20}$H$_{23}$NO$_3$) C, H, N.

Example 41

2β-Carbomethoxy-3β-(4-fluorophenyl)-7β-hydroxy-8-methyl-8-azabicyclo{3.2.1}octane (15c)

The procedure described above was followed to obtain a white crystalline solid (11%): mp 179.3–181.3° C.; $R_f$ 0.53 (10% Et$_3$N/EtOAc); $^1$H NMR δ 7.18 (m, 2H), 6.96 (m, 2H), 4.59 (m, 1H), 3.67–3.61 (m, 2H), 3.50 (s, 3H), 3.03 (m, 1H), 2.79–2.50 (m, 5H), 2.20 (m, 2H), 1.61 (m, 1H). Anal. (C$_{16}$H$_{20}$FNO$_3$) C, H, N.

Example 42

2β-Carbomethoxy-3β-phenyl-7β-hydroxy-8-methyl-8-azabicyclo{3.2.1}octane (15d)

The procedure described above was followed to obtain a white crystalline solid (17%): mp 165.8–167.8° C.; $R_f$ 0.13 (5% MeOH/CHCl$_3$); $^1$H NMR δ 7.30–7.13 (m, 5H), 4.58 (dd, J=6.6, 4.1 Hz, 1H), 3.62 (m, 1H), 3.53 (s, 1H), 3.49 (s, 3H), 3.06 (m, 1H), 2.75 (m, 1H), 2.57 (m, 4H), 2.22–2.11 (m, 2H), 1.64–1.59 (m, 1H). Anal. (C$_{16}$H$_{21}$NO$_3$) C, H, N.

Example 43

2β-Carbomethoxy-3α-(3,4-dichlorophenyl)-6β-hydroxy-8-methyl-8-azabicyclo{3.2.1}octane (17a)

The procedure described above was followed to obtain a white powder (18%): mp 129.1–131.1° C.; $R_f$ 0.57 (10% Et$_3$N/EtOAc); $^1$H NMR δ 7.34 (d, 1H), 7.26 (d, 1H), 7.02 (dd, 1H), 4.25 (m, 1H), 3.64–3.61 (m, 4H), 3.48–3.35 (m, 1H), 3.20 (d, 1H), 2.65 (s, 3H), 2.38–2.08 (m, 4H), 1.90 (bs, 1H), 1.29 (dd, 1H). Anal. (C$_{16}$H$_{19}$Cl$_2$NO$_3$) C, H, N.

Example 44

2β-Carbomethoxy-3α-(2-naphthyl)-6β-hydroxy-8-methyl-8-azabicyclo{3.2.1}octane (17b)

The procedure described above was followed to provide a white solid (77%): mp 93.5–94.5° C.; $R_f$ 0.45 (0.5% MeOH/CH$_2$Cl$_2$); $^1$H NMR δ 7.77 (m, 3H), 7.63 (s, 1H), 7.45 (m, 2H), 7.32 (d, 2H), 4.29 (m, 1H), 3.68 (m, 2H), 3.57 (s, 3H), 3.23 (d, 1H), 2.70 (s, 3H), 2.63 (d, 1H), 2.41 (dt, 1H), 2.21 (m, 2H), 1.54 (dd, 1H). Anal. (C$_{20}$H$_{23}$NO$_3$) C, H, N.

Example 45

2β-Carbomethoxy-3α-(4-fluorophenyl)-6β-hydroxy-8-methyl-8-azabicyclo{3.2.1}octane (17c)

The procedure described above was followed to provide a yellow crystalline solid (39%): mp 148.0–150.0° C.; $R_f$ 0.53 (10% MeOH/CH$_2$Cl$_2$); $^1$H NMR δ 7.13 (dd, 2H), 6.97 (t, 2H), 4.26 (m, 1H), 3.64–3.59 (m, 4H), 3.43 (m 1H), 3.21 (d, 1H), 2.67 (s, 3H), 2.40–2.12 (m, 4H), 1.31 (dd, 1H). Anal. (C$_{16}$H$_{20}$FNO$_3$) C, H, N.

Example 46

2β-Carbomethoxy-3α-phenyl-6β-hydroxy-8-methyl-8-azabicyclo{3.2.1}octane (17d)

The procedure described above was followed to provide a white powder (22%): mp 138.0–140.0° C.; $R_f$ 0.21 (10% Et$_3$N/EtOAc); $^1$H NMR δ 7.30–7.12 (m, 5H), 4.24 (m, 1H), 3.66–3.60 (m, 4H), 3.48 (dd, J=17.9, 9.1 Hz, 1H), 3.21 (d, J=8.8 Hz, 1H), 2.68 (s, 3H), 2.49 (d, J=9.1 Hz, 1H), 2.42–2.32 (m, 1H), 2.25–2.17 (m, 2H), 1.45–1.36 (m, 1H). Anal. (C$_{16}$H$_{21}$NO$_3$) C, H, N.

Example 47

2β-Carbomethoxy-3α-(3,4-dichlorophenyl)-7β-hydroxy-8-methyl-8-azabicyclo{3.2.1}octane (18a)

The procedure described above was followed to provide a colorless solid (87%): mp 148.5–150° C.; $R_f$ 0.18 (10% $Et_3N$, 40% EtOAc, 50% hexane); $R_f$ 0.53 (10% $Et_3N$/ EtOAc); $^1H$ NMR δ 7.31 (d, 1H), 7.26 (d, 1H), 7.25 (dd, 1H), 4.29 (m, 1H), 3.61 (s, 3H), 3.47–3.38 (m, 2H), 3.27 (s, 1H), 2.67 (s, 3H), 2.42–2.32 (m, 2H), 2.17–2.01 (m, 3H), 1.26 (dd, 1H). Anal. ($C_{16}H_{19}Cl_2NO_3$) C, H, N.

Example 48

(1S)-2β-Carbomethoxy-3α-(3,4-dichlorophenyl)-7β-hydroxy-8-methyl-8-azabicyclo{3.2.1}octane ((1S)-18a)

Obtained from (1S)-8a: $\{\alpha\}^{21}_D$=−48° (c=1.0, $CHCl_3$); $\{\alpha\}^{21}_D$=−36° (c=0.40, MeOH) (>98% ee from $^1H$ NMR of (1S)-27) mp 148.5–150° C.

Example 49

(1R)-2β-Carbomethoxy-3α-(3,4-dichlorophenyl)-7β-hydroxy-8-methyl-8-azabicyclo{3.2.1}octane ((1R)-18a)

Obtained from (1R)-2: $\{\alpha\}^{21}_D$=+47° (c=1.0, $CHCl_3$) (>98% ee from $^1H$ NMR of (1R)-27) mp 149–150° C.

Example 50

2β-Carbomethoxy-3α-(2-naphthyl)-7β-hydroxy-8-methyl-8-azabicyclo{3.2.1}octane (18b)

The procedure described above was followed to provide a yellow crystalline solid (62%): mp 140.1–141.9° C.; $R_f$ 0.20 (5% MeOH/$CH_2Cl_2$); $^1H$ NMR δ 7.82–7.76 (m, 3H), 7.63 (s, 1H), 7.49–7.41 (m, 2H), 7.32 (d, 1H), 4.33 (m, 1H), 3.64 (m, 1H), 3.57 (s, 3H), 3.50 (m, 1H), 3.32 (s, 1H), 2.73 (s, 3H), 2.67 (d, 1H), 2.20–2.08 (m, 3H), 1.53–1.46 (m, 1H). Anal. ($C_{20}H_{23}NO_3$) C, H, N.

Example 51

2β-Carbomethoxy-3α-(4-fluorophenyl)-7β-hydroxy-8-methyl-8-azabicyclo{3.2.1}octane (18c)

The procedure described above was followed to obtain a white crystalline solid (47%): mp 177.2–179.0° C.; $R_f$ 0.12 (EtOAc); $^1H$ NMR δ 7.18–7.10 (m, 2H), 6.99–6.93 (m, 2H), 4.29 (m, 1H), 3.59 (s, 3H), 3.51–3.38 (m, 2H), 3.26 (s, 1H), 2.70 (s, 3H), 2.47–2.35 (m, 2H), 2.18–2.00 (m, 2H), 1.29 (m, 1H). Anal. ($C_{16}H_{20}FNO_3$) C, H, N.

Example 52

2β-Carbomethoxy-3α-phenyl-7β-hydroxy-8-methyl-8-azabicyclo{3.2.1}octane (18d)

The procedure described above was followed to provide a white powder (26%): mp 165.0–167.0° C.; $R_f$ 0.19 (5% MeOH/$CH_2Cl_2$); $^1H$ NMR δ 7.31–7.15 (m, 5H), 4.29 (m, 1H), 3.59 (s, 3H), 3.52–3.42 (m, 2H), 3.29 (s, 1H), 2.71 (s, 3H), 2.54–2.36 (m, 2H), 2.18–2.02 (m, 2H), 1.39 (dd, 1H). Anal. ($C_{16}H_{21}NO_3$) C, H, N.

Preparation of 7α and 6α-hydroxy Tropanes (30).

Example 53

2β-Carbomethoxy-3α-(3,4-dichlorophenyl)-7α-benzoyloxy-8-methyl-8-azabicyclo{3.2.1}octane (29b)

To a solution of 2β-carbomethoxy-3α-(3,4-dichlorophenyl)-7β-hydroxy-8-methyl-8-azabicyclo{3.2.1}octane, 18a (0.46 g, 1.34 mmol) in THF (20 mL) with benzoic acid (0.49 g, 4.0 mmol) and triphenylphosphine (0.70 g, 2.68 mol) was added diethyl azodicarboxylate (DEAD) (0.46 g, 2.68 mmol) dropwise at 0° C. The reaction was kept stirring overnight at 22° C. The solvent was removed and the residue was purified by a flash column chromatography (30% hexanes in EtOAc) to give the product as a white solid (0.43 g, 72%). $R_f$ 0.53 (30% hexane, 70% EtOAc); $^1H$ NMR δ 8.06 (dd, 2H), 7.65 (d, 1H), 7.49 (t, 2H), 7.32 (d, 1H), 7.28 (d, 1H), 7.07 (dd, 1H), 5.68 (m, 1H), 3.73 (d, 1H), 3.55 (s, 3H), 3.48–3.31 (m, 2H), 3.10 (d, 1H), 3.01–2.85 (m, 1H), 2.53–2.47 (m, 4H), 1.64 (dd, 1H), 1.41 (dt, 1H).

Example 54

2β-Carbomethoxy-3α-(3,4-dichlorophenyl)-6α-benzoyloxy-8-methyl-8-azabicyclo{3.2.1}octane (29a)

2β-Carbomethoxy-3α-(3,4-dichlorophenyl)-6β-hydroxy-8-methyl-8-azabicyclo{3.2.1}octane, 17a (0.23 g) was treated as described above for the 7-hydroxy compound. A white solid was obtained (0.19 g, 63%): $R_f$ 0.77 (30% hexane, 70% EtOAc); $^1H$ NMR δ 8.14–8.02 (m, 2H), 7.63–7.46 (m, 3H), 7.29 (dd, 2H), 7.05 (dd, 1H), 5.60 (m, 1H), 3.68–3.60 (m, 4H), 3.45–3.35 (m, 2H), 3.11–2.93 (m, 1H), 2.63–2.49 (m, 4H), 2.30–2.15 (m, 1H), 1.85–1.95 (m, 2H).

Example 55

2β-Carbomethoxy-3α-(3,4-dichlorophenyl)-7α-hydroxy-8-methyl-8-azabicyclo{3.2.1}octane (30b)

To a solution of 2β-carbomethoxy-3α-(3,4-dichlorophenyl)-7α-benzoyloxy-8-methyl-8-azabicyclo{3.2.1}octane 29b (0.43 g, 0.95 mmol) in THF (26 mL) was added LiOH (0.085 g, 1.9 mmol in 5 ml $H_2O$). The resulting solution was stirred for 5 h at 22° C. and quenched with aqueous HCl (3%). The THF was removed and the aqueous layer was extracted with $CHCl_3$ (6×20 mL). The organic layers were combined and dried over $K_2CO_3$. The solvent was removed and the residue was purified by column chromatography (10% $Et_3N$ in EtOAc) to afford the product as a white gum which solidified slowly upon standing (0.19 g, 26%): mp 121–123° C.; $R_f$ 0.41 (10% $Et_3N$/EtOAc); $^1H$ NMR δ 7.36 (d, 1H), 7.33 (d, 1H), 7.12 (dd, 1H), 4.79 (ddd, J=9.9, 6.0, 3.8 Hz, 1H), 3.59 (s, 3H), 3.46–3.33 (m, 3H), 3.24 (t, J=7.9 Hz, 1H), 2.83–2.68 Hz (m, 1H), 2.55–2.43 (m, 4H), 1.40–1.25 (m, 2H). Anal. ($C_{16}H_{19}Cl_2NO_3$) C, H, N.

Example 56

2β-Carbomethoxy-3α-(3,4-dichlorophenyl)-6α-hydroxy-8-methyl-8-azabicyclo{3.2.1}octane (30a)

2β-Carbomethoxy-3α-(3,4-dichlorophenyl)-6α-benzoyloxy-8-methyl-8-azabicyclo{3.2.1}octane 29a (0.18 g, 0.39 mmol) was treated as described above and a white solid was obtained (51 mg, 38%): mp 161.2–162.2° C.; $R_f$ 0.26 (10% Et$_3$N in EtOAc); $^1$H NMR δ 7.35 (d, 1H), 7.34 (d, 1H), 7.11 (dd, 1H), 4.72 (m, 1H), 3.57 (s, 3H), 3.37–3.25 (m, 3H), 2.88–2.77 (m, 1H), 2.50 (d, 1H), 2.42 (s, 3H), 2.20–1.97 (m, 2H), 1.52 (dd, 1H). Anal. ($C_{16}H_{19}Cl_2NO_3$) C, H, N.

Oxidation of 7-hydroxy Tropanes to 7-ketones (19 and 20).

Example 57

2β-Carbomethoxy-3α-(3,4-dichlorophenyl)-8-methyl-8-azabicyclo{3.2.1}oct-7-one (20)

A solution of 2β-carbomethoxy-3α-(3,4-dichlorophenyl)-7β-hydroxy-8-methyl-8-azabicyclo{3.2.1}octane 18 (0.20 g, 0.58 mmol) in CH$_2$Cl$_2$ (5 ml) containing N-methylmorpholine N-oxide (1.5 eq) and 4 Å molecular sieves (0.5 g; powder) was stirred for 10 min at 22° C. under N$_2$ and then treated with tetra-n-propylammonium perruthenate (10% molar eq). The resulting solution was stirred overnight. The solvent was removed and the residue was purified by flash column chromatography (10% Et$_3$N, 30% EtOAc, 60% hexanes) to afford a white solid (0.16 g, 80%): mp 163.5–164.5° C.; $R_f$ 0.47 (10% Et$_3$N, 30% EtOAc, 60% hexanes); $^1$H NMR δ 7.34 (d, 1H), 7.29 (d, 1H), 7.02 (dd, 1H), 3.68–3.60 (m, 5H), 3.27 (m, 1H), 2.84 (dd, J=7.9, 1.9 Hz, 1H), 2.59–2.30 (m, 2H), 2.44 (s, 3H), 1.92 (d, J=18.4 Hz, 1H), 1.52 (ddd, J=14.0, 8.5, 1.9 Hz, 1H). Anal. ($C_{16}H_{17}Cl_2NO_3$) C, H, N.

Example 58

2β-Carbomethoxy-3β-(3,4-dichlorophenyl)-8-methyl-8-azabicyclo{3.2.1}oct-7-one (19)

2β-Carbomethoxy-3β-(3,4-dichlorophenyl)-7β-hydroxy-8-methyl-8-azabicyclo{3.2.1}octane, 15 was treated as described above and the product was obtained as a white solid (170 mg, 81%): mp 84.4–86.4° C.; $R_f$ 0.60 (10% Et$_3$N, 30% EtOAc, 60% hexanes); $^1$H NMR δ 7.35 (d, 1H), 7.32 (d, 1H), 7.09 (dd, 1H), 3.75 (dt, J=5.2, 1.3 Hz, 1H), 3.56 (s, 3H), 3.34 (s, 1H), 3.22 (t, J=3.8 Hz, 1H), 2.98 (dt, J=4.7, 12.9 Hz, 1H), 2.84 (dt, J=12.7, 3.3 Hz, 1H), 2.73 (dd, J 18.7, 7.4 Hz, 1H), 2.39 (s, 3H), 2.12 (d, J=18.7 Hz, 1H), 1.86 (dt, J 12.1, 3.3 Hz, 1H). Anal. ($C_{16}H_{17}Cl_2NO_3$) C, H, N.

Preparation of 2β-ethyl Ketone Tropanes (23 and 26).

Example 59

2β-Carbo-N-methoxy-N-methylamino-3α-(3,4-dichlorophenyl)-7β-methoxymethoxy-8-methyl-8-azabicyclo{3.2.1}octane (24) (Weinreb amide)

To a solution of N,O-dimethylhydroxylamine hydrochloride (0.34 g, 3.48 mmol) in CH$_2$Cl$_2$ (10 mL) was added Al(CH$_3$)$_3$ dropwise at –12° C. (glycol-dry ice bath) under N$_2$. The resulting solution was stirred for 10 min. At –12° C. before the cooling bath was removed and the reaction stirred at 22° C. for 30 min. The reaction was cooled to –12° C. and a solution of 2β-carbomethoxy-3α-(3,4-dichlorophenyl)-7β-methoxymethoxy-8-methyl-8-azabicyclo{3.2.1}octane, 12a (0.45 g, 1.16 mmol) in CH$_2$Cl$_2$ (4 mL) was transferred by cannula into the reaction flask and the reaction was stirred for 1 h at –12° C. and then 2 h at 22° C. Rochelle's salt solution (potassium sodium tartrate saturated in water) (~1 ml) was added and the mixture was stirred vigorously. Water was added to dissolve some solid salt and the aqueous layer was extracted with CHCl$_3$ (6×20 mL). The organic layers were combined and dried over K$_2$CO$_3$. The solvent was removed. The residue was purified by passing it through a short silica gel column (10% Et$_3$N in EtOAc) to afford a white solid (0.47 g, 89%). $R_f$ 0.39 (10% Et$_3$N, 30% EtOAc, 60% hexane); $^1$H NMR δ 7.29 (d, 1H), 7.26 (d, 1H), 7.05 (dd, 1H), 4.67 (dd, J=3.6, 6.8 Hz, 2H), 4.37 (dd, J=7.1, 3.3 Hz, 1H), 3.56 (s, 3H), 3.54–3.46 (m, 2H), 3.14 (m, 1H), 3.10 (s, 3H), 2.65 (d, J=11.3 Hz, 1H), 2.54 (s, 3H), 2.48–2.37 (m, 1H), 2.26–2.18 (m, 1H), 2.02 (dd, J=14.0, 7.4 Hz, 1H), 1.16–1.07 (m, 1H).

Example 60

2β-Carbo-N-methoxy-N-methylamine-3β-(3,4-dichlorophenyl)-7β-methoxymethoxy-8-methyl-8-azabicyclo{3.2.1}octane (21) (Weinreb amide)

The starting material 11a (0.47 g, 1.2 mmol) was treated as for the 3α compound shown above. A solid was obtained (0.31 g, 61%): $R_f$ 0.45 (10% Et$_3$N, 30% EtOAc, 60% hexane); $^1$H NMR δ 7.31 (d, 1H), 7.31 (d, 1H), 7.11 (dd, 1H), 4.69 (s, 2H), 4.34 (dd, J=7.7, 3.6 Hz, 1H), 3.66 (s, 3H), 3.61–3.58 (m, 2H), 3.42 (s, 3H), 3.28 (m, 1H), 3.05 (s, 3H), 2.74–2.6 (m, 2H), 2.49 (s, 3H), 2.28–2.20 (m, 1H), 2.09–2.02 (m, 1H), 1.60–1.56 (m, 1H).

Example 61

1-{3α-(3,4-Dichlorophenyl)-7β-methoxymethoxy-8-methyl-8-azabicyclo{3.2.1}oct-2-yl}propan-1-one (25)

To a solution of 2β-carbo-N-methoxy-N-methylamino-3α-(3,4-dichlorophenyl)-7β-methoxymethoxy-8-methyl-8-azabicyclo{3.2.1}octane, 24 (0.47 g, 1.13 mmol) in THF (anhydrous, 15 mL) was added ethyl magnesium bromide (3.4 ml, 1M in THF) dropwise at 0° C. under N$_2$. The reaction was slowly warmed to 22° C. and stirred overnight. The reaction was then quenched with aqueous sat. NH$_4$Cl solution. The THF was replaced by CH$_2$Cl$_2$. The aqueous layer was extracted by CHCl$_3$ (6×20 mL). The organic solution was dried over K$_2$CO$_3$ and solvent was removed to afford a white solid (0.45 g, ~100%). The sample was used for the next reaction without further purification. $R_f$ 0.67 (10% Et$_3$N, 30% EtOAc, 60% hexane); $^1$H NMR δ 7.30 (d, 1H), 7.23 (d, 1H), 7.00 (dd, 1H), 4.68 (dd, J=8.5, 1.7 Hz, 2H), 4.24 (dd, J=7.4, 3.6 Hz, 1H), 3.47–3.31 (m, 5H), 3.20 (s, 1H), 2.56–2.31 (m, 6H), 2.27–1.99 (m, 3H), 1.22–1.13 (m, 1H), 0.96 (t, J=7.1 Hz, 3H).

Example 62

1-{3β-(3,4-Dichlorophenyl)-7β-methoxymethoxy-8-methyl-8-azabicyclo{3.2.1}oct-2-yl}propan-1-one (22)

Weinreb amide 21 (0.31 g, 0.74 mmol) was treated as described above to obtain a white solid product (0.27 g, 95%). $R_f$ 0.71 (10% Et$_3$N, 30% EtOAc, 60% hexane); $^1$H NMR δ 7.30 (d, 1H), 7.27 (d, 1H), 7.06 (dd, 1H), 4.72 (s, 2H), 4.31 (dd, J=7.4, 3.6 Hz, 1H), 3.59–3.54 (m, 2H), 3.44 (s, 3H), 3.12 (m, 1H), 2.68–2.66 (m, 1H), 2.52–2.40 (m, 5H), 2.30–2.17 (m, 2H), 2.05 (dd, J=14.3, 7.7 Hz, 1H), 1.62–1.55 (m, 1H), 0.92 (t, J=7.1 Hz, 3H).

Example 63

1-{3α-(3,4-Dichlorophenyl)-7β-hydroxy-8-methyl-8-azabicyclo{3.2.1}oct-2-yl}propan-1-one (26)

The deprotection of the MOM group of 25 was carried out by the general method described earlier. 2β-(1-Propanoyl)-3α-(3,4-dichlorophenyl)-7β-methoxymethoxy-8-methyl-8-azabicyclo{3.2.1}octane (0.27 g) was used and the product was obtained as a white solid (0.23 g, 76%): mp 113.1–114.1° C.; $R_f$ 0.25 (10% Et$_3$N, 30% EtOAc, 60% hexanes); $^1$H NMR δ 7.32 (d, 1H), 7.22 (d, 1H), 6.97 (dd, 1H), 4.27 (m, 1H), 3.50–3.41 (m, 2H), 3.06 (s, 1H), 2.67 (s, 3H), 2.67 (s, 3H), 2.52–2.32 (m, 3H), 2.18–2.01 (m, 3H), 1.25 (m, 1H), 0.94 (t, J=7.4 Hz, 3H). Anal. ($C_{17}H_{21}Cl_2NO_2$) C, H, N, Cl.

Example 64

1-{3β-(3,4-Dichlorophenyl)-7β-hydroxy-8-methyl-8-azabicyclo{3.2.1}oct-2-yl}propan-1-one (23)

The deprotection of the MOM group of 22 was carried out by the general method described earlier. 2β-(1-Propanoyl)-3β-(3,4-dichlorophenyl)-7β-methoxymethoxy-8-methyl-8-azabicyclo{3.2.1}octane (0.28 g) was used and the product was obtained as a white solid (0.18 g, 73%): mp 195.5–196.5° C.;. $R_f$ 0.39 (10% Et$_3$N, 30% hexanes, 60% EtOAc); $^1$H NMR δ 7.31 (d, 1H), 7.26 (d, 1H), 7.05 (dd, 1H), 4.59 (p, J=3.3 Hz, 1H), 3.60 (m, 1H), 3.52 (m, 1H), 3.10 (dd, J=4.4, 3.3 Hz, 1H), 2.65–2.41 (m, 6H), 2.26 (q, J=7.4 Hz, 2H), 2.24–2.09 (m, 2H), 1.86 (d, J=3.8 Hz, 1H), 0.92 (t, J=7.4 Hz, 3H). Anal. ($C_{17}H_{21}Cl_2NO_2$) C, H, N.

Preparation of 7 and 6-hydroxy Difluoropines (32)

Example 65

2β-Carbomethoxy-3α-hydroxy-7β-methoxymethoxy-8-methyl-8-azabicyclo{3.2.1}octane (31b)

To a solution of 2β-carbomethoxy-7β-methoxymethoxy-8-methyl-3-oxo-8-azabicyclo{3.2.1}octane 1b (1.0 g, 3.89 mmol) in MeOH (100 mL) was added NaBH$_4$ (0.36 g, 9.72 mmol) at –78° C. The mixture was kept in a freezer (–25° C.) for 3 days. The reaction was quenched with H$_2$O (40 mL) and MeOH was removed. The aqueous layer was extracted with CH$_2$Cl$_2$ (6×20 mL). The extracts were combined and dried over K$_2$CO$_3$ and solvent was removed. The residue was purified by gradient flash chromatography (5% MeOH in CHCl$_3$ to 10% MeOH in CHCl$_3$) to give the product as a yellow oil (0.53 g, 52%). $R_f$ 0.21 (10% MeOH/CHCl$_3$); $^1$H NMR δ 4.67–4.58 (m, 3H), 4.29 (t, 1H), 3.77 (s, 3H), 3.52 (m, 1H), 3.34 (s, 3H), 3.31–3.23 (m, 2H), 2.93 (t, 1H), 2.58 (dd, 1H), 2.54 (s, 3H), 2.06–1.98 (m, 1H), 1.66 (d, 1H).

Example 66

2β-Carbomethoxy-3α-hydroxy-6β-methoxymethoxy-8-methyl-8-azabicyclo{3.2.1}octane (31a)

2β-Carbomethoxy-6β-methoxymethoxy-8-methyl-3-oxo-8-azabicyclo{3.2.1}octane 1a (1.0 g) was treated as described above to obtain the product as an oil (0.53 g, 52%). $R_f$ 0.21 (10% MeOH/CHCl3); $^1$H NMR δ 4.64 (s, 2H), 4.59 (dd, 1H), 4.28 (m, 1H), 3.74 (s, 3H), 3.59 (m, 1H), 3.46 (s, 1H), 3.36 (s, 3H), 3.17 (s, 1H), 2.89 (m, 1H), 2.63–2.55 (m, 4H), 2.09–1.95 (m, 2H), 1.76 (d, 1H).

Example 67

2β-Carbomethoxy-3α-bis(fluorophenyl)methoxy-7β-hydroxy-8-methyl-8-azabicyclo{3.2.1}octane (32b)

A solution of 2β-carbomethoxy-3α-hydroxy-7β-methoxymethoxy-8-methyl-8-azabicyclo{3.2.1}octane 31b (0.52 g, 2.04 mmol) and 4,4'-difluorobenzhydrol (0.53 g, 2.22 mmol) in CH$_2$Cl$_2$ (50 mL) with p-toluenesulfonic acid (0.39 g, 2.04 mmol) was placed in a round bottom flask equipped with a soxhlet condenser in which a thimble filled with molecular sieves (3 Å) was placed. The reaction was heated to reflux overnight during which time the molecular sieves were replaced with fresh sieves several times. The reaction was quenched with sat NaHCO$_3$ and the aqueous layer was extracted with CH$_2$Cl$_2$. The extracts were combined and dried over K$_2$CO$_3$ and solvent was removed on a rotary evaporator. The residue was purified by column chromatography (5% MeOH in EtOAc to 10% MeOH in EtOAc) to afford the desired product as a white solid (0.21 g, 22%): mp 150–152° C.; $R_f$ 0.09 (5% MeOH, EtOAc); $^1$H NMR δ 7.25 (dd, 4H), 6.99 (m, 4H), 5.45 (s, 1H), 4.42 (dd, J=7.1, 2.8 Hz, 1H), 4.24 (t, J=4.4 Hz, 1H), 3.71 (s, 3H), 3.64 (m, 1H), 3.35 (m, 1H), 2.97 (s, 1H), 2.78 (s, 1H), 2.61 (s, 3H), 2.53 (dd, J=13.1, 7.4 Hz, 1H), 2.15 (m, 1H), 2.02 (m, 1H), 1.69 (d, J=14.3 Hz, 1H). Anal. ($C_{23}H_{25}F_2NO_4$) C, H, N.

Example 68

2β-Carbomethoxy-3α-bis(4-fluorophenyl)methoxy-6β-hydroxy-8-methyl-8-azabicyclo{3.2.1}octane (32a)

2β-Carbomethoxy-3α-hydroxy-6β-methoxymethoxy-8-methyl-8-azabicyclo{3.2.1}octane 31a (0.54 g, 2.10 mmol) was treated as described above and the product was obtained as a white foam. (0.17 g, 17%): $R_f$ 0.32 (10% MeOH/CHCl$_3$); $^1$H NMR δ 7.25 (dd, J=8.5, 5.8 Hz, 4H), 6.99 (dt, J=8.5, 0.8 Hz, 4H), 5.34 (s, 1H), 4.48 (dd, J=7.2, 2.8 Hz, 1H), 4.20 (m, 1H), 3.73 (s, 3H), 3.61 (d, J=8.0 Hz, 1H), 3.26 (s, 1H), 3.17 (s, 1h), 2.88 (bs, 1H), 2.58 (s, 3H), 2.48 (dd, J=13.7, 7.14 Hz, 1H), 2.07 (ddd, J=14.0, 7.4, 2.7 Hz, 1H), 1.97 (d, J=16.8 Hz, 1H). Anal. ($C_{23}H_{25}F_2NO_4$) C, H, N.

Resolution of 7-hydroxy Tropanone.

Example 69

(1R)-2-Carbomethoxy-3-(1'S)-camphanyl-7β-methoxymethoxy-8-methyl-8-azabicyclo{3.2.1}oct-2-ene (27)

To a solution of racemic 2β-carbomethoxy-7β-methoxymethoxy-8-methyl-3-oxo-8-azabicyclo{3.2.1}octane 2b (7.1 g, 27.6 mmol) in THF (anhydrous, 100 mL) pooped at −78° C., NaN(TMS)₂ (35.9 mL, 1 M in THF) was added dropwise by syringe. The resulting solution was stirred for 45 min. At −78° C. and (1S)-(−)-camphanic chloride (8.3 g, 38.6 mmol) was added. The solution was stirred overnight, during which time it slowly warmed up to 22° C. The reaction was quenched with sat. NaHCO₃ (20 mL). The THF was replaced with CH₂Cl₂. The organic layer was separated and aqueous layer was back extracted with CH₂Cl₂ (6×20 mL). The organic extracts were combined and dried over K₂CO₃ and solvent was removed. The residue was purified by flash chromatography (5% MeOH in EtOAc) to afford the product (7.75 g, 64%) as a yellow oil which solidified upon standing for 3 days. NMR showed two diastereoisomers in the sample. The (1R,1'S) diastereoisomer was separated by recrystallization (5 times) from benzene/heptane to give diasteromerically pure 27 as a white solid (1.4 g, 36%, >98% de by $^1$H NMR). Despite repeated efforts, the (1S,1'S) diastereomer could not be isolated pure. The $^1$H NMR of the diastereomeric mixture is provided below. Of particular interest is the region 1.2–0.7 ppm as in benzene-d₆ the two diastereomers show different chemical shifts. $^1$H NMR (C₆D₆) δ 4.70 (m, 1H), 4.55 (m, 1H), 4.19 (m, 1H), 4.11 (m, 1H), 3.28 (m, 3H), 3.21 (m, 3H), 2.9 (m, 1H), 2.35 (m, 3H), 2.34–2.18 (m, 2H), 2.11–2.02 (m, 2H), 1.66 (m, 1H), 1.29–1.21 (m, 4H), 1.026 (s, 3H, 1S,1'S), 0.992 (s, 3H, 1R,1'S), 0.897 (s, 3H, 1S,1'S), 0.890 (s, 3H, 1R,1'S), 0.817 (s, 3H, 1S,1'S), 0.803 (s, 3H, 1R;1'S).

The (1R,1'S) product of recrystallization 27 was diasterously pure (>98% de) as confirmed by the complete absence of the (1S,1'S) -diastereomer at 1.015 ppm. R$_f$ 0.42 (5% MeOH/EtOAc); $^1$H NMR (C₆D₆) δ 4.70 (d, J=6.6 Hz, 1H), 4.55 (d, J=6.6 Hz, 1H), 4.19 (dd, J=7.4, 2.2 Hz, 1H), 4.11 (s, 1H), 3.28 (s, 3H), 3.21 (s, 3H), 2.9 (m, 1H), 2.35 (s, 3H), 2.34–2.18 (m, 2H), 2.11–2.02 (m, 2H), 1.66 (dd, J=13.4, 7.4 Hz, 1H), 1.29–1.21 (m, 4H), 0.98 (s, 3H), 0.89 (s, 3H), 0.78 (s, 3H).

Example 70

(1R)-7β-methoxymethoxy-2-methoxycarbonyl-8-methyl-3-oxo-8-azabicyclo{3.2.1}octane ((1R)-2)

A solution of (1R)-2-carbomethoxy-3-(1'S)-camphanyl-7β-hydroxy-8-methyl-8-azabicyclo{3.2.1}oct-2-ene 27 (1.40 g, 3.20 mmol) in THF (50 mL) was treated with LiOH aqueous solution (0.26 g, 6.4 mmol, 16 mL H₂O) and the resulting solution was stirred at 22° C. for 3 h. The THF was removed in vacuo and K₂CO₃ (8 g) was added to the aqueous solution which was exhaustively extracted with CH₂Cl₂. The CH₂Cl₂ extracts were combined and dried over K₂CO₃. Solvent was removed to obtain a white solid (1R-2) (0.89 g) that was used for the ensuing steps without further purification. $^1$H NMR δ 4.67 (d, 1H), 4.54 (d, 1), 3.98 (s, 1H), 3.93 (dd, 1H), 3.30 (s, 3H), 3.21 (s, 3H), 2.92 (dd, 1H), 2.43 (m, 1H), 2.50 (dd, 1H), 2.21 (s, 3H), 2.05 (dd, 1H), 1.51 (dd, 1H), 1.42 (d, 1H).

Example 71

(1S)-2-Carbomethoxy-3-(3,4-dichlorophenyl)-7β-(1'S)-camphanyloxy-8-methyl-8-azabicyclo{3.2.1}oct-2-ene (28)

A solution of racemic 2-carbomethoxy-3-(3,4-dichlorophenyl)-7β-hydroxy-8-methyl-8-azabicyclo{3.2.1}oct-2-ene 8a (11.1 g, 32 mmol) in CH₂Cl₂ (250 mL) with Et₃N (6.8 mL, 48.7 mmol) was treated with 1S-(−)-camphanic chloride (10.5 g, 48.7 mmol) at 0° C. The resulting solution was stirred overnight at 22° C. and then quenched with NaHCO₃ (sat.). The organic layer was separated and the aqueous layer was extracted with CH₂Cl₂ (3×20 mL). The organic layers were combined and dried over MgSO₄. The solvent was removed and the crude product containing the two diastereoisomers was separated by two consecutive gravity columns (10% Et₃N, 30% EtOAc, 60% hexanes). The pure (1S,1'S) product 28 (2.4 g) was obtained as a yellow solid. A further 1.8 g was obtained as a mixture of diastereomers: R$_f$ (one elution: both diastereomers run together) 0.14 (10% Et₃N, 30% EtOAc, 60% hexane); R$_f$(two elutions) (1S,1'S) 0.25 (1R,1'S) 0.18 (10% Et₃N, 30% EtOAc, 60% hexane).

The $^1$H NMR of 28 showed no trace of the (1R,1S) diastereomer and was therefore diastereomerically pure (de>98%).$^1$H NMR (C₆D₄) δ 7.08 (d, 1H), 7.02 (d, 1H), 6.47 (dd, J=8.3, 2.2 Hz, 1H), 5.34 (dd, J=7.4, 2.2 Hz, 1H), 4.16 (s, 1H), 3.15 (s, 3H), 2.89 (dd, J=6.9, 4.7 Hz, 1H), 2.19 (s, 3H), 2.17–2.07 (m, 2H), 1.98 (dd, J=18.4, 5.2 Hz, 1H), 1.82–1.65 (m, 2H), 1.25–1.09 (m, 3H), 0.92 (s, 3H), 0.82 (s, 3H), 0.72 (s, 3H).

Example 72

(1R)-2-Carbomethoxy-3-(3,4-dichlorophenyl)-7β-camphanoly-8-methyl-8-azabicyclo{3.2.1}oct-2-ene ((1R)-28)

In order to confirm that the above compound is 1S configured, a similar reaction was carried out by using the 1R ene compound. $^1$H NMR (C₆D₆) δ 7.11 (d, 1H), 7.05 (d, 1H), 6.52 (dd, 1H), 5.36 (dd, J=7.4, 2.2 Hz, 1H), 4.18 (s, 1H), 3.17 (s, 3H), 2.94 (dd, J=6.9, 4.7 Hz, 1H), 2.20 (s, 3H), 2.16–1.98 (m, 3H), 1.84 (dd, J=14.3, 7.6 Hz, 1H), 1.74–1.65 (m, 1H), 1.25–1.10 (m, 3H), 0.89 (s, 3H), 0.83 (s, 3H), 0.75 (s, 3H).

Example 73

Single-Crystal X-ray Analysis of (1R)-8a

Monoclinic crystals of the purified (1R)-8a were obtained from CH₂Cl₂/heptane. A representative crystal was selected and a data set was collected at room temperature. Pertinent crystal, data collection and refinement parameters: crystal size, 0.66×0.50×0.22 mm; cell dimensions, a=18.382 (1) Å, b=6.860 (1) Å, c=16.131 (1) Å, α=90°, β=124.65 (1)°, γ=90°; formula, C₁₆H₁₇Cl₂NO₃; formula weight=342.21; volume=1673.3 (2) Å³; calculated density=1.358 g cm⁻³; space group=C2; number of reflections=1749 of which 1528 were considered independent (R$_{int}$=0.0300). Refinement method was full-matrix least-squares on F². The final R-indices were {I>2σ(I)} R1=0.0364, wR2=0.0987.

Example 74

Single-Crystal X-Ray Analysis of (1R)-18a

Monoclinic crystals of the purified (1R)-18a were obtained from ethyl CH₂Cl₂/heptane. A representative crystal was selected and a data set was collected at room temperature. Pertinent crystal, data collection and refinement parameters: crystal size, 0.72×0.30×0.14 mm; cell dimensions, α=5.981 (1) Å, b=7.349 (1) Å, c=18.135 (1) Å, α=90°, β=96.205 (6)°, α=90°; formula, C₁₆H₁₉Cl₂NO₃; formula weight=344.22; volume=792.29 (12) Å³; calculated density=1.443 g cm$^{-3}$; space group=P2$_1$; number of reflections=1630 of which 1425 were considered independent (R$_{int}$=0.0217). Refinement method was full-matrix least-squares on F$^2$. The final R-indices were {I>2σ(I)} R$_{1=0.0298}$, wR2=0.0858.

Example 75

Single-Crystal X-Ray Analysis of (1S)-18a

Monoclinic crystals of the purified (1S)-18a were obtained from CH$_2$Cl$_2$/heptane. A representative crystal was selected and a data set was collected at room temperature. Pertinent crystal, data collection and refinement parameters: crystal size, 0.64×0.32×0.18 mm; cell dimensions, α=15.000 (1) Å, b=7.018 (1) Å, c=15.886 (1) Å, α=90°, β=99.34 (1)°, α=90°; formula, C$_{16}$H$_{19}$Cl$_2$NO$_3$; formula weight=344.22; volume=1650.1 (2) Å$^3$; calculated density=1.386 g cm$^{-3}$; space group=P2(1); number of reflections=3267 of which 2979 were considered independent (R$_{int}$=0.0285). Refinement method was full-matrix least-squares on F$^2$. The final R-indices were {I>2σ(I)} R$_{1=0.0449}$, wR2=0.1236.

Example 76

Tissue Sources and Preparation

Brain tissue from adult male and female cynomolgus monkeys (*Macaca fasicularis*) and rhesus monkeys (*Macaca mulatta*) was stored at −85° C. in the primate brain bank at the New England Regional Primate Research Center. We recently cloned the DAT and SERT from both species and found them to have virtually identical protein sequences (Miller, G. M. et al., *Brain Res. Mol. Brain Res.* 2001, 87, 124–143). The caudate-putamen was dissected from coronal slices and yielded 1.4±0.4 g tissue. Membranes were prepared as described previously. Briefly, the caudate-putamen was homogenized in 10 volumes (w/v) of ice-cold Tris.HCl buffer (50 mM, pH 7.4 at 4° C.) and centrifuged at 38,000×g for 20 min in the cold. The resulting pellet was suspended in 40 volumes of buffer, and the entire was procedure was repeated twice. The membrane suspension (25 mg original wet weight of tissue/ml) was diluted to 12 ml/ml for {$^3$H}WIN 35,428 or {$^3$H}citalopram assay in buffer just before assay and was dispersed with a Brinkmann Polytron homogenizer (setting #5) for 15 sec. All experiments were conducted in triplicate and each experiment was repeated in each of 2–3 preparations from individual brains.

Example 77

Dopamine Transporter Assay

The dopamine transporter was labeled with {$^3$H}WIN 35,428 ({$^3$H}CFT, (1R)-2β-carbomethoxy-3β-(4-fluorophenyl)-N-{$^3$H}methyltropane, 81–84 Ci/mmol, DuPont-NEN). The affinity of {$^3$H}WIN 35,428 for the dopamine transporter was determined in experiments by incubating tissue with a fixed concentration of {$^3$H}WIN 35,428 and a range of concentration of unlabeled WIN 35,428. The assay tubes received, in Tris.HCl buffer (50 mM, pH 7.4 at 0–4° C.; NaCl 100 mM), the following constituents at a final assay concentration: WIN35,428, 0.2 ml (1 pM-100 or 300 nM), {$^3$N}WIN 35,428 (0.3 nM); membrane preparation 0.2 mL (4 mg original wet weight of tissue/mL). The 2 h incubation (0–4° C.) was initiated by addition of membranes and terminated by rapid filtration over Whatman GF/B glass fiber filters pre-soaked in 0.1% bovine serum albumin (Sigma Chem. Co.). The filters were washed twice with 5 mL Tris.HCl buffer (50 mM), incubated overnight at 0–4° C. in scintillation fluor (Beckman Ready-Value, 5 mL) and radioactivity was measured by liquid scintillation spectrometry (Beckman 1801). Cpm were converted to dpm following determination of counting efficiency (>45%) of each vial by external standardization.

Total binding was defined as {$^3$H}WIN 35,428 bound in the presence of ineffective concentrations of unlabeled WIN 35,428 (1 or 10 pM). Non-specific binding was defined as {$^3$H}WIN 35,428 bound in the presence of an excess (30 μM) of (−)-cocaine. Specific binding was the difference between the two values. Competition experiments to determine the affinities of other drugs at {$^3$H}WIN 35,428 binding sites were conducted using procedures similar to those outlined above. Stock solutions of water-soluble drugs were dissolved in water or buffer and stock solutions of other drugs were made in a range of ethanol/HCl solutions or other appropriate solvents. Several of the drugs were sonicated to promote solubility. The stock solutions were diluted serially in the assay buffer and added (0.2 mL) to the assay medium as described above. IC$_{50}$ values were computed by the EBDA computer program and are the means of experiments conducted in triplicate.

Example 78

Serotonin Transporter Assay

The serotonin transporter was assayed in caudate-putamen membranes using conditions similar to those for the dopamine transporter. The affinity of {$^3$H}citalopram (spec. act.: 82 Ci/mmol, DuPont-NEN) for the serotonin transporter was determined in experiments by incubating tissue with a fixed concentration of {$^3$H}citalopram and a range of concentrations of unlabeled citalopram. The assay tubes received, in Tris.HCl buffer (50 mM, pH 7.4 at 0–4° C.; NaCl 100 mM), the following constituents at a final assay concentration: citalopram, 0.2 ml (1 pM–100 or 300 nM), {$^3$H}citalopram (1 nM); membrane preparation 0.2 ml (4 mg original wet weight of tissue/mL). The 2 h incubation (0–4° C.) was initiated by addition of membranes and terminated by rapid filtration over Whatman GF/B glass fiber filters pre-soaked in 0.1% polyethyleneimine. The filters were washed twice with 5 ml Tris.HCl buffer (50 mM), incubated overnight at 0–4° C. in scintillation fluor (Beckman Ready-Value, 5 mL) and radioactivity was measured by liquid scintillation spectrometry (Beckman 1801). Cpm were converted to dpm following determination of counting efficiency (>45%) of each vial by external standardization. Total binding was defined as {$^3$H}citalopram bound in the presence of ineffective concentrations of unlabeled citalopram (1 or 10 pM). Non-specific binding was defined as {$^3$H}citalopram bound in the presence of an excess (10 μM) of fluoxetine. Specific binding was the difference between the two values. Competition experiments to determine the affinities of other drugs at {$^3$H}citalopram binding sites were conducted using procedures similar to those outlined above. IC$_{50}$ values were computed by the EBDA computer program and are the means of experiments conducted in triplicate.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

All references cited are incorporated herein in their entirety by reference.

What is claimed is:

1. A compound having the structural formula:

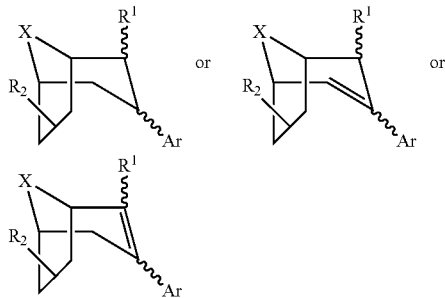

wherein:
$R_1 = COR_3$, and is α or β;
$R_2 = OH$ or $O$, is a 6- or 7-substituent, and if $R_2$ is OH, it is α or β;
$X = NR_3$ or $NSO_2R_3$, with the N being a member of the ring;
$R_3 = H$, $(CH_2)_nC_6H_4Y$, $C_6H_4Y$, $CHCH_2$, lower alkyl, lower alkenyl or lower alkynyl;
$Y = H$, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$;
$Ar = $ phenyl-$R_5$, naphthyl-$R_5$, anthracenyl-$R_5$, phenanthrenyl-$R_5$, or diphenylmethoxy-$R_5$;
$R_5 = H$, Br, Cl, I, F, OH, $OCH_3$, $CF_3$, $NO_2$, $NH_2$, CN, $NHCOCH_3$, $N(CH_3)_2$, $(CH_2)nCH_3$, $COCH_3$, $C(CH_3)_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-C, 3-OH-4-F, 3-Cl-4-OH, 3-F-4-OH, lower alkyl, lower alkoxy, lower alkenyl, lower alkynyl, CO(lower alkyl), or CO(lower alkoxy); and
n=0, 1, 2, 3, 4 or 5.

2. The compound of claim 1, which is a 1-S enantiomer.
3. The compound of claim 1, wherein Ar is a 3α-group.
4. The compound of claim 1, wherein Ar is a 3β-group.
5. The compound of claim 1, wherein $R_2$ is OH, and X is $NR_3$.
6. The compound of claim 1, wherein wherein the compound has an $IC_{50}$ SERT/DAT ratio of greater than about 10, preferably greater than about 30 and more preferably 50 or more.
7. The compound of claim 1, having an $IC_{50}$ at the DAT of less than about 500 nM, preferably less than 60 nM, more preferably less than about 20, and most preferably less than about 10.
8. The compound of claim 1, wherein X is $NR_3$ or $NSO_2R_2$, and Ar is phenyl, substituted phenyl, diarylmethoxy or subsituted diarylmethoxy.
9. The compound of claim 8, wherein the substitutent is a halogen.
10. The compound of claim 8, wherein the AR is a mono- or di-halogen substituted phenyl.
11. The compound of claim 1, wherein the aryl ring is substituted with one or more halide atoms, hydroxy groups, nitro groups, amino groups, cyano groups, lower alkyl groups having from 1–8 carbon atoms, lower alkoxy groups having from 1–8 carbon atoms, lower alkenyl groups having from 2–8 carbon atoms, or lower alkynyl groups having from 2–8 carbon atoms.

12. The compound of claim 11, wherein the aryl ring can be substituted with chloride, fluoride or iodide.
13. The compound of claim 11, wherein an amino group is a mono- or di-alkyl substituted group having from 1–8 carbon atoms.
14. The compound of claim 11, wherein the aryl group has a substituent selected from the group consisting of Br, Cl, I, F, OH, $OCH_3$, $CF_3$, $NO_2$, $NH_2$, CN, $NHCOCH_3$, $N(CH_3)_2$, $COCH_3$, $C(CH_3)_3$, $(CH_2)_nCH_3$ where n=0–6, allyl, isopropyl and isobutyl.
15. The compound of claim 1, wherein the aryl group has a substituent selected from the group consisting of lower alkyl, lower alkenyl and lower alkynyl.
16. The compound of claim 1, wherein the aryl group is substituted with a member of the group consisting of 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH and 3-F-4-OH.
17. The compound of claim 8, wherein $R_2$ is OH.
18. The compound of claim 1 having the following structural formula:

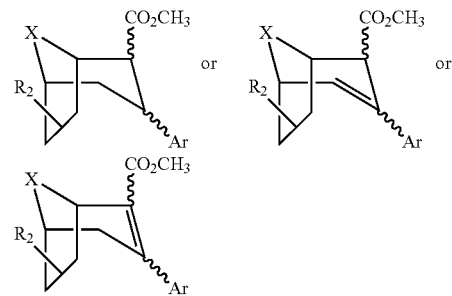

where X is $NR_3$, $R_3$ is $CH_2CH_3$, $R_2$ is OH or O in the 6- or 7-position, Ar is phenyl or naphthyl either of which can be substituted with halogen, alkenyl having 2–8 carbon atoms or alkynyl having 2–8 carbon atoms.

19. The compound of claim 18, wherein Ar is substituted with 4-Cl, 4-F, 4-Br, 4-I, 3,4-Cl$_2$, ethenyl, propenyl, butenyl, propynyl or butynyl.
20. The compound of claim 18, wherein $R_2$ is OH.
21. The compound of claim 18 selected from the group consisting of:
   a. 1-[3α-(3,4-Dichlorophenyl)-7β-hydroxy-8-methyl-8-azabicyclo[3.2.1]oct-2-yl]propan-1-one,
   b. 1-[3β-(3,4-Dichlorophenyl)-7β-hydroxy-8-methyl-8-azabicyclo[3.2.1]oct-2-yl]propan-1-one.
22. The compound of claim 1 selected from the group consisting of:
   a. 1-[3α-(3,4-Dichlorophenyl)-7β-hydroxy-8-methyl-8-azabicyclo[3.2.1]oct-2-yl]propan-1-one;
   b. 1-[3β-(3,4-Dichlorophenyl)-7β-hydroxy-8-methyl-8-azabicyclo[3.2.1]oct-2-yl]propan-1-one.
23. A pharmaceutical composition comprising a therapeutically effective amount of the compound of claim 1 and a pharmaceutically acceptable carrier.

24. A compound having the structural formula:

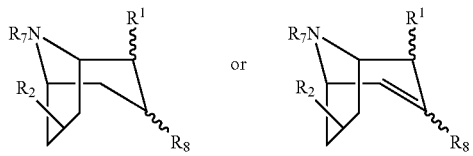

wherein:

$R_1$=$COR_3$, $CON(R_7)OR_7$ and is α or β;
$R_2$=$OR_9$ and is a 6- or 7-substituent;
$R_3$=H, $(CH_2)_nC_6H_4Y$, $C_6H_4Y$, $CHCH_2$, lower alkyl, lower alkenyl or lower alkynyl;
Y=H, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$;
R8=camphanoyl, phenyl-$R_5$, naphthyl-$R_5$, anthracenyl-$R_5$, phenanthrenyl-$R_5$, or diphenylmethoxy-$R_5$;
$R_5$=H, Br, Cl, I, F, OH, $OCH_3$, $CF_3$, $NO_2$, $NH_2$, CN, $NHCOCH_3$, $N(CH_3)_2$, $(CH_2)nCH_3$, $COCH_3$, $C(CH_3)_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-di$OCH_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);
n=0, 1, 2, 3, 4 or 5;
$R_7$=lower alkyl; and
R9=a protecting group.

25. The compound of claim 24 selected from the group consisting of:

a) 2β-Carbo-N-methoxy-N-methylamino-3α-(3,4-dichlorophenyl)-7β-methoxymethoxy-8-methyl-8-azabicyclo[3.2.1]octane;
b) 2β-Carbo-N-methoxy-N-methylamine-3β-(3,4-dichlorophenyl)-7β-methoxymethoxy-8-methyl-8-azabicyclo[3.2.1]octane;
c) 1-[3α-(3,4-Dichlorophenyl)-7β-methoxymethoxy-8-methyl-8-azabicyclo[3.2.1]oct-2-yl]propan-1-one;
d) 1-[3β-(3,4-Dichlorophenyl)-7β-methoxymethoxy-8-methyl-8-azabicyclo[3.2.1]oct-2-yl]propan-1-one.

26. A compound having the structural formula:

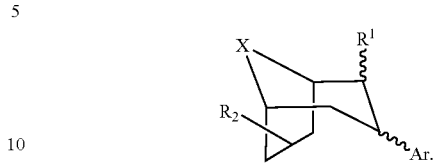

wherein:

$R_1$=$COOR_7$, $COR_3$, lower alkyl, lower alkenyl, lower alkynyl, $CONHR_4$, or $COR_6$ and is α or β;
$R_2$=O and is a 6- or 7-substituent;
X=$NR_3$, with the N being a member of the ring;
$R_3$=H, $(CH_2)_nC_6H_4Y$, $C_6H_4Y$, $CHCH_2$, lower alkyl, lower alkenyl or lower alkynyl;
Y=H, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$;
$R_4$=$CH_3$, $CH_2CH_3$, or $CH_3SO_2$;
$R_6$=morpholinyl or piperidinyl;
Ar=phenyl-$R_5$, naphthyl-$R_5$, anthracenyl-$R_5$, phenanthrenyl-$R_5$, or diphenylmethoxy-$R_5$;
$R_5$=H, Br, Cl, I, F, OH, $OCH_3$, $CF_3$, $NO_2$, $NH_2$, CN, $NHCOCH_3$, $N(CH_3)_2$, $(CH_2)nCH_3$, $COCH_3$, $C(CH_3)_3$ where n=0–6, 4-F, 4-Cl, 4-I, 2-F, 2-Cl, 2-I, 3-F, 3-Cl, 3-I, 3,4diCl, 3,4-diOH, 3,4-diOAc, 3,4-di$OCH_3$, 3-OH-4-F, 3-Cl-4-OH, 3-F-4-OH, lower alkyl, lower alkoxy, lower alkenyl, lower alkynyl, CO(lower alkyl), or CO(lower alkoxy);
n=0, 1, 2, 3, 4 or 5; and
$R_7$=lower alkyl.

27. The compound of claim 26, which is a 1-S enantiomer.
28. The compound of claim 26, wherein Ar is a 3α-group.
29. The compound of claim 26, wherein Ar is a 3β-group.

* * * * *

UNITED STATES PATENT AND TRADEMARK OFFICE
CERTIFICATE OF CORRECTION

PATENT NO. : 7,199,132 B2
APPLICATION NO. : 10/033621
DATED : April 3, 2007
INVENTOR(S) : Peter C. Meltzer et al.

Page 1 of 1

It is certified that error appears in the above-identified patent and that said Letters Patent is hereby corrected as shown below:

At Col. 1, line 6, insert the following paragraph(s):

--FEDERALLY SPONSORED RESEARCH

This invention was made with Government support under Grant Nos. DA006303, DA078081, DA011452, DA000304, DA011558 and RR000168 awarded by the National Institutes of Health. The Government has certain rights in this invention.--

Signed and Sealed this

Tenth Day of August, 2010

David J. Kappos
*Director of the United States Patent and Trademark Office*

UNITED STATES PATENT AND TRADEMARK OFFICE
CERTIFICATE OF CORRECTION

Page 1 of 1

PATENT NO. : 7,199,132 B2
APPLICATION NO. : 10/033621
DATED : April 3, 2007
INVENTOR(S) : Meltzer et al.

It is certified that error appears in the above-identified patent and that said Letters Patent is hereby corrected as shown below:

In the Specification

Please delete the paragraph starting at Column 1, Line number 6, and insert the following paragraph:
--GOVERNMENT FUNDING
This invention was made with government support under DA000304, DA006303, DA009462, SA048309, RR000168, and DA078081 awarded by the National Institutes of Health. The government has certain rights in the invention.--

This certificate supersedes the Certificate of Correction issued August 10, 2010.

Signed and Sealed this
Thirty-first Day of December, 2024

Derrick Brent
*Acting Director of the United States Patent and Trademark Office*